US010000563B2

(12) United States Patent
Jaspers et al.

(10) Patent No.: US 10,000,563 B2
(45) Date of Patent: *Jun. 19, 2018

(54) MONOCLONAL ANTIBODIES THAT BIND BOTH IL-17A AND IL-17F

(71) Applicant: ZymoGenetics, Inc., Princeton, NJ (US)

(72) Inventors: Stephen R. Jaspers, Brewster, NY (US); Scott R. Presnell, Tacoma, WA (US); Monica J. Huber, Bothell, WA (US)

(73) Assignee: ZYMOGENETICS, INC., Seattle, WA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/208,202

(22) Filed: Jul. 12, 2016

(65) Prior Publication Data

US 2016/0311897 A1    Oct. 27, 2016

Related U.S. Application Data

(60) Division of application No. 14/493,389, filed on Sep. 23, 2014, now Pat. No. 9,416,183, which is a division of application No. 13/910,311, filed on Jun. 5, 2013, now Pat. No. 8,871,467, which is a continuation of application No. 13/539,534, filed on Jul. 2, 2012, now Pat. No. 8,557,544, which is a division of application No. 12/832,311, filed on Jul. 8, 2010, now Pat. No. 8,609,099, which is a continuation of application No. 11/741,189, filed on Apr. 27, 2007, now Pat. No. 7,790,163, which is a continuation-in-part of application No. 11/684,907, filed on Mar. 12, 2007, now abandoned.

(60) Provisional application No. 60/781,121, filed on Mar. 10, 2006, provisional application No. 60/828,271, filed on Oct. 5, 2006, provisional application No. 60/862,501, filed on Oct. 23, 2006.

(51) Int. Cl.

| | | |
|---|---|---|
| *A61K 39/395* | (2006.01) | |
| *C07K 16/24* | (2006.01) | |
| *G01N 33/68* | (2006.01) | |
| *C07K 16/46* | (2006.01) | |
| *A61K 39/00* | (2006.01) | |

(52) U.S. Cl.
CPC .......... *C07K 16/244* (2013.01); *C07K 16/468* (2013.01); *G01N 33/6869* (2013.01); *A61K 2039/505* (2013.01); *C07K 2317/24* (2013.01); *C07K 2317/31* (2013.01); *C07K 2317/33* (2013.01); *C07K 2317/52* (2013.01); *C07K 2317/76* (2013.01); *C07K 2317/92* (2013.01); *C07K 2319/30* (2013.01); *G01N 2333/54* (2013.01); *Y10S 530/809* (2013.01)

(58) Field of Classification Search
None
See application file for complete search history.

(56) References Cited

U.S. PATENT DOCUMENTS

| | | | |
|---|---|---|---|
| 4,946,778 | A | 8/1990 | Ladner et al. |
| 6,063,372 | A | 5/2000 | Banchereau et al. |
| 6,274,711 | B1 | 8/2001 | Golstein et al. |
| 7,790,163 | B2 | 9/2010 | Jaspers et al. |
| 7,910,540 | B2 | 3/2011 | Levin et al. |
| 7,910,703 | B2 | 3/2011 | Lewis et al. |
| 8,333,968 | B2 | 12/2012 | Lewis et al. |
| 8,496,936 | B2 | 7/2013 | Lewis et al. |
| 8,557,544 | B2 | 10/2013 | Jaspers et al. |
| 8,609,099 | B2 | 12/2013 | Jaspers et al. |
| 8,992,922 | B2 | 3/2015 | Lewis et al. |
| 2007/0218065 | A1 | 9/2007 | Jaspers et al. |
| 2008/0044423 | A1 | 2/2008 | Cochrane et al. |
| 2010/0310565 | A1 | 12/2010 | Jaspers et al. |
| 2011/0318350 | A1 | 12/2011 | Jaspers et al. |
| 2012/0177653 | A1 | 7/2012 | Jaspers et al. |
| 2012/0294862 | A1 | 11/2012 | Lewis et al. |
| 2012/0329093 | A1 | 12/2012 | Jaspers et al. |
| 2013/0315911 | A1 | 11/2013 | Stevens et al. |

FOREIGN PATENT DOCUMENTS

| | | |
|---|---|---|
| EP | 1 687 026 | 5/2008 |
| WO | WO 95/18826 | 7/1995 |
| WO | WO 97/04097 | 2/1997 |
| WO | WO 97/15320 | 5/1997 |
| WO | WO 2005/010044 | 2/2005 |
| WO | WO 2006/054059 | 5/2006 |
| WO | WO 2006/088833 | 8/2006 |
| WO | WO 2007/070750 | 6/2007 |
| WO | WO 2008/021156 | 2/2008 |
| WO | WO 2008/047134 | 4/2008 |

(Continued)

OTHER PUBLICATIONS

Agarwal et al., "Interleukin-23 promotes a distinct CD4 T cell activation state characterized by the production of interleukin-17," *J. Biol. Chem.* 278:1910-191, 2003.
"Anti-human IL-17 Antibody" Internet Citation (Online) Aug. 28, 2007 XP002474646 Retrieved from the Internet: URL:http://www.rndsystems.com/pdf/af317na.pdf>.
Antonysamy et al., "Evidence for a role of IL-17 in organ allograft rejection: IL-17 promotes the functional differentiation of dendritic cell progenitors," *J. Immunol.* 162(1):577-584, 1999.
Attur et al., "Interleukin-17 up-regulation of nitric oxide production in human osteoarthritis cartilage," *Arthritis Rheum.* 40(6):1050-1053, 1997.
Attur et al., "Osteopontin: an intrinsic inhibitor of inflammation in cartilage," *Arthritis Rheum.* 44:578-584, 2001.
Barczyk et al, "Interleukin-17 in sputum correlates with airway hyperresponsiveness to methacholine," *Respir. Med.* 97(6):726-733, 2003.

(Continued)

*Primary Examiner* — Dong Jiang
(74) *Attorney, Agent, or Firm* — Brian J. Walsh

(57) ABSTRACT

The present invention relates to blocking, inhibiting, reducing, antagonizing or neutralizing the activity of IL-17A and IL-17F. IL-17A and IL-17F are cytokines that are involved in inflammatory processes and human disease. The present invention includes antibodies that bind both IL-17A and IL-17F, hybridomas that produce the antibodies, and methods of using the same in inflammation.

3 Claims, 1 Drawing Sheet

(56) References Cited

FOREIGN PATENT DOCUMENTS

| WO | WO 2008/133684 | 11/2008 |
|---|---|---|
| WO | WO 2013/177101 | 11/2013 |

OTHER PUBLICATIONS

Bird, "Single-chain antigen-binding proteins," *Science* 242:423-426, 1988.
Bowcock et al., "Getting under the skin: the immunogenetics of psoriasis," *Nat. Rev. Immunol.* 5(9):699-711, 2005.
Cai et al., "Pathways by which interleukin 17 induces articular cartilage breakdown in vitro and in vivo," *Cytokine* 16:10-21, 2001.
Chabaud et al., "Human Interleukin-17: a T cell-derived proinflammatory cytokine produced by the rheumatoid synovium," *Arthritis Rheum.* 42: 963-970, 1999.
Chaouat et al., "PCR and Microarrays to study implantation in mice and human," Abstract O 16-1, *Tissue Antigens* 64(4):355, 2004.
Dudler et al., "Effect of interleukin 17 on proteoglycan degradation in murine knee joints," *Ann. Rheum. Dis.* 59(7):529-532, 2000.
Dumont, F.J., "IL-17 cytokine / receptor families: emerging targets for the modulation of inflammatory responses," *Expert Opinion Therapeutic Patents*, 13(3):287-303, 2003.
Fieschi et al., "A novel form of complete IL-12/IL-23 receptor beta1 deficiency with cell surface-expressed nonfunctional receptors," *Blood* 104(7):2095-2101, 2004.
Fossiez et al., "T cell interleukin-17 induces stromal cells to produce proinflammatory and hematopoietic cytokines," *J. Exp. Med.* 183:2593-2603, 1996.
Fujino et al., "Increased expression of interleukin 17 in inflammatory bowel disease," *Gut* 52(1):65-70, 2003.
Gaffen, S L., "Biology of recently discovered cytokines: interleukin-17—a unique inflammatory cytokine with roles in bone biology and arthritis," *Arthritis Res. Ther.* 6(6):240-247, 2004.
Gaffen et al., "The IL-17 cytokine family," *Vitam. Horm.* 74:255-282, 2006.
Harrington et al., "Expanding the effector CD4 T-cell repertoire: the Th17 lineage," *Curr. Opin. Immunol.* 18(3):349-56, 2006.
Hellings et al., "interleukin-17 orchestrates the granulocyte influx into airways after allergen inhalation in a mouse model of allergic asthma," *Am. J. Respir. Cell Mol. Biol.* 28:42-50, 2003.
Hofstetter et al, "Therapeutic efficacy of IL-17 neutralization in murine experimental autoimmune encephalomyelitis," *Cell. Immunol.* 237(2):123-130, 2005.
Honorati et al., "Contribution of interleukin 17 to human cartilage degradation and synovial inflammation in osteoarthritis," *Osteoarthritis Cartilage* 10(10):799-807, 2002.
Honorati et al., "High in vivo expression of interleukin-17 receptor in synovial endothelial cells and chondrocytes from arthritis patients," *Rheumatology (Oxford)* 40(5):522-527, 2001.
Hurst et al., "New IL-17 family members promote TH1 or Th2 responses in the lung: in vivo function of the novel cytokine IL-25," *J. Immunol.* 169:443-453, 2002.
Huston et al., "Protein engineering of antibody binding sites: recovery of specific activity in an anti-digoxin single-chain Fv analogue produced in *Escherichia coli*," *Proc. Natl. Acad. Sci. USA* 85:5879-5883, 1988.
Hwang et al., "Expression of IL-17 homologs and their receptors in the synovial cells of rheumatoid arthritis patients," *Mol. Cells* 19(2):180-184, 2005.
Hymowitz et al., "IL-17s adopt a cystine knot fold: structure and activity of a novel cytokine, IL-17F, and implications for receptor binding," *EMBO J.* 20(19):5332-5341, 2001.
Ishigame et al., "The Roles of Interleukin (IL)-17A and IL-17F in the Development of Inflammatory Responses," *Cytokine* Abstract 62, p. 17, 2007.
Johnson et al., "Interleukin-11 and IL-17 and the pathogenesis of periodontal disease," *J. Periodontol.* 75(1):37-43, 2004.
Jones et al., "Interleukin-17 stimulates the expression of interleukin-8, growth-related oncogene-alpha, and granulocyte-colony-stimulating factor by human airway epithelial cells," *Am. J. Respir. Cell. Mol. Biol.* 26(6):748-753, 2002.
Jovcic et al., "In vivo effects of interleukin-17 on haematopoietic cells and cytokine release in normal mice," *Cell Prolif.* 37(6):401-412, 2004.
Katz et al., "Interleukin-17 enhances tumor necrosis factor alpha-induced synthesis of interleukins 1,6, and 8 in skin and synovial fibroblasts: a possible role as a "fine-tuning cytokine" in inflammation processes," *Arthritis Rheum.* 44(9):2176-2184, 2001.
Kawaguchi et al., "Identification of a novel cytokine, ML-1, and its expression in subjects with asthma," *J. Immunol.* 167:4430-4435, 2001.
Kawaguchi et al., "IL-17 cytokine family," *J. Allergy Clin. Immunol.* 114:1265-1273, 2004.
Kawaguchi et al., "The IL-17F signaling pathway is involved in the induction of IFN-γ-inducible protein 10 in bronchial epithelial cells," *J. Allergy Clin. Immunol.* 119:1408-1414, 2007.
Kehlen et al., "Expression, modulation and signalling of IL-17 receptor in fibroblast-like synoviocytes of patients with rheumatoid arthritis," *Clin. Exp. Immunol.* 127(3):539-546, 2002.
Kelly et al., "Interleukin-17/interleukin-17 receptor-mediated signaling is important for generation of an optimal polymorphonuclear response against Toxoplasma gondii infection," *Infect. Immun.* 73(1):617-621, 2005.
Khader et al., "IL-23 and IL-17 in the establishment of protective pulmonary CD4(+) T cell responses after vaccination and during *Mycobacterium tuberculosis* challenge," *Nature Immunology* 8:369-377, 2007.
Kikly et al., "The IL-23/Th17 axis: therapeutic targets for autoimmune inflammation," *Current Opinion in Immunology* 18(6):670-675, 2006.
Kim et al., "Increased interleukin-17 production via a phosphoinositide 3-kinase/Akt and nuclear factor kappaB-dependent pathway in patients with rheumatoid arthritis," *Arthritis Res. Ther.*7(1):R139-R148, 2005.
Koenders et al., "Interleukin-17 acts independently of TNF-alpha under arthritic conditions," *J. Immunol.* 176(10):6262-6269, 2006.
Koenders et al., "Interleukin-17 receptor deficiency results in impaired synovial expression of interleukin-1 and matrix metalloproteinases 3, 9, and 13 and prevents cartilage destruction during chronic reactivated streptococcal cell wall-induced arthritis," *Arthritis Rheum.* 52(10):3239-3247, 2005.
Kolls et al., "Interleukin-17 family members and inflammation," *Immunity* 21:467-476, 2004.
Komiyama et al., "IL-17 plays an important role in the development of experimental autoimmune encephalomyelitis," *J. Immunol.* 177(1):566-73, 2006.
Koshy et al., "Interleukin 17 induces cartilage collagen breakdown: novel synergistic effects in combination with proinflammatory cytokines," *Ann. Rheum. Dis.* 61(8):704-13, 2002.
Kotake et al., "IL-17 in synovial fluids from patients with rheumatoid arthritis is a potent stimulator of osteoclastogenesis," *J. Clin. Invest.* 103:1345-1352, 1999.
Kotake et al., "The Role of IL-17 in Joint Destruction," *Drug News Perspect.* 15(1):17-23, 2002.
Kurasawa et al., "Increased interleukin-17 production in patients with systemic sclerosis," *Arthritis Rheum.* 43(11):2455-2463, 2000.
Laan et al., "A role of GM-CSF in the accumulation of neutrophils in the airways caused by IL-17 and TNF-α," *Eur. Respir. J.* 21:387-393, 2003.
Langrish et al., "IL-12 and IL-23: master regulators of innate and adaptive immunity," *Immunol. Rev.* 202:96-105, 2004.
Langrish et al., "IL-23 drives a pathogenic T cell population that induces autoimmune inflammation," *J. Exp. Med.* 201:233-240, 2005.
Li et al., "The expression of interleukin-17, interferon-gamma, and macrophage inflammatory protein-3 alpha mRNA in patients with psoriasis vulgaris," *J. Huazhong Univ. Sci. Technolog. Med. Sci.* 24(3):294-296, 2004.
Linden et al., "Airway neutrophils and interleukin-17," *Eur. Respir. J.* 15:973-977, 2000.

(56) References Cited

OTHER PUBLICATIONS

Linden et al., "Role of Interleukin-17 and the Neutrophil in asthma," *Int. Arch. Allergy Immunol.* 126:179-184, 2001.
Lock et al., "Gene-microarray analysis of multiple sclerosis lesions yields new targets validated in autoimmune encephalomyelitis," *Nat. Med.* 8(5):500-508, 2002.
Lubberts, E., "The role of IL-17 and family members in the pathogenesis of arthritis," *Curr. Opin. Investig. Drugs* 4(5):572-577, 2003.
Lubberts et al., "IL-1-independent role of IL-17 in synovial inflammation and joint destruction during collagen-induced arthritis," *J. Immunol.* 167(2):1004-1013, 2001.
Lubberts et al., "IL-17 promotes bone erosion in murine collagen-induced arthritis through loss of the receptor activator of NF-kappa B ligand/osteoprotegerin balance," *J. Immunol.* 170(5):2655-2662, 2003.
Lubberts et al., "Reduction of interleukin-17-induced inhibition of chondrocyte proteoglycan synthesis in intact murine articular cartilage by interleukin-4," *Arthritis Rheum.* 43(6):1300-1306, 2000.
Lubberts et al., "The role of T-cell interleukin-17 in conducting destructive arthritis: lessons from animal models," *Arthritis Res. Ther.*7(1):29-37, 2005.
Lubberts et al., "Treatment with a neutralizing anti-murine interleukin-17 antibody after the onset of collagen-induced arthritis reduces joint inflammation, cartilage destruction, and bone erosion," *Arthritis Rheum.* 50(2):650-9, 2004.
Luger et al., "Essential Role for IL-23 but not for the Th17 Effector Response in Pathogenesis of Experimental Ocular Autoimmunity," Abstract 93, *Cytokine* p. 26, 2007.
Maertzdorf et al., "IL-17 expression in human herpetic stromal keratitis: modulatory effects on chemokine production by corneal fibroblasts," *J. Immunol.* 169(10):5897-5903, 2002.
Matusevicius et al., "Interleukin-17 mRNA expression in blood and CSF mononuclear cells is augmented in multiple sclerosis," *Mult. Scler.* 5:101-104, 1999.
McAllister et al., "IL-17A and IL-17F Signaling and Pro-Inflammatory Responses in Human Bronchial Epithelial Cells," *International Conference American Thoracic Society*, Abstract A38, A109, 2005.
McGeachy et al., "Cytokines in the induction and resolution of experimental autoimmune encephalomyelitis," *Cytokine* 32(2):81-84, 2005.
Mensah-Brown et al., "IL-23 leads to diabetes induction after subdiabetogenic treatment with multiple low doses of streptozotocin," *Eur. J. Immunol.* 36(1):216-223, 2006.
Miljkovic et al., "Inducible nitric oxide synthase activation by interleukin-17," *Cytokine Growth Factor Rev.* 15(1):21-32, 2004.
Miyamoto et al., "Endogenous IL-17 as a mediator of neutrophil recruitment caused by endotoxin exposure in mouse airways," *J. Immunol.* 170(9):4665-4672, 2003.
Molet et al., "IL-17 is increased in asthmatic airways and induces human bronchial fibroblasts to produce cytokines," *J. Allergy Clin. Immunol.* 108:430-438, 2001.
"Monoclonal Anti-human IL-31 Antibody" Apr. 18, 2006 (Apr. 18, 2006), R&D Systems, Inc., XP002461764 ISBN: 1-800-343-7475. Retrieved from the Internet: URL:http://www.mdsystems.com/pdf/MAB2824.pdf>.
Moseley et al., "Interleukin-17 family and IL-17 receptors," *Cytokine Growth Factor Rev* 14:155-174, 2003.
Nakae et al., "IL-17 production from activated T cells is required for the spontaneous development of destructive arthritis in mice deficient in IL-1 receptor antagonist," *Proc. Natl. Acad. Sci. USA* 100(10):5986-5990, 2003.
Nakajima et al., "Role of cytokines in allergic airway inflammation," *Int Arch. Allergy Immunol.* 142(4):265-73, 2007.
Napolitani et al., "Selected Toll-like receptor agonist combinations synergistically trigger a T helper type 1-polarizing program in dendritic cells," *Nat. Immunol.* 6(8):769-776, 2005.

Numasaki et al., "IL-17 and IL-17F modulate GM-CSF production by lung microvascular endothelial cells stimulated with IL-1beta and/or TNF-alpha," *Immunol. Lett.* 95(2):175-184, 2004.
Numasaki et al., "Regulatory roles of IL-17 and IL-17F in G-CSF production by lung microvascular endothelial cells stimulated with IL-1beta and/or TNF-alpha," *Immunol. Lett.* 95(1):97-104, 2004.
Oda et al., "Interleukin-17F induces pulmonary neutrophilia and amplifies antigen-induced allergic response," *Am. J. Respir. Crit. Care Med.* 171:12-18, 2005.
Pacquelet et al., "Interleukin 17, a nitric oxide-producing cytokine with a peroxynitrite-independent inhibitory effect on proteoglycan synthesis," *J. Rheumatol.* 29(12):2602-10, 2002.
Pelidou et al., "Enhancement of acute phase and inhibition of chronic phase of experimental autoimmune neuritis in Lewis rats by intranasal administration of recombinant mouse interleukin 17: potential immunoregulatory role," *Exp. Neurol.* 163(1):165-172, 2000.
Rahman et al., "IL-17R activation of human airway smooth muscle cells induces CXCL-8 production via a transcriptional-dependent mechanism," *Clin. Immunol.* 115(3):268-276, 2005.
Ramsey et al., "Polymorphisms in the interleukin 17F gene (IL17F) and asthma," *Genes Immun.* 6(3):236-241, 2005.
Ruddy et al., "Interleukin-17 regulates expression of the CXC chemokine LIX/CXCL5 in osteoblasts: implications for inflammation and neutrophil recruitment," *J. Leukoc. Biol.* 76(1):135-144, 2004.
Rutitzky, Laura I. et al., "Severe CD4 T Cell-Mediated Immunopathology in Murine Schistosomiasis Is Dependent on IL-12p40 and Correlates with High Levels of IL-17", Journal of Immunology, vol. 175 (6), pp. 3920-3926, Sep. 15, 2005.
Sato et al., "Th17 functions as an osteoclastogenic helper T cell subset that links T cell activation and bone destruction," *J. Exp. Med.* 203(12):2673-2682, 2006.
Schnyder-Candrian et al., "Interleukin-17 is a negative regulator of established allergic asthma," *J. Exp. Med.* 203(12):2715-25, 2006.
Sebkova et al., "Extracellular signal-regulated protein kinase mediates interleukin 17 (IL-17)-induced IL-8 secretion in Helicobacter pylori-infected human gastric epithelial cells," *Infect. Immun.* 72(9):5019-5026, 2004.
Sonderegger et al., "Neutralization of IL-17 by active vaccination inhibits IL-23-dependent autoimmune myocarditis," *Eur. J. Immunol.* 36(11):2849-2856, 2006.
Spriggs, M.K., "Interleukin-17 and its receptor" *J. Clin. Immunol.* 17:366-369, 1997.
Starnes et al., "Cutting edge: IL-17F, a novel cytokine selectively expressed in activated T cells and monocytes, regulates angiogenesis and endothelial cell cytokine production," *J. Immunol.* 167:4137-4140, 2001.
Stumhofer et al., "Interleukin 27 negatively regulates the development of interleukin 17-producing T helper cells during chronic inflammation of the central nervous system," *Nat. Immunol.* 7(9):937-945, 2006.
Tato et al., "Immunology: what does it mean to be just 17?" *Nature* 441(7090):166-168, 2006.
Toichi et al., "An anti-IL-12p40 antibody down-regulates type 1 cytokines, chemokines, and IL-12/IL-23 in psoriasis," *J. Immunol.* 177(7):4917-4926, 2006.
Uyttenhove et al., "Development of an anti-IL-17A auto-vaccine that prevents experimental auto-immune encephalomyelitis," *Eur. J. Immunol.* 36(11):2868-74, 2006.
Van Bezooijen et al., "Interleukin-17: a new bone acting cytokine in vitro," *J. Bone Miner. Res.* 14:1513-1521, 1999.
Villarino et al., "IL-27 limits IL-2 production during Th1 differentiation," *J. Immunol.* 176(1):237-247, 2006.
Ward et al., "Binding Activities of a repertoire of single immunoglobulin variable domains secreted from *Escherichia coli,*" *Nature* 341:544-546, 1989.
Wells, A.F., "Anticytokine therapies in rheumatoid arthritis: from the pipette to the patient," *Drug Discovery Today: Therapeutic Strategies* 1(3):293-297, 2004.
Williman et al., "The use of Th1 cytokines, IL-12 and IL-23, to modulate the immune response raised to a DNA vaccine delivered by gene gun," *Vaccine* 24(21):4471-4474, 2006.

(56) References Cited

OTHER PUBLICATIONS

Witowski et al., "IL-17 stimulates intraperitoneal neutrophil infiltration through the release of GRO alpha chemokine from mesothelial cells," *J. Immunol.* 165(10):5814-5821, 2000.

Witowski et al., "Interleukin-17: a mediator of inflammatory responses," *Cell. Mol. Life Sci.* 61(5):567-579, 2004.

Wong et al, "Elevation of proinflammatory cytokine (IL-18, IL-17, IL-12) and Th2 cytokine (IL-4) concentrations in patients with systemic lupus erythematosus," *Lupus* 9(8):589-593, 2000.

Wright, Jill F. et al., "Identification of an Interleukin 17F/17A Heterodimer in Activated Human CD4+ T Cells", Journal of Biological Chemistry, vol. 282 (18), pp. 13447-13455, May 4, 2007.

Yao et al., "Herpesvirus Saimiri encodes a new cytokine, IL-17, which binds to a novel cytokine receptor," *Immunity* 3:811-821, 1995.

Yao et al., "Human IL-17: A novel cytokine derived from T cells," *J. Immunol.* 155:5483-5486, 1995.

Ye et al., "Interleukin-17 and lung host defense against *Klebsiella pneumoniae* infection," *Am. J. Respir. Cell. Mol. Biol.* 25(3):335-340, 2001.

Yen et al., "IL-23 is essential for T cell-mediated colitis and promotes inflammation via IL-17 and IL-6," *J. Clin. Invest.* 116(5):1310-1316, 2006.

Zhang et al, "Critical role of IL-17 receptor signaling in acute TNBS-induced colitis," *Inflamm. Bowel Dis.* 12(5):382-388, 2006.

Bristol-Myers Squibb Company, International Patent Application No. PCT/US2013/041928, filed May 21, 2013.

Stevens et al., U.S. Appl. No. 13/898,544, filed May 21, 2013.

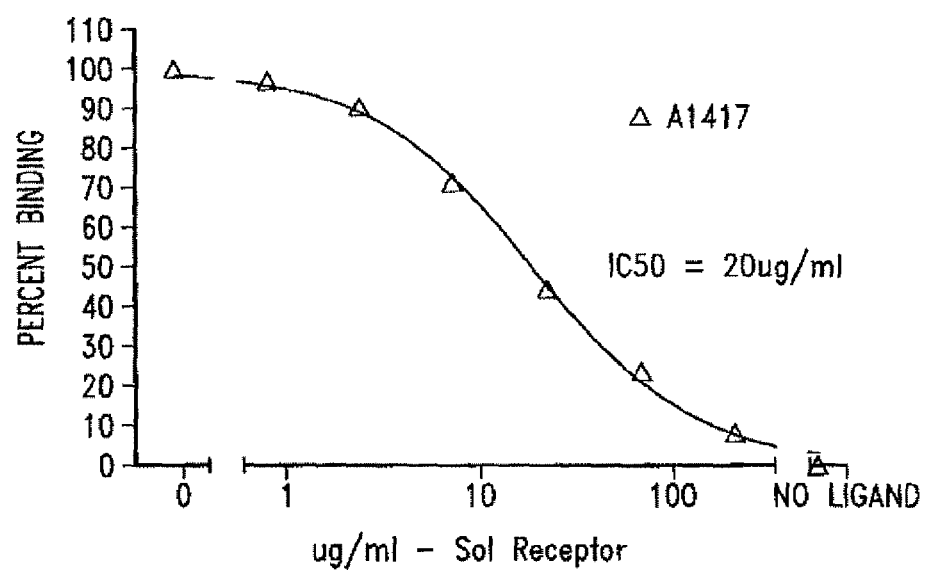

MONOCLONAL ANTIBODIES THAT BIND BOTH IL-17A AND IL-17F

CROSS-REFERENCE TO RELATED APPLICATIONS

The present application is a divisional of U.S. patent application Ser. No. 14/493,389, filed Sep. 23, 2014, now U.S. Pat. No. 9,416,183, which is a divisional of U.S. patent application Ser. No. 13/910,311, filed Jun. 5, 2013, now U.S. Pat. No. 8,871,467, which is a continuation of U.S. patent application Ser. No. 13/539,534, filed Jul. 2, 2012, now U.S. Pat. No. 8,557,544, which is a divisional of U.S. patent application Ser. No. 12/832,311, filed Jul. 8, 2010, which is a continuation of U.S. patent application Ser. No. 11/741,189, filed Apr. 27, 2007, now U.S. Pat. No. 7,790,163, which is a continuation-in-part of U.S. patent application Ser. No. 11/684,907, filed Mar. 12, 2007, now abandoned, which claims the benefit of U.S. Patent Application Ser. No. 60/781,121, filed Mar. 10, 2006, U.S. Patent Application Ser. No. 60/828,271, filed Oct. 5, 2006, and U.S. Patent Application Ser. No. 60/862,501, filed Oct. 23, 2006, all of which are herein incorporated by reference in their entirety.

FIELD OF THE INVENTION

The present invention relates generally to the identification and isolation of antibodies that bind to both IL-17A and Il-17F and methods of using the same.

BACKGROUND OF THE INVENTION

Six members of the IL-17 family have been identified based on their similarity to the prototypical member of the family, originally identified as IL-17 and which is now designated IL-17A. See e.g. Spriggs, M. K. "Interleukin-17 and its receptor" *J. Clin. Immunol.* 17:366-369 (1997). The other members of the family are IL-17B, IL-17C, IL-17D, IL-17E (also known as IL-25), and IL-17F. See e.g. Kawaguchi et al. "IL-17 cytokine family", *J. Allergy Clin. Immunol.* 114: 1265-1273 (2004); Kolls and Linden, "Interleukin-17 family members and inflammation", *Immunity* 21:467-476 (2004) and Moseley et al., "Interleukin-17 family and IL-17 receptors", *Cytokine Growth Factor Rev* 14:155-174 (2003). Among the members of the family, IL-17A and IL-17F are by far the most similar to one another sharing 55% identity (Kolls and Linden, 2004). In addition to their sequence similarity, both of these cytokines seem are produced by similar cell types, most notably activated, memory CD4+ T cells. See e.g. Agarwal et al., "Interleukin-23 promotes a distinct CD4 T cell activation state characterized by the production of interleukin-17" *J. Biol. Chem.* 278: 1910-191 (2003); see also Langrish et al. "IL-23 drives a pathogenic T cell population that induces autoimmune inflammation" *J. Exp. Med.* 201: 233-240 (2005); and Starnes et al. "Cutting edge: IL-17F, a novel cytokine selectively expressed in activated T cells and monocytes, regulates angiogenesis and endothelial cell cytokine production" *J. Immunol.* 167:4137-4140 (2001).

Moreover, both have been similarly implicated as contributing agents to progression and pathology of a variety of inflammatory and auto-immune diseases in humans and in mouse models of human diseases. Specifically, IL-17A and IL-17F have been implicated as major effector cytokines that trigger inflammatory responses and thereby contribute to a number of autoinflammatory diseases including multiple sclerosis, rheumatoid arthritis, and inflammatory bowel diseases.

The demonstrated in vivo activities of both IL-17A and IL-17F illustrate the clinical or therapeutic potential of, and need for, IL-17A and IL-17F antagonists. Specifically, antibodies that bound to both IL-17A and IL-17F that inhibit (antagonist antibodies) the immunological activities of both IL-17A and Il-17F would possess such novel therapeutic qualities. Thus, there remains a need in the art for an antagonist to both IL-17A and IL-17F.

BRIEF DESCRIPTION OF THE DRAWINGS

FIGURE shows a representative binding curve generated by the Prizm software program.

DETAILED DESCRIPTION OF THE INVENTION

The pro-inflammatory cytokines IL-17A and IL-17F have a high degree of sequence similarity, share many biological properties, and are both produced by activated T cells. They have both been implicated as factors that contribute to the progression of various autoimmune and inflammatory diseases including rheumatoid arthritis and asthma. In fact, reagents that negate IL-17A function significantly ameliorate disease incidence and severity in several mouse models of human disease. IL-17A mediates its effects through interaction with its cognate receptor, the IL-17 receptor (IL-17RA), and for IL-17F, IL-17RA. Thus, the present invention has determined that a cross-reactive antibody may be useful as an antagonist to both IL-17A and IL-17F, and thus to block both IL-17A and IL-17F. Accordingly, the present invention addresses this need by providing therapeutic molecules (e.g. antibodies) which may block, inhibit, reduce, antagonize or neutralize the activity of both IL-17A (polynucleotide sequence is shown as SEQ ID NO:1 and the encoded polypeptide is shown as SEQ ID NO:2) and IL-17F (polynucleotide sequence is shown as SEQ ID NO:3 and the encoded polypeptide is shown as SEQ ID NO:4). Thus, the present invention is directed to IL-17A and IL-17F antagonists, such as the antibodies described herein. The invention further provides uses therefor in inflammatory disease, as well as related compositions and methods.

A) Overview

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), irritable bowel syndrome (IBS), psoriasis, and asthma), non-immune-mediated inflammatory diseases, infectious diseases, immunodeficiency diseases, neoplasia, etc.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

A central event in both humoral and cell mediated immune responses is the activation and clonal expansion of helper T cells. Helper T cell activation is initiated by the interaction of the T cell receptor (TCR)—CD3 complex with an antigen-MHC on the surface of an antigen presenting cell. This interaction mediates a cascade of biochemical events that induce the resting helper T cell to enter a cell cycle (the G0 to G1 transition) and results in the expression of a high affinity receptor for IL-2 and sometimes IL-4. The activated T cell progresses through the cycle proliferating and differentiating into memory cells or effector cells.

In addition to the signals mediated through the TCR, activation of T cells involves additional costimulation induced by cytokines released by the antigen presenting cell or through interactions with membrane bound molecules on the antigen presenting cell and the T cell. The cytokines IL-1 and IL-6 have been shown to provide a costimulatory signal. Also, the interaction between the B7 molecule expressed on the surface of an antigen presenting cell and CD28 and CTLA-4 molecules expressed on the T cell surface effect T cell activation. Activated T cells express an increased number of cellular adhesion molecules, such as ICAM-1, integrins, VLA-4, LFA-1, CD56, etc.

T-cell proliferation in a mixed lymphocyte culture or mixed lymphocyte reaction (MLR) is an established indication of the ability of a compound to stimulate the immune system. In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Immune related diseases could be treated by suppressing the immune response. Using soluble receptors and/or neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

Interleukin-17 (IL-17A) has been identified as a cellular ortholog of a protein encoded by the T lymphotropic Herpes virus Saimiri (HSV) [see, Rouvier et al., J. Immunol., 150(12): 5445-5456 (19993); Yao et al., J. Immunol., 122 (12):5483-5486 (1995) and Yao et al., Immunity, 3(6):811-821 (1995)]. Subsequent characterization has shown that this protein is a potent cytokine that acts to induce proinflammatory responses in a wide variety of peripheral tissues. IL-17A is a disulfide-linked homodimeric cytokine of about 32 kDa which is synthesized and secreted only by CD4+ activated memory T cells (reviewed in Fossiez et al., Int. Rev. Immunol., 16: 541-551 [1998]). Specifically, IL-17 is synthesized as a precursor polypeptide of 155 amino acids with an N-terminal signal sequence of 19-23 residues and is secreted as a disulfide-linked homodimeric glycoprotein. Il-17A is disclosed in WO9518826 (1995), WO9715320 (1997) and WO9704097 (1997), as well as U.S. Pat. No. 6,063,372.

Despite its restricted tissue distribution, IL-17A exhibits pleitropic biological activities on various types of cells. IL-17A has been found to stimulate the production of many cytokines. It induces the secretion of IL-6, IL-8, IL-12, leukemia inhibitory factor (LIF), prostaglandin E2, MCP-1 and G-CSF by adherent cells like fibroblasts, keratinocytes, epithelial and endothelial cells. IL-17A also has the ability to induce ICAM-1 surface expression, proliferation of T cells, and growth and differentiation of CD34$^+$ human progenitors into neutrophils. IL-17A has also been implicated in bone metabolism, and has been suggested to play an important role in pathological conditions characterized by the presence of activated T cells and TNF-α production such as rheumatoid arthritis and loosening of bone implants (Van Bezooijen et al., J. Bone Miner. Res. 14: 1513-1521 [1999]). Activated T cells of synovial tissue derived from rheumatoid arthritis patients were found to secrete higher amounts of IL-17A than those derived from normal individuals or osteoarthritis patients (Chabaud et al., Arthritis Rheum. 42: 963-970 [1999]). It was suggested that this proinflammatory cytokine actively contributes to synovial inflammation in rheumatoid arthritis. Apart from its proinflammatory role, IL-17A seems to contribute to the pathology of rheumatoid arthritis by yet another mechanism. For example, IL-17A has been shown to induce the expression of osteoclast differentiation factor (ODF) mRNA in osteoblasts (Kotake et al., J. Clin. Invest., 103: 1345-1352 [1999]). ODF stimulates differentiation of progenitor cells into osteoclasts, the cells involved in bone resorption.

Since the level of IL-17A is significantly increased in synovial fluid of rheumatoid arthritis patients, it appears that IL-17A induced osteoclast formation plays a crucial role in bone resorption in rheumatoid arthritis. IL-17A is also believed to play a key role in certain other autoimmune disorders such as multiple sclerosis (Matusevicius et al., Mult. Scler., 5: 101-104 [1999]). IL-17A has further been shown, by intracellular signalling, to stimulate Ca. sup.2+ influx and a reduction in [cAMP], in human macrophages (Jovanovic et al., J. Immunol., 160:3513 [1998]). Fibroblasts treated with IL-17A induce the activation of NF-.kappa.B, [Yao et al., Immunity, 3:811 (1995), Jovanovic et al., supra], while macrophages treated with it activate NF-.kappa.B and mitogen-activated protein kinases (Shalom-Barek et al., J. Biol. Chem., 273:27467 [1998]).

Additionally, IL-17A also shares sequence similarity with mammalian cytokine-like factor 7 that is involved in bone and cartilage growth. Other proteins with which IL-17A polypeptides share sequence similarity are human embryo-derived interleukin-related factor (EDIRF) and interleukin-20.

Consistent with IL-17A's wide-range of effects, the cell surface receptor for IL-17A has been found to be widely expressed in many tissues and cell types (Yao et al., Cytokine, 9:794 [1997]). While the amino acid sequence of the human IL-17A receptor (IL-17RA) (866 amino acids) predicts a protein with a single transmembrane domain and a long, 525 amino acid intracellular domain, the receptor sequence is unique and is not similar to that of any of the receptors from the cytokine/growth factor receptor family. This coupled with the lack of similarity of IL-17A itself to other known proteins indicates that IL-17A and its receptor may be part of a novel family of signalling proteins and receptors. It has been demonstrated that IL-17A activity is mediated through binding to its unique cell surface receptor, wherein previous studies have shown that contacting T cells with a soluble form of the IL-17A receptor polypeptide inhibited T cell proliferation and IL-2 production induced by PHA, concanavalin A and anti-TCR monoclonal antibody (Yao et al., J. Immunol., 155:5483-5486 [1995]). As such, there is significant interest in identifying and characterizing novel polypeptides having homology to the known cytokine receptors, specifically IL-17A receptors.

The expression pattern of IL-17F appears to be similar to that of IL-17A, such that it includes only activated CD4+ T cells and monocytes (Starnes et al. J. Immunol. 167: 4137-4140 [2001]). IL-17F has been demonstrated to induce G-CSF, IL-6, and IL-8 in fibroblasts (Hymowitz et al, EMBO J. 20:5322-5341 [2001]) and TGF-b in endothelial cells (Starnes et al. J. Immunol. 167: 4137-4140 [2001]). It has recently been reported that IL-23, a cytokine produced by dendritic cell, can mediate the production of both IL-17A and IL-17F, primarily in memory T cells (Aggarwal et al. J. Biol. Chem. 278:1910-1914 [2003]).

Moreover, over expression or upregulation of both IL-17A and IL-17F have been shown in arthritic and asthmatic individuals (reviewed in Moseley et al. Cytokine-Growth Factor Rev 14:155-174 [2003]). With regards to arthritis, these cytokines act in a manner characteristic to the cartilage and joint destruction that is associated with rheumatoid- and osteo-arthritis. For example, IL-17A and IL-17F have been demonstrated to enhance matrix degradation in articular cartilage explants via release of cartilage proteoglycan glycosaminoglycans and collagen fragments, while inhibiting the synthesis of new proteoglycans and collagens (Cai et al. Cytokine 16:10-21 [2001]; Attur et al Arthritis Rheum 44:2078-2083 [2001]).

Similar to IL-17A, overexpression of IL-17F in mice has also been shown to increase lung neutrophil recruitment and result in increased expression of Th1-associated cytokines in the lung, including IL-6, IFN-gamma, IP-10 and MIG (Starnes et al. J. Immunol. 167: 4137-4140 [2001]). IL-17F was also upregulated in T cells from allergen-challenged asthmatics (Kawaguchi et al J Immunol 167:4430-4435 [2001]), and found to induce IL-6 and IL-8 production in NHBE. In contrast to IL-17A, IL-17F appears to inhibit angiogenesis in vitro (Starnes et al. J. Immunol. 167: 4137-4140 [2001]).

IL-17F mRNA was not detected by northern blot in various human tissues but was dramatically induced upon activation of CD4+ T cells and monocytes. Id. In mice, Th2 cells and mastr cells were found to express IL-17F upon activation. See Dumont, Expert Opin. Ther. Patents 13(3) (2003). Like IL-17A, the expression of IL-17F was also found to be upregulated by IL-23 in mouse.

The IL-17 cytokine/receptor families appear to represent a unique signaling system within the cytokine network that will offer innovative approaches to the manipulation of immune and inflammatory responses. Accordingly, the present invention is directed to antibodies that bind to both IL-17A and IL-17F.

The present invention provides antibodies that bind both IL-17A and IL-17F (IL-17A/F antibodies) and methods for using IL-17A/F antibodies. The antibodies may act as antagonists or agonists, and find utility for, among other things, in vitro, in situ, or in vivo diagnosis or treatment of mammalian cells or pathological conditions associated with the presence (or absence) of IL-17A and/or IL-17F.

Preferred embodiments of the invention include antibodies, and any fragments or permutations thereof that bind to both IL-17A and IL-17F (herein refereed to interchangeably as "cross-reactive antibodies", "A/F antibodies", bispecific antibodes", "IL-17A/F antibodies" etc.). Specifically, such antibodies are capable of specifically binding to both human IL-17A and IL-17F and/or are capable of modulating biological activities associated with either or both IL-17A and IL-17F and/or their receptors, IL-17RA and IL-17RC, and thus are useful in the treatment of various diseases and pathological conditions such as immune related diseases. In more particular embodiments, there are provided antibodies which specifically bind to IL-17A (SEQ ID NO:2) and IL-17F (SEQ ID NO:4). Optionally, the antibody is a monoclonal antibody.

For example, the IL-17A/F antibodies bind to an epitope on both IL-17A and IL-17F, wherein said epitope comprises residues Ile(23), Lys (25), Gly(27), Thr (29) and Pro(34) of the following sequences of human IL-17F and the equivalent sequence found in human IL-17A shown below. Residues 23, 25, 27, 29, and 34 are predicted to be on the surface of both IL-17A and IL-17F and therefore are accessible to the binding of an antibody of the present invention or an equivalent protein binding antagonist.

```
hIL17F (Ile23-Pro34 of SEQ ID NO: 4)
IPKVGHTFFQKP hIL17A (Ile20-Pro31 of SEQ ID NO: 2)
IVKAGITIPRNP
```

Optionally, the IL-17A/F antibodies bind to another epitope on both IL-17A and IL-17F, wherein said epitope comprises residues Arg(67), Ser(68), Thr(69), Ser(70), Pro (71), Trp(72), Asn(73) of the following sequences of human IL-17F and the equivalent sequence found in human IL-17A, as shown below. Residues 69, 71 and 73 are predicted to be on the surface of the bioactive cytokine and therefore are accessible to the binding of an antibody of the present invention or equivalent protein binding antagonist.

```
hIL17F (Arg67-Asn73 of SEQ ID NO: 4)
RSTSPWN hIL17A (Arg69-Asn75 of SEQ ID NO: 2)
RSTSPWN
```

Optionally, the IL-17A/F antibodies bind to another epitope on both IL-17A and IL-17F, wherein said epitope comprises residues Asp(79), Pro(80), Asn(81), Arg(82), Tyr (83), Pro(84) and Ser(85) of the following sequences of human IL-17F and the equivalent sequence found in human IL-17A, as shown below. All residues of this epitope are predicted to be on the surface of the bioactive cytokine and therefore are accessible to the binding of an antibody of the present invention or equivalent protein binding antagonist.

```
    hIL-17F (Asp79-Ser85 of SEQ ID NO: 4)
    DPNRYPS hIL-17A (Asp81-Ser87 of SEQ ID NO: 2)
    DPERYPS
```

Optionally, the IL-17A/F antibodies bind to another epitope on both IL-17A and IL-17F, wherein said epitope comprises residues Thr(146), Pro(147), Val(148), Ile(149), His(150), His(151), Val(152) of the following sequences of human IL-17F and the corresponding sequence found in human IL-17A, as shown below. These residues are predicted to be on the surface of the bioactive cytokine and therefore to be accessible to the binding of an antibody of the present invention or equivalent protein binding antagonist.

```
    hIL-17F (Thr146-Val152 of SEQ ID NO: 4)
    TPVIHHV hIL-17A (Thr148-Val 154 of SEQ ID NO: 2)
    TPIVHHV
```

Optionally, the IL-17A/F antibodies bind to another epitope on both IL-17A and IL-17F, wherein said epitope is a discontinuous epitope comprising residues from two separate peptide chains of human IL-17F, as shown below; or the equivalent sequence found in human IL-17A, as shown below. Specifically, residues 105-109, 147-152 of hIL-17F and 107-111, 148-154 of hIL-17A are predicted to be on the surface of the bioactive cytokine and therefore are accessible to the binding of an antibody of the present invention or equivalent protein binding antagonist.

hIL-17F Sequences (Asp105-Asn109 [DISMN] and Pro147-Val152 [PVIHHV] of SEQ ID NO:4)
  hIL-17A Sequences (Asp107-Asn111 [DYHMN] and Pro149-Val154 [PIVHHV] of SEQ ID NO:2)

Optionally, the IL-17A/F antibodies bind to another epitope on both IL-17A and IL-17F, wherein said epitope is a discontinuous epitope comprising residues of two or three separate peptide chains of human IL-17F, as shown below; or the equivalent sequence found in human IL-17A. Specifically, residues 81, 82, 121, 132, 134 of hIL-17F and 83, 84, 123, 134, 136 of hIL-17A are predicted to be on the surface of the bioactive cytokine and therefore to be accessible to the binding of an antibody of the present invention or equivalent protein binding antagonist.

hIL-17F Sequences (Asp79-Ser85 [DPNRYPS] and Val119-Arg122 [VVRR] and Ser130-Glu134 [SFQLE] of SEQ ID NO:4)
  hIL-17A Sequences (Asp81-Ser87 [DPERYPS] and Val121-Arg124 [VLRR] and Ser132-Glu136 [SFRLE] of SEQ ID NO:2)

In a particular embodiment, the present invention provides bispecific antibodies that bind both IL-17A and IL-17F. Bispecific antibodies (BsAbs) are antibodies that have two different antigen binding sites, such that the antibody specifically binds to two different antigens. Antibodies having higher valencies (i.e., the ability to bind to more than two antigens) can also be prepared; they are referred to as multispecific antibodies.

The bispecific antibody preferably is a monoclonal antibody (MAb). In particular embodiments, the antibody is chimeric, or humanized, or fully human. Fully human antibodies may be generated by procedures that involve immunizing transgenic mice, wherein human immunoglobulin genes have been introduced into the mice, as discussed below. Bispecific antibodies of the invention, which bind IL-17A and IL-17F, are referred to herein as bispecific IL-17A/F antibodies or bispecific A/F MAbs.

In yet other particular embodiments, there is provided the hybridoma cell line which produces monoclonal antibodies of the present invention. In another embodiment, the IL-17A/F antibodies are linked to one or more non-proteinaceous polymers selected from the group consisting of polyethylene glycol, polypropylene glycol, and polyoxyalkylene, or to a cytotoxic agent or enzyme, or to a radioisotope, fluorescent compound or chemiluminescent compound.

Typical methods of the invention include methods to treat pathological conditions or diseases in mammals associated with or resulting from increased or enhanced IL-17A or IL-17F expression and/or activity. In the methods of treatment, IL-17A/F antibodies may be administered which preferably block or reduce the respective receptor binding or activation to their receptor(s). Optionally, the IL-17A/F antibodies employed in the methods will be capable of blocking or neutralizing the activity of both IL-17A and IL-17F, e.g., a dual antagonist which blocks or neutralizes activity of both IL-17A or IL-17F (i.e. A cross-reactive IL-17A/F antibody as described herein). The methods contemplate the use of a single, cross-reactive antibody or a combination of two or more antibodies.

The invention also provides compositions which comprise IL-17A/F antibodies. Optionally, the compositions of the invention will include pharmaceutically acceptable carriers or diluents. Preferably, the compositions will include one or more Il-17A/F antibodies in an amount which is therapeutically effective to treat a pathological condition or disease.

As such, the present invention concerns compositions and methods useful for the diagnosis and treatment of immune related disease in mammals, including humans. The present invention is based on the identification of antibodies that bind to both IL-17A and IL-17F (including agonist and antagonist antibodies) which either stimulate or inhibit the immune response in mammals Immune related diseases can be treated by suppressing or enhancing the immune response. Antibodies that enhance the immune response stimulate or potentiate the immune response to an antigen. Antibodies which stimulate the immune response can be used therapeutically where enhancement of the immune response would be beneficial. Alternatively, antibodies that suppress the immune response attenuate or reduce the immune response to an antigen (e.g., neutralizing antibodies) can be used therapeutically where attenuation of the immune response would be beneficial (e.g., inflammation).

Accordingly, antibodies that bind both IL-17A and IL-17F (also referred to herein as IL-17A/F, A/F and/or cross-reactive IL-17A and IL-17F antibodies) of the present invention and are also useful to prepare medicines and medicaments for the treatment of immune-related and inflammatory diseases, including for example, systemic lupus erythematosis, arthritis, psoriatic arthritis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, colitis, Crohn's disease gluten-sensitive enteropathy, and endotoxemia, autoimmune or immune-mediated skin diseases including bullous skin diseases, erythema multiforme and atopic and contact dermatitis, psoriasis, neutrophilic dermatoses, cystic fibrosis, allergic diseases such as asthma, allergic rhinitis, food hypersensitivity and urticaria, cystic fibrosis, immunologic diseases of the lung such as eosinophilic pneumonia, idiopathic pulmonary fibrosis, adult respiratory disease (ARD), acute respiratory distress syndrome (ARDS) and inflammatory lung injury such as asthma, chronic obstructive pulmonary disease (COPD), airway hyper-responsiveness, chronic bronchitis, allergic asthma and hypersensitivity pneumonitis, transplantation associated diseases including graft and organ rejection and graft-versus-host-disease, septic shock, multiple organ failure, cancer and angiogenesis.

In a specific aspect, such medicines and medicaments comprise a therapeutically effective amount of an IL-17A/F antibody with a pharmaceutically acceptable carrier. Preferably, the admixture is sterile.

In one aspect, the present invention concerns an isolated antibody which binds to both IL-17A and IL-17F. In another aspect, the antibody mimics the activity of both IL-17A and IL-17F (an agonist antibody) or conversely the antibody inhibits or neutralizes the activity of both IL-17A and IL-17F (an antagonist antibody). In another aspect, the antibody is a monoclonal antibody, which preferably has nonhuman complementarity determining region (CDR) residues and human framework region (FR) residues.

In a further embodiment, the invention concerns a method of identifying agonist or antagonist antibodies of Il-17A and IL-17F, said method comprising contacting both IL-17A and IL-17F with a candidate molecule and monitoring a biological activity mediated by IL-17A and/or IL-17F. In another embodiment, the invention concerns a composition of matter comprising an IL-17A/F agonist or antagonist antibody which binds both IL-17A and IL-17F in admixture with a carrier or excipient. In one aspect, the composition comprises a therapeutically effective amount of the IL-17A/F antibody. In another aspect, when the composition comprises such an agonistic IL-17A/F antibody, the composition is useful for: (a) enhancing infiltration of inflammatory cells into a tissue of a mammal in need thereof, (b) stimulating or enhancing an immune response in a mammal in need thereof, (c) increasing the proliferation of T-lymphocytes in a mammal in need thereof in response to an antigen, (d) stimulating the activity of T-lymphocytes or (e) increasing the vascul & permeability. In a further aspect, when the composition comprises such an antagonistic IL-17A/F antibody, the composition is useful for: (a) decreasing infiltration of inflammatory cells into a tissue of a mammal in need thereof, (b) inhibiting or reducing an immune response in a mammal in need thereof, (c) decreasing the activity of T-lymphocytes or (d) decreasing the proliferation of T-lymphocytes in a mammal in need thereof in response to an antigen. In another aspect, the composition comprises a further active ingredient, which may, for example, be a further antibody or a cytotoxic or chemotherapeutic agent. Preferably, the composition is sterile.

In another embodiment, the invention concerns a method of treating an immune related disorder in a mammal in need thereof, comprising administering to the mammal a therapeutically effective amount of an agonistic or antagonistic IL-17A/F antibody.

In a preferred aspect, the immune related disorder is selected form the group consisting of systemic lupus erythematosis, arthritis, psoriatic arthritis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, colitis, Crohn's disease gluten-sensitive enteropathy, and endotoxemia, autoimmune or immune-mediated skin diseases including bullous skin diseases, erythema multiforme and atopic and contact dermatitis, psoriasis, neutrophilic dermatoses, cystic fibrosis, allergic diseases such as asthma, allergic rhinitis, food hypersensitivity and urticaria, cystic fibrosis, immunologic diseases of the lung such as eosinophilic pneumonia, idiopathic pulmonary fibrosis, adult respiratory disease (ARD), acute respiratory distress syndrome (ARDS) and inflammatory lung injury such as asthma, chronic obstructive pulmonary disease (COPD), airway hyper-responsiveness, chronic bronchitis, allergic asthma and hypersensitivity pneumonitis, transplantation associated diseases including graft and organ rejection and graft-versus-host-disease, septic shock, multiple organ failure, cancer and angiogenesis.

Optionally, the antibody is a monoclonal antibody, humanized antibody, antibody fragment or single-chain antibody. In another embodiment, the invention provides an antibody which specifically binds to both IL-17A and IL-17F. The antibody may be labeled and may be immobilized on a solid support. In a further aspect, the antibody is an antibody fragment, a monoclonal antibody, a single-chain antibody, or an anti-idiotypic antibody.

In still another embodiment, the invention concerns an isolated polynucleotide that encodes a polypeptide of the present invention, wherein said polypeptide is capable of binding to both IL-17A and IL-17F.

In still another embodiment, the invention concerns an isolated polypeptide of the present invention, wherein said polypeptide is capable of binding to both IL-17A and IL-17F.

Processes for producing the same are also herein described, wherein those processes comprise culturing a host cell comprising a vector which comprises the appropriate encoding nucleic acid molecule under conditions suitable for expression of said antibody and recovering said antibody from the cell culture.

In yet another embodiment, the present invention provides a composition comprising an anti-IL-17A/F antibody in admixture with a pharmaceutically acceptable carrier. In one aspect, the composition comprises a therapeutically effective amount of the antibody. Preferably, the composition is sterile. The composition may be administered in the form of a liquid pharmaceutical formulation, which may be preserved to achieve extended storage stability. Alternatively, the antibody is a monoclonal antibody, an antibody fragment, a humanizedantibody, or a single-chain antibody.

In a further embodiment, the invention concerns an article of manufacture, comprising: (a) a composition of matter comprising an IL-17A/F antibody, or an antibody that specifically binds to both IL-17A and IL-17F; (b) a container containing said composition; and (c) a label affixed to said container, or a package insert included in said container referring to the use of said IL-17A/F antibody thereof in the treatment of an immune related disease. The composition may comprise a therapeutically effective amount of the IL-17A/F antibody.

In yet another embodiment, the present invention concerns a method of diagnosing an immune related disease in a mammal, comprising detecting the level of expression of a gene encoding either or both IL-17A and/or IL-17F (a) in a test sample of tissue cells obtained from the mammal, and (b) in a control sample of known normal tissue cells of the same cell type, wherein a higher or lower expression level in the test sample as compared to the control sample indicates the presence of immune related disease in the mammal from which the test tissue cells were obtained.

In another embodiment, the present invention concerns a method of diagnosing an immune disease in a mammal, comprising (a) contacting an IL-17A/F antibody with a test sample of tissue cells obtained from the mammal, and (b) detecting the formation of a complex between the antibody and either or both IL-17A and IL-17F in the test sample; wherein the formation of said complex is indicative of the presence or absence of said disease. The detection may be qualitative or quantitative, and may be performed in comparison with monitoring the complex formation in a control sample of known normal tissue cells of the same cell type. A larger quantity of complexes formed in the test sample indicates the presence or absence of an immune disease in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected of having a deficiency or abnormality of the immune system.

In another embodiment, the invention provides a method of diagnosing an immune-related disease in a mammal which comprises detecting the presence or absence of both IL-17A and IL-17F in a test sample of tissue cells obtained from said mammal, wherein the presence or absence of both IL-17A and IL-17F in said test sample is indicative of the presence of an immune-related disease in said mammal.

In a still further embodiment, the invention provides a method for enhancing the infiltration of inflammatory cells from the vasculature into a tissue of a mammal comprising administering to said mammal (a) an IL-17A/F agonist antibody, wherein the infiltration of inflammatory cells from the vasculature in the mammal is enhanced. In a still further embodiment, the invention provides a method for decreasing the infiltration of inflammatory cells from the vasculature into a tissue of a mammal comprising administering to said mammal an antagonist IL-17A/F antibody, wherein the infiltration of inflammatory cells from the vasculature in the mammal is decreased.

In a still further embodiment, the invention provides a method of increasing the activity of T-lymphocytes in a mammal comprising administering to said mammal an IL-17A/F agonist antibody, wherein the activity of T-lymphocytes in the mammal is increased.

In a still further embodiment, the invention provides a method of decreasing the activity of T-lymphocytes in a mammal comprising administering to said mammal an IL-17A/F antagonist antibody, wherein the activity of T-lymphocytes in the mammal is decreased.

In a still further embodiment, the invention provides a method of increasing the proliferation of T-lymphocytes in a mammal comprising administering to said mammal an IL-17A/F agonist antibody, wherein the proliferation of T-lymphocytes in the mammal is increased.

In a still further embodiment, the invention provides a method of decreasing the proliferation of T-lymphocytes in a mammal comprising administering to said mammal (a) an IL-17A/F antagonist antibody, wherein the proliferation of T-lymphocytes in the mammal is decreased.

The invention also provides articles of manufacture and kits which include one or more IL-17A/F antibodies.

The invention provides an isolated antibody or antibody fragment that binds a polypeptide, wherein the polypeptide comprises the amino acid sequence of SEQ ID NO:2 or a fragment thereof, or the amino acid sequence of SEQ ID NO:4 or a fragment thereof, and wherein the polypeptide is capable of binding the antibody produced by the hybridoma selected from: a) the hybridoma of clone designation number 339.15.5.3 (ATCC Patent Deposit Designation PTA-7987); b) the hybridoma of clone designation number 339.15.3.6 (ATCC Patent Deposit Designation PTA-7988); and c) the hybridoma of clone designation number 339.15.6.16 (ATCC Patent Deposit Designation PTA-7989). Within an embodiment, the antibody binds an epitope comprising amino acid residues 23, 25, 27, 29 and 34 of SEQ ID NO:4. Within another embodiment the antibody binds an epitope comprising amino acid residues 20, 22, 24, 26 and 31 of SEQ ID NO:2. Within another embodiment the antibody binds an epitope comprising amino acid residues 23, 25, 27, 29 and 34 of SEQ ID NO:4 or amino acid residues 20, 22, 24, 26 and 31 of SEQ ID NO:2. Within another embodiment the antibody binds an epitope comprising amino acid residues 23-34 of SEQ ID NO:4. Within another embodiment the antibody binds an epitope comprising amino acid residues 20-31 of SEQ ID NO:2. Within another embodiment the antibody binds an epitope comprising amino acid residues 67-73 of SEQ ID NO:4. Within another embodiment the antibody binds an epitope comprising amino acid residues 69-75 of SEQ ID NO:2. Within another embodiment the antibody binds an epitope comprising amino acid residues 87-93 of SEQ ID NO:4 or amino acid residues 69-75 of SEQ ID NO:2. Within another embodiment the antibody binds an epitope comprising amino acid residues 79-85 of SEQ ID NO:4. Within another embodiment the antibody binds an epitope comprising amino acid residues 81-87 of SEQ ID NO:2. Within another embodiment the antibody binds an epitope comprising amino acid residues 79-85 of SEQ ID NO:4 or amino acid residues 81-87 of SEQ ID NO:2. Within another embodiment the antibody binds an epitope comprising amino acid residues 147-152 of SEQ ID NO:4. Within another embodiment the antibody binds an epitope comprising amino acid residues 149-154 of SEQ ID NO:2. Within another embodiment the antibody binds an epitope comprising amino acid residues 147-152 of SEQ ID NO:4 or amino acid residues 149-154 of SEQ ID NO:2. Within another embodiment the antibody binds a discontinuous epitope comprising amino acid residues 105-109 and 147-152 of SEQ ID NO:4. Within another embodiment the antibody binds a discontinuous epitope comprising amino acid residues 107-111 and 148-154 of SEQ ID NO:2. Within another embodiment the antibody binds a discontinuous epitope comprising amino acid residues 105-109 and 147-152 of SEQ ID NO:4 or a discontinuous epitope comprising amino acid residues 107-111 and 148-154 of SEQ ID NO:2. Within another embodiment the antibody binds a discontinuous epitope comprising amino acid residues 79-85, 119-122 and 130-134 of SEQ ID NO:4. Within another embodiment the antibody binds a discontinuous epitope comprising amino acid residues 81-87, 121-124 and 132-136 of SEQ ID NO:2. Within another embodiment the antibody binds a discontinuous epitope comprising amino acid residues 79-85, 119-122 and 130-134 of SEQ ID NO:4 or a discontinuous epitope comprising amino acid residues 81-87, 121-124 and 132-136 of SEQ ID NO:2. Within another embodiment the antibody is suitable for parenteral, oral, intraperitoneal, intranasal, subcutaneous, aerosolized or intravenous administration in a human or animal Within another embodiment the antibody is a monoclonal antibody. Within another embodiment the monoclonal antibody is selected from the group consisting of: murine, chimeric, humanized and human monoclonal antibodies. Within another embodiment the antibody is a scFv. Within another embodiment the antibody is a bispecific antibody or a bivalent antibody. Within another embodiment the antibody is a cross-reactive monoclonal antibody which binds to a polypeptide comprising the amino acid sequence of SEQ ID NO: 2 or a fragment thereof or binds to a polypeptide comprising the amino acid sequence of SEQ ID NO: 4 or a fragment thereof.

The invention provides isolated antisera containing an antibody or antibody fragment that binds a polypeptide, wherein the polypeptide comprises the amino acid sequence of SEQ ID NO:2 or a fragment thereof, or the amino acid sequence of SEQ ID NO:4 or a fragment thereof, and wherein the polypeptide is capable of binding the antibody produced by the hybridoma selected from: a) the hybridoma of clone designation number 339.15.5.3 (ATCC Patent Deposit Designation PTA-7987); b) the hybridoma of clone designation number 339.15.3.6 (ATCC Patent Deposit Designation PTA-7988); and c) the hybridoma of clone designation number 339.15.6.16 (ATCC Patent Deposit Designation PTA-7989).

The invention provides an isolated antibody produced by a hybridoma selected from ATCC Patent Deposit Designation PTA-7987, ATCC Patent Deposit Designation PTA-7988 or ATCC Patent Deposit Designation PTA-7989, wherein the antibody reduces the pro-inflammatory activity the polypeptide comprising the amino acid sequence of SEQ ID NO:2 or a fragment thereof and the polypeptide comprising the amino acid sequence of SEQ ID NO:4 or a fragment thereof. Within an embodiment the polypeptide is capable of binding the antibody produced by the hybridoma of ATCC Patent Deposit Designation PTA-7987. Within an embodiment the polypeptide is capable of binding the antibody produced by the hybridoma of ATCC Patent Deposit Designation PTA-7988. Within an embodiment the polypeptide is capable of binding the antibody produced by the hybridoma of ATCC Patent Deposit Designation PTA-7989.

The invention provides a hybridoma of ATCC Patent Deposit Designation PTA-7987 and the antibody produced by the hybridoma. The invention provides a hybridoma of ATCC Patent Deposit Designation PTA-7988 and the antibody produced by the hybridoma. The invention provides a hybridoma of ATCC Patent Deposit Designation PTA-7989 and the antibody produced by the hybridoma.

B) Definitions

In the description that follows, a number of terms are used extensively. The following definitions are provided to facilitate understanding of the invention.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. Thus, as used herein, the term "antibody" or "antibody peptide(s)" refers to an intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')$_2$, Fv, and single-chain antibodies. "Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide-linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "isolated antibody" as used herein refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "variant" anti-IL-17A and/or IL-17F and/or IL-17A/F antibody, refers herein to a molecule which differs in amino acid sequence from a "parent" anti-IL-17A and/or IL-17F and/or IL-17A/F antibody amino acid sequence by virtue of addition, deletion and/or substitution of one or more amino acid residue(s) in the parent antibody sequence. In the preferred embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human IL-17A and/or IL-17F and preferably has properties which are superior to those of the parent antibody. For example, the variant may have a stronger binding affinity, enhanced ability to inhibit IL-17A and/or IL-17F-induced inflammation. To analyze such properties, one should compare a Fab form of the variant to a Fab form of the parent antibody or a full length form of the variant to a full length form of the parent antibody, for example, since it has been found that the format of the anti-IL-17A and/or IL-17F and/or IL-17A/F antibody impacts its activity in the biological activity assays disclosed herein. The variant antibody of particular interest herein is one which displays at least about 10 fold, preferably at least about 20 fold, and most preferably at least about 50 fold, enhancement in biological activity when compared to the parent antibody.

The term "parent antibody" as used herein refers to an antibody which is encoded by an amino acid sequence used for the preparation of the variant. Preferably, the parent antibody has a human framework region and, if present, has human antibody constant region(s). For example, the parent antibody may be a humanized or human antibody.

The term "agonist" refers to any compound including a protein, polypeptide, peptide, antibody, antibody fragment, large molecule, or small molecule (less than 10 kD), that increases the activity, activation or function of another molecule.

The term "antagonist" refers to any compound including a protein, polypeptide, peptide, antibody, antibody fragment, large molecule, or small molecule (less than 10 kD), that decreases the activity, activation or function of another molecule.

The term "bind(ing) of a polypeptide of the invention to a ligand" includes, but is not limited to, the binding of a ligand polypeptide of the present invention to a receptor; the binding of a receptor polypeptide of the present invention to a ligand; the binding of an antibody of the present invention to an antigen or epitope; the binding of an antigen or epitope of the present invention to an antibody; the binding of an antibody of the present invention to an anti-idiotypic antibody; the binding of an anti-idiotypic antibody of the present invention to a ligand; the biding of an anti-idiotypic antibody of the present invention to a receptor; the binding of an anti-anti-idiotypic antibody of the present invention to a ligand, receptor or antibody, etc.

A "bivalent antibody" other than a "multispecific" or "multifunctional" antibody, in certain embodiments, is understood to comprise binding sites having identical antigenic specificity.

A "bispecific" or "bifunctional" antibody is a hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann (1990), Clin. Exp. Immunol. 79:315-321; Kostelny et al. (1992), J. Immunol. 148:1547-1553.

The term "chimeric antibody" or "chimeric antibodies" refers to antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant domain from a human antibody, although other mammalian species may be used. Specifically, a chimeric antibody is produced by recombinant DNA technology in which all or part of the hinge and constant regions of an immunoglobulin light chain, heavy chain, or both, have been substituted for the corresponding regions from another animal's immunoglobulin light chain or heavy chain. In this way, the antigen-binding portion of the parent monoclonal antibody is grafted onto the backbone of another species' antibody. One approach, described in EP 0239400 to Winter et al. describes the substitution of one species' complementarity determining regions (CDRs) for those of another species, such as substituting the CDRs from human heavy and light chain immunoglobulin variable region domains with CDRs from mouse variable region domains. These altered antibodies may subsequently be combined with human immunoglobulin constant regions to form antibodies that are human except for the substituted murine CDRs which are specific for the antigen. Methods for grafting CDR regions of antibodies may be found, for example in Riechmann et al. (1988) Nature 332:323-327 and Verhoeyen et al. (1988) Science 239:1534-1536.

The term "effective neutralizing titer" as used herein refers to the amount of antibody which corresponds to the amount present in the serum of animals (human or cotton rat) that has been shown to be either clinically efficacious (in humans) or to reduce virus by 99% in, for example, cotton rats. The 99% reduction is defined by a specific challenge of, e.g., $10^3$ pfu, $10^4$ pfu, $10^5$ pfu, $10^6$ pfu, $10^7$ pfu, $10^8$ pfu, or $10^9$ pfu of RSV.

As used herein, the term "epitope" refers to the portion of an antigen to which a monoclonal antibody specifically binds. Thus, the term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. More specifically, the term "IL-17A epitope", "IL-17F epitope" and/or "IL-17A/F epitope" as used herein refers to a portion of the corresponding polypeptide having antigenic or immunogenic activity in an animal, preferably in a mammal, and most preferably in a mouse or a human. An epitope having immunogenic activity is a portion of an IL-17A and/or IL-17F polypeptide that elicits an antibody response in an animal. An epitope having antigenic activity is a portion of an IL-17A and/or IL-17F polypeptide to which an antibody immunospecifically binds as determined by any method well known in the art, for example, by immunoassays. Antigenic epitopes need not necessarily be immunogenic. Such epitopes can be linear in nature or can be a discontinuous epitope. Thus, as used herein, the term "conformational epitope" refers to a discontinuous epitope formed by a spatial relationship between amino acids of an antigen other than an unbroken series of amino acids. More specifically, the term epitope encompasses the epitopes as defined herein, as they apply to both IL-17A and IL-17F.

The term "epitope tagged" when used herein refers to the anti-IL-17A and/or IL-17F and/or IL-17A/F antibody fused to an "epitope tag". The epitope tag polypeptide has enough residues to provide an epitope against which an antibody can be made, yet is short enough such that it does not interfere with activity of antibodies of the present invention. The epitope tag preferably is sufficiently unique so that the antibody thereagainst does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 (Field et al. Mol. Cell. Biol. 8:2159-2165 (1988)); the c-myc tag and the 8F9, 3C7, 6E10, G4, B7 and 9E10 antibodies thereto (Evan et al., Mol. Cell. Biol. 5(12): 3610-3616 (1985)); and the Herpes Simplex virus glycoprotein D (gD) tag and its antibody (Paborsky et al., Protein Engineering 3(6):547-553 (1990)). In certain embodiments, the epitope tag is a "salvage receptor binding epitope". As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The term "fragment" as used herein refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a Il-17A or IL-17F polypeptide or an antibody that immunospecifically binds to a either Il-17A or IL-17F or both IL-17A and IL-17F polypeptide.

As used herein, the term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or 214 amino acids) are encoded by a variable region gene at the NH2-terminus (about 110 amino acids) and a kappa or lambda constant region gene at the COOH-terminus Full-length immunoglobulin "heavy chains" (about 50 Kd or 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989), Ch. 7 (incorporated by reference in its entirety for all purposes).

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain (Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196: 901-917) (both of which are incorporated herein by reference). "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

As used herein, the term "human antibody" includes and antibody that has an amino acid sequence of a human immunoglobulin and includes antibodies isolated from human immunoglobulin libraries or from animals transgenic for one or more human immunoglobulin and that do not express endogenous immunoglobulins, as described, for example, by Kucherlapati et al. in U.S. Pat. No. 5,939,598.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

In addition to antibodies, immunoglobulins may exist in a variety of other forms including, for example, single-chain or Fv, Fab, and F(ab')$_2$, as well as diabodies, linear antibodies, multivalent or multispecific hybrid antibodies (as described above and in detail in: Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986), which are incorporated herein by reference).

As used herein, the terms "single-chain Fv," "single-chain antibodies," "Fv" or "scFv" refer to antibody fragments that comprises the variable regions from both the heavy and light chains, but lacks the constant regions, but within a single polypeptide chain Generally, a single-chain antibody further comprises a polypeptide linker between the VH and VL domains which enables it to form the desired structure which would allow for antigen binding. Single chain antibodies are discussed in detail by Pluckthun in The Pharmacology of Monoclonal Antibodies, vol. 113, Rosenburg and Moore eds. Springer-Verlag, New York, pp. 269-315 (1994). Various methods of generating single chain antibodies are known, including those described in U.S. Pat. Nos. 4,694,778 and 5,260,203; International Patent Application Publication No. WO 88/01649; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041, the disclosures of which are incorporated by reference for any purpose. In specific embodiments, single-chain antibodies can also be bi-specific and/or humanized.

A "Fab fragment" is comprised of one light chain and the CH1 and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a F(ab')$_2$ molecule.

A "F(ab')$_2$ fragment" contains two light chains and two heavy chains containing a portion of the constant region between the $C_{H1}$ and $C_{H2}$ domains, such that an interchain disulfide bond is formed between two heavy chains.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993).

The term "linear antibodies" refers to the antibodies described in Zapata et al. Protein Eng. 8(10):1057-1062 (1995). Briefly, these antibodies comprise a pair of tandem Fd segments ($V_H$-$C_{H1}$-$V_H$-$C_{H1}$) which form a pair of antigen binding regions. Linear antibodies can be bispecific or monospecific.

The term "immunologically functional immunoglobulin fragment" as used herein refers to a polypeptide fragment that contains at least the variable domains of the immunoglobulin heavy and light chains. An immunologically functional immunoglobulin fragment of the invention is capable of binding to a ligand, preventing binding of the ligand to its receptor, interrupting the biological response resulting from ligand binding to the receptor, or any combination thereof. Preferably, an immunologically functional immunoglobulin fragment of the invention binds specifically to both IL-17A and IL-17F.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces IL-17RA from an expression vector. In contrast, IL-17RA can be produced by a cell that is a "natural source" of IL-17RA, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a IL-17RA polypeptide fused with a polypeptide that binds an affinity matrix. Such a fusion protein provides a means to isolate large quantities of IL-17RA using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

As used herein, the term "immunomodulator" includes cytokines, stem cell growth factors, lymphotoxins, co-stimulatory molecules, hematopoietic factors, and the like, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, Gene 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for IL-17A or IL-17F" is an oligonucleotide having a sequence (a) capable of forming a stable triplex with a portion of the IL-17A or IL-17F gene, or (b) capable of forming a stable duplex with a portion of an mRNA transcript of the IL-17A or IL-17F gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

Due to the imprecision of standard analytical methods, molecular weights and lengths of polymers are understood to be approximate values. When such a value is expressed as "about" X or "approximately" X, the stated value of X will be understood to be accurate to ±10%.

C) Antibodies that Bind IL-17a and IL-17F

The antibodies of the invention specifically bind to both IL-17A and IL17F. In some embodiments, the antibodies of the invention specifically bind a monomeric form of both IL-17A and IL-17F. In some embodiments, the antibodies of the invention bind a homodimeric form of either IL-17A or IL-17F. In still other embodiments, the antibodies of the invention specifically bind a multimeric form of IL-17A and IL-17F (e.g., a heterodimeric form). Preferred antibodies of the invention block a biological activity of both IL-17A and IL-17F.

Preferred antibodies, and antibodies suitable for use in the method of the invention, include, for example, fully human antibodies, human antibody homologs, humanized antibody homologs, chimeric antibody homologs, Fab, Fab', F(ab')$_2$ and F(v) antibody fragments, single chain antibodies, and monomers or dimers of antibody heavy or light chains or mixtures thereof. Antibodies of the invention are preferably monoclonal antibodies.

The antibodies of the invention may include intact immunoglobulins of any isotype including types IgA, IgG, IgE, IgD, IgM (as well as subtypes thereof). The antibodies preferably include intact IgG and more preferably IgG1. The light chains of the immunoglobulin may be kappa or lambda. The light chains are preferably kappa.

The antibodies of the invention include portions of intact antibodies that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like. Thus, antigen binding fragments, as well as full-length dimeric or trimeric polypeptides derived from the above-described antibodies are themselves useful.

The direct use of rodent monoclonal antibodies (MAbs) as human therapeutic agents led to human anti-rodent antibody ("HARA") (for example, human anti-mouse antibody ("HAMA")) responses which occurred in a significant number of patients treated with the rodent-derived antibody (Khazaeli, et al., (1994) Immunother. 15:42-52) Chimeric antibodies containing fewer murine amino acid sequences are believed to circumvent the problem of eliciting an immune response in humans.

Refinement of antibodies to avoid the problem of HARA responses led to the development of "humanized antibodies." Humanized antibodies are produced by recombinant DNA technology, in which at least one of the amino acids of a human immunoglobulin light or heavy chain that is not required for antigen binding has been substituted for the corresponding amino acid from a nonhuman mammalian immunoglobulin light or heavy chain. For example, if the immunoglobulin is a mouse monoclonal antibody, at least one amino acid that is not required for antigen binding is substituted using the amino acid that is present on a corresponding human antibody in that position. Without wishing to be bound by any particular theory of operation, it is believed that the "humanization" of the monoclonal antibody inhibits human immunological reactivity against the foreign immunoglobulin molecule.

As a non-limiting example, a method of performing complementarity determining region (CDR) grafting may be performed by sequencing the mouse heavy and light chains of the antibody of interest that binds to the target antigen (e.g., IL-17A and IL-17F) and genetically engineering the CDR DNA sequences and imposing these amino acid sequences to corresponding human V regions by site directed mutagenesis. Human constant region gene segments of the desired isotype are added, and the "humanized" heavy and light chain genes are co-expressed in mammalian cells to produce soluble humanized antibody. A typical expression cell is a Chinese Hamster Ovary (CHO) cell. Suitable methods for creating the chimeric antibodies may be found, for example, in Jones et al. (1986) Nature 321: 522-525; Riechmann (1988) Nature 332:323-327; Queen et al. (1989) Proc. Nat. Acad. Sci. USA 86:10029; and Orlandi et al. (1989) Proc. Natl. Acad. Sci. USA 86:3833.

Queen et al. (1989) Proc. Nat. Acad. Sci. USA 86:10029-10033 and WO 90/07861 describe the preparation of a humanized antibody Human and mouse variable framework regions were chosen for optimal protein sequence homology. The tertiary structure of the murine variable region was computer-modeled and superimposed on the homologous human framework to show optimal interaction of amino acid residues with the mouse CDRs. This led to the development of antibodies with improved binding affinity for antigen (which is typically decreased upon making CDR-grafted chimeric antibodies). Alternative approaches to making humanized antibodies are known in the art and are described, for example, in Tempest (1991) Biotechnology 9:266-271.

The antibodies of the invention may be used alone or as immunoconjugates with a cytotoxic agent. In some embodiments, the agent is a chemotherapeutic agent. In some embodiments, the agent is a radioisotope, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the agent is a toxin or cytotoxic drug, including but not limited to ricin, modified *Pseudomonas* enterotoxin A, calicheamicin, adriamycin, 5-fluorouracil, and the like. Methods of conjugation of antibodies and antibody fragments to such agents are known in the literature.

The antibodies of the invention include derivatives that are modified, e.g., by the covalent attachment of any type of molecule to the antibody such that covalent attachment does not prevent the antibody from binding to its epitope. Examples of suitable derivatives include, but are not limited to fucosylated antibodies and fragments, glycosylated antibodies and fragments, acetylated antibodies and fragments, pegylated antibodies and fragments, phosphorylated antibodies and fragments, and amidated antibodies and fragments. The antibodies and derivatives thereof of the invention may themselves by derivatized by known protecting/blocking groups, proteolytic cleavage, linkage to a cellular ligand or other proteins, and the like. In some embodiments of the invention, at least one heavy chain of the antibody is fucosylated. In some embodiments, the fucosylation is N-linked. In some preferred embodiments, at least one heavy chain of the antibody comprises a fucosylated, N-linked oligosaccharide.

The antibodies of the invention include variants having single or multiple amino acid substitutions, deletions, additions, or replacements that retain the biological properties (e.g., block the binding of IL-17A and/or IL-17F to their respective receptors, block the biological activity of IL-17A and IL-17F, binding affinity) of the antibodies of the invention. The skilled person can produce variants having single or multiple amino acid substitutions, deletions, additions or replacements. These variants may include, inter alia: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In another embodiment, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art. Antibodies of the invention also include antibody fragments. A "fragment" refers to polypeptide sequences which are preferably at least about 40, more preferably at least to about 50, more preferably at least about 60, more preferably at least about 70, more preferably at least about 80, more preferably at least about 90, and more preferably at least about 100 amino acids in length, and which retain some biological activity or immunological activity of the full-length sequence, for example, the ability to block the binding of IL-17A and/or IL-17F to their respective receptors, block the biological activity of IL-17A and IL-17F, binding affinity.

The invention also encompasses fully human antibodies such as those derived from peripheral blood mononuclear cells of ovarian, breast, renal, colorectal, lung, endometrial, or brain cancer patients. Such cells may be fused with myeloma cells, for example, to form hybridoma cells producing fully human antibodies against both IL-17A and IL-17F.

The invention also encompasses bispecific antibodies that bind to both IL-17A and IL-17F.

The antibodies of the invention are preferably nontoxic as demonstrated, for example, in in vivo toxicology studies.

The antibodies and derivatives thereof of the invention have binding affinities that include a dissociation constant ($K_a$) of less than $1 \times 10^{-2}$. In some embodiments, the $K_d$ is less than $1 \times 10^{-3}$. In other embodiments, the $K_d$ is less than $1 \times 10^{-4}$. In some embodiments, the $K_d$ is less than $1 \times 10^{-5}$. In still other embodiments, the $K_d$ is less than $1 \times 10^{-6}$. In other embodiments, the $K_d$ is less than $1 \times 10^{-7}$. In other embodiments, the $K_d$ is less than $1 \times 10^{-8}$. In other embodiments, the $K_d$ is less than $1 \times 10^{-9}$. In other embodiments, the $K_d$ is less than $1 \times 10^{-10}$. In still other embodiments, the $K_d$ is less than $1 \times 10^{-11}$. In some embodiments, the $K_d$ is less than $1 \times 10^{-12}$. In other embodiments, the $K_d$ is less than $1 \times 10^{-13}$. In other embodiments, the $K_d$ is less than $1 \times 10^{-14}$. In still other embodiments, the $K_d$ is less than $1 \times 10^{-15}$.

D) Nucleic Acids

The invention also includes nucleic acids encoding the heavy chain and/or light chain of the antibodies of the invention. Nucleic acids of the invention include nucleic acids having at least 80%, more preferably at least about 90%, more preferably at least about 95%, and most preferably at least about 98% homology to nucleic acids of the invention. The terms "percent similarity", "percent identity" and "percent homology" when referring to a particular sequence are used as set forth in the University of Wisconsin GCG software program. Nucleic acids of the invention also include complementary nucleic acids. In some instances, the sequences will be fully complementary (no mismatches) when aligned. In other instances, there may be up to about a 20% mismatch in the sequences. In some embodiments of the invention are provided nucleic acids encoding both a heavy chain and a light chain of an antibody of the invention.

Nucleic acids of the invention can be cloned into a vector, such as a plasmid, cosmid, bacmid, phage, artificial chromosome (BAC, YAC) or virus, into which another genetic sequence or element (either DNA or RNA) may be inserted so as to bring about the replication of the attached sequence or element. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. Expression vectors of the invention may further comprise regulatory sequences, for example, an internal ribosomal entry site. The expression vector can be introduced into a cell by transfection, for example.

E) Methods of Producing Antibodies to IL-17A and IL-17F

The invention also provides methods of producing monoclonal antibodies that specifically bind to both IL-17A and IL-17F. Antibodies of the invention may be produced in vivo or in vitro. One strategy for generating antibodies against both IL-17A and IL-17F involves immunizing animals with both IL-17A and IL-17F. In some embodiments, animals are immunized with the monomeric or multimeric form of FR both IL-17A and IL-17F. Animals so immunized will produce antibodies against both IL-17A and IL-17F, as well as cross-reactive antibodies against both IL-17A and IL-17F. Standard methods are known for creating monoclonal antibodies including, but are not limited to, the hybridoma technique (see Kohler & Milstein, (1975) Nature 256:495-497); the trioma technique; the human B-cell hybridoma technique (see Kozbor et al. (1983) Immunol. Today 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

Both IL-17A and IL-17F may be purified from cells or from recombinant systems using a variety of well-known techniques for isolating and purifying proteins. For example, but not by way of limitation, both IL-17A and IL-17F may be isolated based on the apparent molecular weight of the protein by running the protein on an SDS-PAGE gel and blotting the proteins onto a membrane. Thereafter, the appropriate size band corresponding to either protein may be cut from the membrane and used as an immunogen in animals directly, or by first extracting or eluting the protein from the membrane. As an alternative example, the protein may be isolated by size-exclusion chromatography alone or in combination with other means of isolation and purification.

The invention also provides methods of producing monoclonal antibodies that specifically bind to homodimeric, heterodimeric, and/or multimeric forms of both IL-17A and IL-17F. These different forms may be purified from cells or from recombinant systems using a variety of well-known techniques for isolating and purifying proteins. For example, but not by way of limitation, both IL-17A and IL-17F may be isolated based on the apparent molecular weight of the protein by running the protein on an SDS-PAGE gel and blotting the proteins onto a membrane. Thereafter, the appropriate size band corresponding to each may be cut from the membrane and used as an immunogen in animals directly, or by first extracting or eluting the protein from the membrane. As an alternative example, the protein may be isolated by size-exclusion chromatography alone or in combination with other means of isolation and purification.

Other means of purification are available in such standard reference texts as Zola, *Monoclonal Antibodies: Preparation And Use Of Monoclonal Antibodies And Engineered Antibody Derivatives (Basics: From Background To Bench)* Springer-Verlag Ltd., New York, 2000; *Basic Methods In Antibody Production And Characterization*, Chapter 11, "Antibody Purification Methods," Howard and Bethell, Eds., CRC Press, 2000; *Antibody Engineering (Springer Lab Manual)*, Kontermann and Dubel, Eds., Springer-Verlag, 2001.

For in vivo antibody production, animals are generally immunized with either IL-17A or IL-17F or an immunogenic portion of either (e.g. shared epitopes as described above). The antigen is generally combined with an adjuvant to promote immunogenicity. Adjuvants vary according to the species used for immunization. Examples of adjuvants include, but are not limited to: Freund's complete adjuvant ("FCA"), Freund's incomplete adjuvant ("FIA"), mineral gels (e.g., aluminum hydroxide), surface active substances (e.g., lysolecithin, pluronic polyols, polyanions), peptides, oil emulsions, keyhole limpet hemocyanin ("KLH"), dinitrophenol ("DNP"), and potentially useful human adjuvants such as Bacille Calmette-Guerin ("BCG") and *corynebacterium parvum*. Such adjuvants are also well known in the art. Immunization may be accomplished using well-known procedures. The dose and immunization regimen will depend on the species of mammal immunized, its immune status, body weight, and/or calculated surface area, etc. Typically, blood serum is sampled from the immunized mammals and assayed for anti-IL-17A and IL-17F antibodies using appropriate screening assays as described below, for example.

A common method for producing humanized antibodies is to graft CDR sequences from a MAb (produced by immunizing a rodent host) onto a human Ig backbone, and transfection of the chimeric genes into Chinese Hamster Ovary (CHO) cells which in turn produce a functional Ab that is secreted by the CHO cells (Shields, R. L., et al. (1995) Anti-IgE monoclonal antibodies that inhibit allergen-specific histamine release. Int Arch. Allergy Immunol. 107:412-413). The methods described within this application are also useful for generating genetic alterations within Ig genes or chimeric Igs transfected within host cells such as rodent cell lines, plants, yeast and prokaryotes (Frigerio L, et al. (2000) Assembly, secretion, and vacuolar delivery of a hybrid immunoglobulin in plants. Plant Physiol. 123:1483-1494).

Splenocytes from immunized animals may be immortalized by fusing the splenocytes (containing the antibody-producing B cells) with an immortal cell line such as a myeloma line. Typically, myeloma cell line is from the same species as the splenocyte donor. In one embodiment, the immortal cell line is sensitive to culture medium containing hypoxanthine, aminopterin and thymidine ("HAT medium"). In some embodiments, the myeloma cells are negative for Epstein-Barr virus (EBV) infection. In preferred embodiments, the myeloma cells are HAT-sensitive, EBV negative and Ig expression negative. Any suitable myeloma may be used. Murine hybridomas may be generated using mouse myeloma cell lines (e.g., the P3-NS1/1-Ag4-1, P3-x63-Ag8.653 or Sp2/O-Ag14 myeloma lines). These murine myeloma lines are available from the ATCC. These myeloma cells are fused to the donor splenocytes polyethylene glycol ("PEG"), preferably 1500 molecular weight polyethylene glycol ("PEG 1500"). Hybridoma cells resulting from the fusion are selected in HAT medium which kills unfused and unproductively fused myeloma cells. Unfused splenocytes die over a short period of time in culture. In some embodiments, the myeloma cells do not express immunoglobulin genes.

Hybridomas producing a desired antibody which are detected by screening assays such as those described below may be used to produce antibodies in culture or in animals. For example, the hybridoma cells may be cultured in a nutrient medium under conditions and for a time sufficient to allow the hybridoma cells to secrete the monoclonal antibodies into the culture medium. These techniques and culture media are well known by those skilled in the art.

Alternatively, the hybridoma cells may be injected into the peritoneum of an unimmunized animal. The cells proliferate in the peritoneal cavity and secrete the antibody, which accumulates as ascites fluid. The ascites fluid may be withdrawn from the peritoneal cavity with a syringe as a rich source of the monoclonal antibody.

Hybridomas expressing monoclonal antibodies to IL-17A and IL-17F were produced using methods similar to those described above were deposited with the American Type Tissue Culture Collection ("ATCC"; which is located at 10801 University Blvd., Manassas, Va. 20110-2209 USA) patent depository as original deposits under the Budapest Treaty and were given the following ATCC Accession Nos.: clone 339.15.5.3 (ATCC Patent Deposit Designation PTA-7987, deposited on Nov. 7, 2006); clone 339.15.3.6 (ATCC Patent Deposit Designation PTA-7988, deposited on Nov. 7, 2006); and clone 339.15.6.16 (ATCC Patent Deposit Designation PTA-7989, deposited on Nov. 7, 2006).

Another non-limiting method for producing human antibodies is described in U.S. Pat. No. 5,789,650 which describes transgenic mammals that produce antibodies of another species (e.g., humans) with their own endogenous immunoglobulin genes being inactivated. The genes for the heterologous antibodies are encoded by human immunoglobulin genes. The transgenes containing the unrearranged immunoglobulin encoding regions are introduced into a non-human animal. The resulting transgenic animals are capable of functionally rearranging the transgenic immunoglobulin sequences and producing a repertoire of antibodies of various isotypes encoded by human immunoglobulin genes. The B-cells from the transgenic animals are subsequently immortalized by any of a variety of methods, including fusion with an immortalizing cell line (e.g., a myeloma cell).

The antibodies of the present invention may also be prepared in vitro using a variety of techniques known in the art. For example, but not by way of limitation, fully human monoclonal antibodies against IL-17A and IL-17F may be prepared by using in vitro-primed human splenocytes (Boerner et al. (1991) J. Immunol. 147:86-95).

Alternatively, for example, the antibodies of the invention may be prepared by "repertoire cloning" (Persson et al. (1991) Proc. Nat. Acad. Sci. USA 88:2432-2436; and Huang and Stollar (1991) J. Immunol. Methods 141:227-236). Further, U.S. Pat. No. 5,798,230 describes preparation of human monoclonal antibodies from human B antibody-producing B cells that are immortalized by infection with an Epstein-Barr virus that expresses Epstein-Barr virus nuclear antigen 2 (EBNA2). EBNA2, required for immortalization, is then inactivated resulting in increased antibody titers.

In another embodiment, antibodies of the invention are formed by in vitro immunization of peripheral blood mononuclear cells ("PBMCs"). This may be accomplished by any means known in the art, such as, for example, using methods described in the literature (Zafiropoulos et al. (1997) J. Immunological Methods 200:181-190).

In a specific embodiment, bispecific and single chain antibodies that bind both IL-17A and IL-17F are made. One method of the present invention is a method for producing a bispecific A/F antibody. The method comprises fusing hybridoma cells that secrete a monoclonal antibody that binds IL-17A, with hybridoma cells that secrete a monoclonal antibody that binds IL-17F, thereby preparing a hybrid hybridoma that secretes a bispecific A/F monclonal antibody. In one embodiment, the method comprises fusing hybridoma cells that secrete an antagonistic (or agonistic) IL-17A MAb, with hybridoma cells that secrete an antagonistic (or agonistic) IL-17F MAb. Conventional techniques for conducting such a fusion, and for isolating the desired hybrid hybridoma, include those described elsewhere herein, and those illustrated in the examples below.

U.S. Pat. No. 6,060,285 discloses a process for the production of bispecific antibodies, in which at least the genes for the light chain and the variable portion of the heavy chain of an antibody having a first specificity are transfected into a hybridoma cell secreting an antibody having a second specificity. When the transfected hybridoma cells are cultured, bispecific antibodies are produced, and may be isolated by various means known in the art.

Other investigators have used chemical coupling of antibody fragments to prepare antigen-binding molecules having specificity for two different antigens (Brennan et al., Science 229:81 1985; Glennie et al., J. Immunol. 139:2367, 1987). U.S. Pat. No. 6,010,902 also discusses techniques known in the art by which bispecific antibodies can be prepared, for example by the use of heterobifunctional cross-linking reagents such as GMBS (maleimidobutryloxy succinimide) or SPDP (N-succinimidyl 3-(2-pyridyldithio) propionate). (See, e.g., Hardy, "Purification And Coupling Of Fluorescent Proteins For Use In Flow Cytometry", Handbook Of Experimental Immunology, 4.sup.th Ed., Volume 1, Immunochemistry, Weir et al. (eds.), pp. 31.4-31.12, 1986).

The ability to produce antibodies via recombinant DNA technology has facilitated production of bispecific antibodies. Kostelny et al. utilized the leucine zipper moieties from the fos and jun proteins (which preferentially form heterodimers) to produce bispecific antibodies able to bind both the cell surface molecule CD3 and the receptor for Interleukin-2 (J. Immunol. 148:1547; 1992).

Single chain antibodies may be formed by linking heavy and light chain variable region (Fv region) fragments via an amino acid bridge (short peptide linker), resulting in a single polypeptide chain Such single-chain Fvs (scFvs) have been prepared by fusing DNA encoding a peptide linker between DNAs encoding the two variable region polypeptides (V.sub.L and V.sub.H). The resulting antibody fragments can form dimers or higher oligomers, depending on such factors as the length of a flexible linker between the two variable domains (Korff et al., Protein Engineering 10:423, 1997). In particular embodiments, two or more scFvs are joined by use of a chemical cross-linking agent.

Techniques developed for the production of single chain antibodies can be adapted to produce single chain antibodies of the present invention, that bind both IL-17A and IL-17F. Such techniques include those described in U.S. Pat. No. 4,946,778; Bird (Science 242:423, 1988); Huston et al. (Proc. Natl. Acad. Sci. USA 85:5879, 1988); and Ward et al. (Nature 334:544, 1989). Once desired single chain antibodies are identified (for example, from a phage-display library), those of skill in the art can further manipulate the DNA encoding the single chain antibody(ies) to yield bispecific antibodies, including bispecific antibodies having Fc regions.

Single chain antibodies against IL-17A and IL-17F may be concatamerized in either order (i.e., anti-IL-17A-anti-IL-17F or anti-IL-17F-anti-IL-17A). In particular embodiments, starting materials for preparing a bispecific A/F antibody include an antagonistic (or agonistic) single chain antibody directed against IL-17A and an antagonistic (or agonistic) single chain antibody directed against IL-17F.

U.S. Pat. No. 5,582,996 discloses the use of complementary interactive domains (such as leucine zipper moieties or other lock and key interactive domain structures) to facilitate heterodimer formation in the production of bispecific antibodies. The complementary interactive domain(s) may be inserted between an Fab fragment and another portion of a heavy chain (i.e., $C_{H1}$ or $C_{H2}$ regions of the heavy chain) The use of two different Fab fragments and complementary interactive domains that preferentially heterodimerize will result in bispecific antibody molecules. Cysteine residues may be introduced into the complementary interactive domains to allow disulphide bonding between the complementary interactive domains and stabilize the resulting bispecific antibodies.

Tetravalent, bispecific molecules can be prepared by fusion of DNA encoding the heavy chain of an F(ab')$_2$ fragment of an antibody with either DNA encoding the heavy chain of a second F(ab')$_2$ molecule (in which the CH1 domain is replaced by a CH3 domain), or with DNA encoding a single chain FIT fragment of an antibody, as described in U.S. Pat. No. 5,959,083. Expression of the resultant fusion genes in mammalian cells, together with the genes for the corresponding light chains, yields tetravalent bispecific molecules having specificity for selected antigens.

Bispecific antibodies can also be produced as described in U.S. Pat. No. 5,807,706, which is incorporated by reference herein. Generally, the method involves introducing a protuberance in a first polypeptide and a corresponding cavity in a second polypeptide, polypeptides interface. The protuberance and cavity are positioned so as to promote heteromultimer formation and hinder homomultimer formation. The protuberance is created by replacing amino acids having small side chains with amino acids having larger side chains. The cavity is created by the opposite approach, i.e., replacing amino acids having relatively large side chains with amino acids having smaller side chains.

The protuberance and cavity can be generated by conventional methods for making amino acid substitutions in polypeptides. For example, a nucleic acid encoding a polypeptide may be altered by conventional in vitro mutagenesis techniques. Alternatively, a polypeptide incorporating a desired amino acid substitution may be prepared by peptide synthesis Amino acids chosen for substitution are located at the interface between the first and second polypeptides.

F) Screening for Antibody Specificity

Screening for antibodies that specifically bind to both IL-17A and IL-17F may be accomplished using an enzyme-linked immunosorbent assay (ELISA) in which microtiter plates are coated with both IL-17A and IL-17F. In some embodiments, antibodies that bind both IL-17A and IL-17F from positively reacting clones can be further screened for reactivity in an ELISA-based assay using microtiter plates coated with the other forms IL-17A and IL-17F, or other IL-17 family members. Clones that produce antibodies that are reactive to another forms or family members are eliminated, and clones that produce antibodies that are reactive to both IL-17A and IL-17F may be selected for further expansion and development. Confirmation of reactivity of the antibodies to both IL-17A and IL-17F may be accomplished, for example, using a Western Blot assay in which protein from ovarian, breast, renal, colorectal, lung, endometrial, or brain cancer cells and purified FR-.alpha. and other folate receptor isoforms are run on an SDS-PAGE gel, and subsequently are blotted onto a membrane. The membrane may then be probed with the putative anti-FR-.alpha. antibodies. Reactivity with both IL-17A and IL-17F and not another family member confirms specificity of reactivity for both IL-17A and IL-17F.

In some embodiments, the binding affinity of the antibodies of the present invention antibodies is determined Antibodies of the invention preferably have a binding affinity to both IL-17A and IL-17F of at least about $1\times10^7$ M, more preferably at least about $1\times10^8$ M, more preferably at least about $1\times10^9$ M, and most preferably at least about $1\times10^{10}$ M. Preferred antibody-producing cells of the invention produce substantially only antibodies having a binding affinity to both IL-17A and IL-17F of at least about $1\times10^7$ M, more preferably at least about $1\times10^8$ M, more preferably at least about $1\times10^9$ M, and most preferably at least about $1\times10^{10}$ M. Preferred compositions of the invention comprise substantially only antibodies having a binding affinity to both IL-17A and IL-17F of at least about $1\times10^7$ M, more preferably at least about $1\times10^8$ M, more preferably at least about $1\times10^9$ M, and most preferably at least about $1\times10^{10}$ M.

The antibodies of the invention preferably induce antibody-dependent cellular cytotoxicity (ADCC) in IL-17RA and IL-17RC-bearing cells. ADCC assays are known in the art.

G) Anti-IL-17A and IL-17F Antibody-Producing Cells

Antibody-producing cells of the invention include any insect expression cell line known, such as for example, *Spodoptera frugiperda* cells. The expression cell lines may also be yeast cell lines, such as, for example, *Saccharomyces cerevisiae* and *Schizosaccharomyces pombe* cells. The expression cells may also be mammalian cells such as, for example, hybridoma cells (e.g., NS0 cells), Chinese hamster ovary cells, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK31 cells, mouse sertoli cells, human cervical carcinoma cells, buffalo rat liver cells, human lung cells, human liver cells, mouse mammary tumor cells, TRI cells, MRC 5 cells, and FS4 cells.

In some preferred embodiments, the antibody-producing cells of the invention produce antibodies that specifically bind to both IL-17A and IL-17F. The cells preferably are substantially free of both IL-17A and IL-17F binding competitors. In preferred embodiments, the antibody-producing cells comprise less than about 10%, preferably less than about 5%, more preferably less than about 1%, more preferably less than about 0.5%, more preferably less than about 0.1%, and most preferably 0% by weight both IL-17A and IL-17F binding competitors. In some preferred embodiments, the antibodies produced by the antibody-producing cells are substantially free of both IL-17A and IL-17F competitors. In preferred embodiments, antibodies produced by the antibody-producing cells comprise less than about 10%, preferably less than about 5%, more preferably less than about 1%, more preferably less than about 0.5%, more preferably less than about 0.1%, and most preferably 0% by weight both IL-17A and IL-17F binding competitors. Preferred antibody-producing cells of the invention produce substantially only antibodies having a binding affinity to both IL-17A and IL-17F of at least about $1\times10^{-7}$ M, more preferably at least about $1\times10^{-8}$ M, more preferably at least about $1\times10^{-9}$ M, and most preferably at least about $1\times10^{-10}$ M.

In some embodiments, the antibody-producing cells are the hybridomas expressing monoclonal antibodies to IL-17A and IL-17F that were deposited with the American Type Tissue Culture Collection ("ATCC"; which is located at 10801 University Blvd., Manassas, Va. 20110-2209 USA) patent depository as original deposits under the Budapest Treaty and were given the following ATCC Accession Nos.: clone 339.15.5.3 (ATCC Patent Deposit Designation PTA-7987, deposited on Nov. 7, 2006); clone 339.15.3.6 (ATCC Patent Deposit Designation PTA-7988, deposited on Nov. 7, 2006); and clone 339.15.6.16 (ATCC Patent Deposit Designation PTA-7989, deposited on Nov. 7, 2006).

H) Antibody Purification

Methods of antibody purification are known in the art. In some embodiments of the invention, methods for antibody purification include filtration, affinity column chromatography, cation exchange chromatography, anion exchange chromatography, and concentration. The filtration step preferably comprises ultrafiltration, and more preferably ultrafiltration and diafiltration. Filtration is preferably performed at least about 5-50 times, more preferably 10 to 30 times, and most preferably 14 to 27 times. Affinity column chromatography, may be performed using, for example, PROSEP Affinity Chromatography (Millipore, Billerica, Mass.). In a preferred embodiment, the affinity chromatography step comprises PROSEP-VA column chromatography. Eluate may be washed in a solvent detergent. Cation exchange chromatography may include, for example, SP-Sepharose Cation Exchange Chromatography. Anion exchange chromatography may include, for example but not limited to, Q-Sepharose Fast Flow Anion Exchange. The anion exchange step is preferably non-binding, thereby allowing removal of contaminants including DNA and BSA. The antibody product is preferably nanofiltered, for example, using a Pall DV 20 Nanofilter. The antibody product may be concentrated, for example, using ultrafiltration and diafiltration. The method may further comprise a step of size exclusion chromatography to remove aggregates.

I) Therapeutic Uses of the Cross-Reactive IL-17A and IL-17F Antibodies

Antibodies that cross-reactive to both IL-17A and IL-17F can be used to modulate the immune system by binding IL-17A and IL-17F (either singly or together), and thus, preventing the binding of IL-17A with either IL-17RA or IL-17RC and IL-17F with IL-17RC or any other receptor that they may bind, especially an IL-17 family member. The antibodies of the invention can also be used to modulate the immune system by inhibiting the binding of both IL-17A with the endogenous IL-17RA and/or IL-17RC receptor and IL-17F with the endogenous IL-17RC receptor. The antibodies of the invention can be also used to treat a subject which produces an excess of either IL-17A and/or IL-17F. Suitable subjects include mammals, such as humans. For example, the antibodies of the invention are useful in binding, blocking, inhibiting, reducing, antagonizing or neutralizing of both IL-17A and IL-17F (either singly or together), in the treatment of inflammation and inflammatory diseases such as psoriasis, psoriatic arthritis, rheumatoid arthritis, endotoxemia, inflammatory bowel disease (IBD), IBS, colitis, asthma, allograft rejection, immune mediated renal diseases, hepatobiliary diseases, multiple sclerosis, atherosclerosis, promotion of tumor growth, or degenerative joint disease and other inflammatory conditions disclosed herein.

Within preferred embodiments, the antibodies of the invention bind to, blocks, inhibits, reduces, antagonizes or neutralizes IL-17F and IL-17A (individually or together) in vivo.

Thus, particular embodiments of the present invention are directed toward use of the antibodies of the invention as antagonists in inflammatory and immune diseases or conditions such as psoriasis, psoriatic arthritis, atopic dermatitis, inflammatory skin conditions, rheumatoid arthritis, inflammatory bowel disease (IBD), Crohn's Disease, diverticulosis, asthma, pancreatitis, type I diabetes (IDDM), pancreatic cancer, pancreatitis, Graves Disease, colon and intestinal cancer, autoimmune disease, sepsis, organ or bone marrow transplant; inflammation due to endotoxemia, trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells), suppression of immune response to a pathogen or antigen, or other instances where inhibition of IL-17F and IL-17A cytokines is desired.

Moreover, the Antibodies of the Invention are Useful to:

(1) Block, inhibit, reduce, antagonize or neutralize signaling via IL-17A and IL-17F in the treatment of acute inflammation, inflammation as a result of trauma, tissue injury, surgery, sepsis or infection, and chronic inflammatory diseases such as asthma, inflammatory bowel disease (IBD), IBS, chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

(2) Block, inhibit, reduce, antagonize or neutralize signaling via IL-17A or IL-17F in the treatment of autoimmune diseases such as IDDM, multiple sclerosis (MS), systemic Lupus erythematosus (SLE), myasthenia gravis, rheumatoid arthritis, IBS and IBD to prevent or inhibit signaling in immune cells (e.g. lymphocytes, monocytes, leukocytes) via their receptors (e.g. IL-17RA and IL-17RC). Blocking, inhibiting, reducing, or antagonizing signaling via IL-17RA and IL-17RC, using the antibodies of the present invention, may also benefit diseases of the pancreas, kidney, pituitary and neuronal cells. IDDM, NIDDM, pancreatitis, and pancreatic carcinoma may benefit. Mabs to IL-17A and IL-17F may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

(3) Agonize, enhance, increase or initiate signaling via IL-17A or IL-17F receptors in the treatment of autoimmune diseases such as IDDM, MS, SLE, myasthenia gravis, rheumatoid arthritis, IBS, and IBD. Anti-IL-17A and IL-17F neutralizing and monoclonal antibodies may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., *J. Immunol.* 160:4841-4849, 1998) Similarly, agonistic antibodies may be used to signal, deplete and deviate immune cells involved in asthma, allergy and atopoic disease. Signaling via IL-17RA and IL-17RC may also benefit diseases of the pancreas, kidney, pituitary and neuronal cells. IDDM, NIDDM, pancreatitis, and pancreatic carcinoma may benefit.

The antibodies described herein can be used to bind, block, inhibit, reduce, antagonize or neutralize IL-17F and IL-17A activity, either singly or together, in the treatment of autoimmune disease, atopic disease, NIDDM, pancreatitis and kidney dysfunction as described above. The antibodes of the present invention are useful as antagonists of IL-17A or IL-17F cytokine. Such antagonistic effects can be achieved by direct neutralization or binding of IL-17A and IL-17F.

Inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., psoriasis, arthritis, rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that the antibodies of the present invention could have crucial therapeutic potential for a vast number of human and animal diseases, from asthma and allergy to autoimmunity and septic shock.

1. Arthritis

Arthritis, including osteoarthritis, rheumatoid arthritis, arthritic joints as a result of injury, and the like, are common inflammatory conditions which would benefit from the therapeutic use of antibodies that antagonize, neutralize or block both IL-17A and IL-17F. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2):135-149, 2002). One of those mediators could be IL-17A or IL-17F, and as such a molecule that binds or inhibits IL-17F or IL-17A activity, such as soluble IL-17RA, IL-17RA polypeptides, or anti IL-17RA antibodies or binding partners, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995).

One group has shown that an anti-mouse IL-17 antibody reduces symptoms in a mouse CIA-model relative to control mice, thus showing conceptually that an anti-IL-17A antibody may be beneficial in treating human disease, as the administration of a single mouse-IL-17-specific rat antisera reduced the symptoms of arthritis in the animals when introduced prophylactically or after symptoms of arthritis were already present in the model (Lubberts et al, *Arthritis Rheum.* 50:650-9, 2004). Therefore, an antibody that antagonizes, neutralizes or blocks IL-17A and IL-17F binding to their respective receptors can be used to neutralize IL-17A and/or IL-17F in the treatment of specific human diseases such as arthritis, psoriasis, psoriatic arthritis, endotoxemia, inflammatory bowel disease (IBD), IBS, colitis, and other inflammatory conditions disclosed herein.

The administration of antibodies of the invention to these CIA model mice is used to evaluate the use of such an antibody as an antagonist to IL-17A and IL-17F, which could be used to ameliorate symptoms and alter the course of disease. By way of example and without limitation, the injection of 10-200 ug of an antibody of the present invention per mouse (one to seven times a week for up to but not limited to 4 weeks via s.c., i.p., or i.m route of administration) can significantly reduce the disease score (paw score, incident of inflammation, or disease). Depending on the initiation of antibody administration (e.g. prior to or at the time of collagen immunization, or at any time point following the second collagen immunization, including those time points at which the disease has already progressed), such anti-IL-17A and IL-17F antibodies can be efficacious in preventing rheumatoid arthritis, as well as preventing its progression.

2. Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory proteins, such as antibodies of the invention, could aid in preventing and treating endotoxemia in humans and animals. Such antibodies could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., Lancet 338:732, 1991). A shock-like state can indeed be induced experimentally by a single injection of LPS into animals Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. Cell 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., Science 229:869, 1985). It is well established that 1 ug injection of E. coli LPS into a C57B1/6 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., Science 229:869, 1985). The potential immunointervention strategies for the prevention and/or treatment of septic shock include anti-TNF mAb, IL-1 receptor antagonist, LIF, IL-10, and G-CSF.

The administration of antibodies of the invention to these LPS-induced model may be used to evaluate the use of such antibodies to ameliorate symptoms and alter the course of LPS-induced disease. Moreover, results showing inhibition of IL-17A and IL-17F by antibodies of the invention provide proof of concept that such antibodies can also be used to ameliorate symptoms in the LPS-induced model and alter the course of disease. The model will show induction of IL-17A and IL-17F by LPS injection and the potential treatment of disease by such antibodies. Since LPS induces the production of pro-inflammatory factors possibly contributing to the pathology of endotoxemia, the neutralization of both IL-17A and IL-17F activity or other pro-inflammatory factors by antibodies of the invention can be used to reduce the symptoms of endotoxemia, such as seen in endotoxic shock.

3. Inflammatory Bowel Disease IBD

In the United States approximately 500,000 people suffer from Inflammatory Bowel Disease (IBD) which can affect either colon and rectum (Ulcerative colitis) or both, small and large intestine (Crohn's Disease). The pathogenesis of these diseases is unclear, but they involve chronic inflammation of the affected tissues. Antibodies that bind both IL-17A and IL-17F could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. Intern. Rev. Immunol. 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of antibodies of the invention to these TNBS or DSS models can be used to evaluate the use such antibodies to ameliorate symptoms and alter the course of gastrointestinal disease. Moreover, the results showing inhibition of IL-17A and IL-17F by such antibodies provide proof of concept that antibodies of the invention can also be used to ameliorate symptoms in the colitis/IBD models and alter the course of disease.

4. Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk Although it is highly visible, psoriasis is not a contagious disease. The pathogenesis of the diseases involves chronic inflammation of the affected tissues. Antibodies that bind both IL-17A and IL-17F could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy.

Antibodies that bind IL-17A and IL-17F may also be used within diagnostic systems for the detection of circulating levels of IL-17F or IL-17A, and in the detection of IL-17A and/or IL-17F associated with acute phase inflammatory response. Elevated or depressed levels of ligand or receptor polypeptides may be indicative of pathological conditions, including inflammation or cancer. IL-17A and IL-17F are known to induce associated acute phase inflammatory response. Moreover, detection of acute phase proteins or molecules such as IL-17A or IL-17F can be indicative of a chronic inflammatory condition in certain disease states (e.g., asthma, psoriasis, rheumatoid arthritis, colitis, IBD). Detection of such conditions serves to aid in disease diagnosis as well as help a physician in choosing proper therapy.

In addition to other disease models described herein, the activity of antibodies of the invention on inflammatory tissue derived from human psoriatic lesions can be measured in vivo using a severe combined immune deficient (SCID) mouse model. Several mouse models have been developed in which human cells are implanted into immunodeficient mice (collectively referred to as xenograft models); see, for example, Caftan A R, Douglas E, *Leuk. Res.* 18:513-22, 1994 and Flavell, D J, *Hematological Oncology* 14:67-82, 1996. As an in vivo xenograft model for psoriasis, human psoriatic skin tissue is implanted into the SCID mouse model, and challenged with an appropriate antagonist. Moreover, other psoriasis animal models in ther art may be used to evaluate the antibodies of the invention, such as human psoriatic skin grafts implanted into AGR129 mouse model, and challenged with an appropriate antagonist (e.g., see, Boyman, O et al., *J. Exp. Med* Online publication #20031482, 2004, incorporated hereing by reference). Anti-IL-17A and IL-17F antibodies that bind, block, inhibit, reduce, antagonize or neutralize the activity of IL-17A and IL-17F are preferred antagonists. Similarly, tissues or cells derived from human colitis, IBD, arthritis, or other inflammatory lestions can be used in the SCID model to assess the anti-inflammatory properties of the antibodies of the invention described herein.

Therapies designed to abolish, retard, or reduce inflammation using antibodies of the invention can be tested by administration of such antibodies to SCID mice bearing human inflammatory tissue (e.g., psoriatic lesions and the like), or other models described herein. Efficacy of treatment is measured and statistically evaluated as increased anti-inflammatory effect within the treated population over time using methods well known in the art. Some exemplary methods include, but are not limited to measuring for example, in a psoriasis model, epidermal thickness, the number of inflammatory cells in the upper dermis, and the grades of parakeratosis. Such methods are known in the art and described herein. For example, see Zeigler, M. et al. *Lab Invest* 81:1253, 2001; Zollner, T. M. et al. *J. Clin. Invest.* 109:671, 2002; Yamanaka, N. et al. *Microbiol. Immunol.* 45:507, 2001; Raychaudhuri, S. P. et al. *Br. J. Dermatol.* 144:931, 2001; Boehncke, W. H et al. *Arch. Dermatol. Res.* 291:104, 1999; Boehncke, W. H et al. *J. Invest. Dermatol.* 116:596, 2001; Nickoloff, B. J. et al. *Am. J. Pathol.* 146:580, 1995; Boehncke, W. H et al. *J. Cutan. Pathol.* 24:1, 1997; Sugai, J., M. et al. *J. Dermatol. Sci.* 17:85, 1998; and Villadsen L. S. et al. *J. Clin. Invest.* 112:1571, 2003. Inflammation may also be monitored over time using well-known methods such as flow cytometry (or PCR) to quantitate the number of inflammatory or lesional cells present in a sample, score (weight loss, diarrhea, rectal bleeding, colon length) for IBD, paw disease score and inflammation score for CIA RA model.

Moreover, Psoriasis is a chronic inflammatory skin disease that is associated with hyperplastic epidermal keratinocytes and infiltrating mononuclear cells, including CD4+ memory T cells, neutrophils and macrophages (Christophers, *Int. Arch. Allergy Immunol.*, 110:199, 1996). It is currently believed that environmental antigens play a significant role in initiating and contributing to the pathology of the disease. However, it is the loss of tolerance to self-antigens that is thought to mediate the pathology of psoriasis. Dendritic cells and CD4$^+$ T cells are thought to play an important role in antigen presentation and recognition that mediate the immune response leading to the pathology. We have recently developed a model of psoriasis based on the CD4+CD45RB transfer model (Davenport et al., *Internat. Immunopharmacol.*, 2:653-672). Antibodies of the present invention are administered to the mice Inhibition of disease scores (skin lesions, inflammatory cytokines) indicates the effectiveness of such antibodies in psoriasis.

5. Atopic Dermatitis.

AD is a common chronic inflammatory disease that is characterized by hyperactivated cytokines of the helper T cell subset 2 (Th2). Although the exact etiology of AD is unknown, multiple factors have been implicated, including hyperactive Th2 immune responses, autoimmunity, infection, allergens, and genetic predisposition. Key features of the disease include xerosis (dryness of the skin), pruritus (itchiness of the skin), conjunctivitis, inflammatory skin lesions, *Staphylococcus aureus* infection, elevated blood eosinophilia, elevation of serum IgE and IgG1, and chronic dermatitis with T cell, mast cell, macrophage and eosinophil infiltration. Colonization or infection with *S. aureus* has been recognized to exacerbate AD and perpetuate chronicity of this skin disease.

AD is often found in patients with asthma and allergic rhinitis, and is frequently the initial manifestation of allergic disease. About 20% of the population in Western countries suffer from these allergic diseases, and the incidence of AD in developed countries is rising for unknown reasons. AD typically begins in childhood and can often persist through adolescence into adulthood. Current treatments for AD include topical corticosteroids, oral cyclosporin A, non-corticosteroid immunosuppressants such as tacrolimus (FK506 in ointment form), and interferon-gamma. Despite the variety of treatments for AD, many patients' symptoms do not improve, or they have adverse reactions to medications, requiring the search for other, more effective therapeutic agents. The antibodies of the present invention, including the neutralizing anti-human IL-17A and IL-17F antibodies of the present invention, can be used to neutralize IL-17F and IL-17A in the treatment of specific human diseases such as atoptic dermatitis, inflammatory skin conditions, and other inflammatory conditions disclosed herein.

6. Asthma

IL-17 plays an important role in allergen-induced T cell activation and neutrophilic influx in the airways. The receptor for IL-17 is expressed in the airways (Yao, et al. Immunity 3:811 (1995)) and IL-17 mediated neutrophil recruitment in allergic asthma is largely induced by the chemoattractant IL-8, GRO-α and macrophage inflammatory protein-2 (MIP-2) produced by IL-17 stimulated human bronchial epithelial cells (HBECs) and human bronichial fibroblasts (Yao, et al. *J Immunol* 155: 5483 (1995)); Molet, et al. *J Allergy Clin Immunol* 108: 430 (2001)). IL-17 also stimulates HBECs to release IL-6, a neutrophil-activating factor (Fossiez, et al, *J Exp Med* 183:2593 (1996), and Linden, et al. *Int Arch Allergy Immunol* 126:179 (2001)) and has been shown to synergize with TNF-α to prolong the survival of human neutrophils in vitro (Laan, et al. *Eur Respir J* 21: 387 (2003)). Moreover, IL-17 is capable of amplifying the inflammatory responses in asthma by its ability to enhance the secretion of cytokines implicated in airway remodeling such as the profibrotic cytokines, IL-6 and IL-11 and inflammatory mediators granulocyte colony-stimulating factor (G-CSF) and granulocyte macrophage colony-stimulating factor (GM-CSF) (Molet, et al. *J Allergy Clin Immunol* 108:430 (2001)).

Clinical evidence shows that acute, severe exacerbations of asthma are associated with recruitment and activation of neutrophils in the airways, thus IL-17 is likely to play a significant role in asthma. Patients with mild asthma display a detectable increase in the local concentration of free, soluble IL-17A protein (Molet, et al. J Allergy Clin Immunol 108:430 (2001)) while healthy human volunteers with induced, severe airway inflammation due to the exposure to a swine confinement, display a pronounced increase in the concentration of free, soluble IL-17A protein in the bronchoalveolar space (Fossiez, et al, J Exp Med 183:2593 (1996), and Linden, et al. Int Arch Allergy Immunol 126:179 (2001)). Furthermore, IL-17 levels in sputum have correlated with individuals who have increased airway hyperreactivity Barczyk, et al. Respir Med 97:726 (2003).

In animal models of airway hyper-responsiveness, chronic inhalation of ovalbumin by sensitized mice resulted in bronchial eosinophilic inflammation and early induction of IL-17 mRNA expression in inflamed lung tissue, together with a bronchial neutrophilia Hellings, et al. Am J Respir Cell Mol Biol 28:42 (2003). Anti-IL-17 monoclonal antibodies strongly reduced bronchial neutrophilic influx but significantly enhanced IL-5 levels in both bronchoalveolar lavage fluid and serum, and aggravated allergen-induced bronchial eosinophilic influx, suggesting that IL-17A may be involved in determining the balance between neutrophil and eosinophil accumulation following antigen insult Id.

Among the IL-17 family members, IL-17F is most closely related to IL-17A. The biological activities mediated by IL-17F are similar to those of IL-17A, where IL-17F stimulates production of IL-6, IL-8 and G-CSF Hurst, et al. J Immunol 169:443 (2002). IL-17F also induces production of IL-2, transforming growth factor (TGF)-α, and monocyte chemoattractant protein (MCP) in endothelial cells Starnes, et al. J Immunol 167:4137 (2001). Similarly, allergen challenge can increase local IL-17F in patients with allergic asthma Kawaguchi, et al. J Immunol 167:4430 (2001). Gene delivery of IL-17F in murine lung increases neutrophils in the bronchoalveolar space, while mucosal transfer of the IL-17F gene enhances the levels of Ag-induced pulmonary neutrophilia and airway responsiveness to methacholine Oda, et al. Am J Respir Crit Care Med 171:12 (2005).

Apart from asthma, several chronic inflammatory airway diseases are characterized by neutrophil recruitment in the airways and IL-17 has been reported to play an important role in the pathogenesis of respiratory conditions such as chronic obstructive pulmonary disease (COPD), bacterial pneumonia and cystic fibrosis (Linden, et al. Eur Respir J 15:973 (2000), Ye, et al. Am J Respir Cell Mol Biol 25:335 (2001), Rahman, et al. Clin Immunol 115:268 (2005)). An anti-IL-17A and anti-IL-17F antibody could be demonstrated to be efficacious for chronic inflammatory airway disease in an in vitro model of inflammation. The ability of antagonists to IL-17F and IL-17A activity, such as the antibodies of the present invention, to inhibit IL-17A or and IL-17F-induced cytokine and chemokine production from cultured HBECs or bronchial fibroblasts could be used as a measure of efficacy for such antagonists in the prevention of the production of inflammatory mediators directly resulting from IL-17A and/or F stimulation. If the addition of antagonists to IL-17F and IL-17A activity, such as the antibodies of the invention markedly reduces the production and expression of inflammatory mediators, it would be expected to be efficacious in inflammatory aspects associated with chronic airway inflammation.

7. Irritable Bowel Syndrome ("IBS")

Irritable bowel syndrome represents a disease characterized by abdominal pain or discomfort and an erratic bowel habit. IBS patients can be characterized into three main groups based on bowel habits: those with predominantly loose or frequent stools, those with predominantly hard or infrequent stools, and those with variable or normal stools (Talley et al., 2002). Altered intestinal motility, abnormalities in epithelial function, abnormal transit of stool and gas, and stress, may contribute to symptoms, while visceral hypersensitivity is a key feature in most patients. Genetic factors affecting pain-signaling and disturbances in central processing of afferent signals are postulated to predispose individuals to IBS following specific environmental exposures. Studies have also demonstrated that inflammatory responses in the colon may contribute to increased sensitivity of smooth muscle and enteric nerves and therefore perturb sensory-motor functions in the intestine (Collins et al., 2001). There is clinical overlap between IBS and IBD, with IBS-like symptoms frequently reported in patients before the diagnosis of IBD, and a higher than expected IBS symptoms in patients in remission from established IBD. Thus, these conditions may coexist with a higher than expected frequency, or may exist on a continuum, with IBS and IBD at different ends of the same spectrum. However, it should be noted that in most IBS patients, colonic biopsy specimens appear normal. Nevertheless, IBS significantly affects a very large number of individuals (U.S. prevalence in 2000, approximately 16 million individuals), resulting in a total cost burden of 1.7 billion dollars (year 2000). Thus, among the most prevalent and costly gastrointestinal diseases and disorders, IBS is second only to gastroesophageal reflux disease (GERD). Yet unlike GERD, treatment for IBS remains unsatisfactory (Talley et al., 2002; Farhadi et al., 21001; Collins et al., 2001), demonstrating that IBS clearly represents an unmet medical need.

Converging disease models have been proposed that postulate an enhanced responsiveness of neural, immune or neuroimmune circuits in the central nervous system (CNS) or in the gut to central (psychosocial) or peripheral (tissue irritation, inflammation, infection) perturbations of normal homeostasis (Talley et al., 2002). This enhanced responsiveness results in dysregulation of gut motility, epithelial function (immune, permeability), and visceral hypersensitivity, which in turn results in IBS symptoms.

There may be a role for a number of different molecules in the pathogenesis of IBS including a role for molecules that stimulate neurons and those that are involved in initiation of inflammatory process. A number of molecules are known to be linked to possible activity on neurons due to their direct expression by neurons or expression of their receptors on neurons, including IL-17D, IL-17B and IL-31. Moreover, a number of IL-17 family members and related molecules have been associated with inflammation in the gut, including IL-17A, IL-17F, IL-23 and IL-31.

Efficacy of inhibitors/antagonists of these molecules could be tested in vivo in animal models of disease. Several animal models have been proposed that mimic key features of IBS and involve centrally targeted stimuli (stress) or peripherally targeted stimuli (infection, inflammation). Two examples of in vivo animal models that can be used to determine the effectiveness of inhibitors in the treatment of IBS are (i) models focusing on primary CNS-directed pathogeneisis of IBS (stress models), and (ii) models focusing on gut-directed inducers of stress (i.e. gut inflammation, infection or physical stress). It should be noted however, that events within the CNS or in the gastrointestinal (GI) tract do not occur in isolation and that symptoms of IBS most likely result from a complex interaction between signals from the CNS on the GI and vice versa.

For pharmaceutical use, the antibodies of the present invention are formulated for parenteral, particularly intravenous or subcutaneous, delivery according to conventional methods. Intravenous administration will be by bolus injection, controlled release, e.g, using mini-pumps or other appropriate technology, or by infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents, albumin to provent protein loss on vial surfaces, etc. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. More commonly, the proteins will be administered over one week or less, often over a period of one to three days. In general, a therapeutically effective amount of antibodies of the present invention is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. The antibodies of the present invention can also be administered in combination with other cytokines such as IL-3, -6 and -11; stem cell factor; erythropoietin; G-CSF and GM-CSF. Within regimens of combination therapy, daily doses of other cytokines will in general be: EPO, 150 U/kg; GM-CSF, 5-15 lg/kg; IL-3, 1-5 lg/kg; and G-CSF, 1-25 lg/kg. Combination therapy with EPO, for example, is indicated in anemic patients with low EPO levels.

Generally, the dosage of administered antibodies will vary depending upon such factors as the patient's age, weight, height, sex, general medical condition and previous medical history. Typically, it is desirable to provide the recipient with a dosage of antibodies which is in the range of from about 1 pg/kg to 10 mg/kg (amount of agent/body weight of patient), although a lower or higher dosage also may be administered as circumstances dictate.

Administration of antibodies of the invention to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosalmembrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising antibodies of the invention can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., Science 269:850 (1995)). Transdermal delivery using electroporation provides another means to administer a molecule having IL-17A and IL-17F binding activity (Potts et al., *Pharm. Biotechnol.* 10:213 (1997)).

A pharmaceutical composition comprising an antibodies of the invention can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), Remington's Pharmaceutical Sciences, 19th Edition (Mack Publishing Company 1995).

For purposes of therapy, antibodies of the invention and a pharmaceutically acceptable carrier are administered to a patient in a therapeutically effective amount. A combination of a therapeutic molecule of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response. Effective treatment may be assessed in a variety of ways. In one embodiment, effective treatment is determined by reduced inflammation. In other embodiments, effective treatment is marked by inhibition of inflammation. In still other embodiments, effective therapy is measured by increased well-being of the patient including such signs as weight gain, regained strength, decreased pain, thriving, and subjective indications from the patient of better health.

A pharmaceutical composition comprising antibodies of the invention can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., Pharm. Biotechnol. 10:239 (1997); Ranade, "Implants in Drug Delivery," in Drug Delivery Systems, Ranade and Hollinger (eds.), pages 95-123 (CRC Press 1995); Bremer et al., "Protein Delivery with Infusion Pumps," in Protein Delivery: Physical Systems, Sanders and Hendren (eds.), pages 239-254 (Plenum Press 1997); Yewey et al., "Delivery of Proteins from a Controlled Release Injectable Implant," in Protein Delivery: Physical Systems, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., Eur. J. Clin. Microbiol. Infect. Dis. 12 (Suppl. 1):561 (1993), Kim, Drugs 46:618 (1993), and Ranade, "Site-Specific Drug Delivery Using Liposomes as Carriers," in Drug Delivery Systems, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., Liposomes In Cell Biology And Pharmacology (John Libbey 1987), and Ostro et al., American J. Hosp. Pharm. 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., Ann. N.Y. Acad. Sci. 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., Biochim. Biophys. Acta 802:428 (1984)). In addition, incorporation of glycolipid- or polyethelene glycol-derivatized phospholipids into liposome membranes has been shown to result in a significantly reduced uptake by the reticuloendothelial system (Allen et al., Biochim. Biophys. Acta 1068:133 (1991); Allen et al., Biochim. Biophys. Acta 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., Biol. Pharm. Bull. 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., Biol. Pharm. Bull. 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, Crit. Rev. Ther. Drug Carrier Syst. 14:287 (1997); Murahashi et al., Biol. Pharm. Bull. 20:259 (1997)). Similarly, Wu et al., Hepatology 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., Biol. Pharm. Bull. 20:259 (1997)). Polyaconitylated human serum albumin liposomes provide another approach for targeting liposomes to liver cells (Kamps et al., Proc. Nat'l Acad. Sci. USA 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Polypeptides and antibodies can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly(lactide-co-glycolide) (PLG), polyanhydrides, poly(ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified polypeptides having binding IL-17A and IL-17F activity such as anti-IL-17A and IL-17F antibodies, which a polypeptide is linked with a polymer, as discussed above.

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, Drug Delivery Systems (CRC Press 1996).

As an illustration, pharmaceutical compositions may be supplied as a kit comprising a container that comprises an antibody of the invention. Antibodies of the invention can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the antibody composition is contraindicated in patients with known hypersensitivity to IL-17A and IL-17F.

A pharmaceutical composition comprising antibodies of the invention can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):561 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies of the present invention, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

The antibodies of the invention can be encapsulated within liposomes using standard techniques of protein microencapsulation (see, for example, Anderson et al., *Infect. Immun* 31:1099 (1981), Anderson et al., *Cancer Res.* 50:1853 (1990), and Cohen et al., *Biochim Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim Biophys. Acta* 1150:9 (1993)).

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, Drug Delivery Systems (CRC Press 1996).

The present invention contemplates compositions of antibodies, wherein said antibodies bind to both IL-17A and IL-17F, and methods and therapeutic uses comprising an such an antibody as described herein. Such compositions can further comprise a carrier. The carrier can be a conventional organic or inorganic carrier. Examples of carriers include water, buffer solution, alcohol, propylene glycol, macrogol, sesame oil, corn oil, and the like.

The invention is further illustrated by the following non-limiting examples.

EXAMPLES

Example 1

IL-17F mRNA is Upregulated in a Murine Model of Asthma

IL-17F mRNA levels were measured in a sensitization and airway challenge model in mice. Groups of mice, 8 to 10 wks of age, were sensitized by intraperitoneal injection of 10 ug of recombinant *Dermatophagoides pteronyssinus* allergen 1 (DerP1) (Indoor biotechnologies, Cardiff, UK) in 50% Imject Alum (Pierce) on days 0 and 7. Seven days later, mice were challenged on 3 consecutive days (days 14, 15 and 16) with 20 ug of DerP1 in 50 ul PBS. There were 4 mice representing this group. Negative controls included 5 mice given phosphate buffered saline (PBS) sensitization, followed by PBS challenge. In addition to 3 mice given DerP1 sensitization, followed by PBS challenge. Forty-eight hours following allergen, or control challenge whole lung tissue was harvested and total RNA was isolated.

First strand cDNA was prepared using identical amounts of total RNA from each subject. IL-17F PCR was applied using Qiagen hotstar polymerase (Qiagen, Valencia, Calif.) and the manufacturer's recommendations. The IL-17F PCR utilized 35 cycles of amplification with sense primer, zc46098 (SEQ ID NO:9) and antisense primer, zc46099 (SEQ ID NO:10). In order to establish that the template quality was uniform amongst all subjects, Beta Actin PCR was applied to the same amount of each template used in the IL-17F amplification. B actin PCR included 25 cycles of PCR with sense primer, zc44779 (SEQ ID NO:11) and antisense primer, zc44776 (SEQ ID N:12).

All 4 mice from the DerP1 sensitized, DerP1 challenged treatment group (the asthma simulation) showed robust IL-17F amplification. In contrast, weak IL-17F amplification was seen from the negative controls, including 3 of 3 subjects representing the DerP1 sensitized/PBS challenged treatment group and 5 of 5 subjects from the PBS sensitized/PBS challenged treatment group. B actin amplification was at least as robust for the negative controls as for the asthma-simulated subjects, demonstrating that the weak negative control IL-17F amplification was not due to template problems.

Example 2

IL-17A Induces Elevated Levels of IFN-Gamma and TNF-Alpha in Human Peripheral Blood Mononuclear Cells Human peripheral blood mononuclear cells (PBMC) are purified by ficoll density gradient centrifugation and then incubated overnight at 37° C. in media alone, 50 ng/ml anti-human CD3 antibody, or the combination of 50 ng/ml anti-human CD3 antibody plus 1 □g/ml anti-human CD28 antibody. Replicate cultures for each of these conditions are set up and are given no cytokine, 25 ng/ml human IL-17A, or 25 ng/ml human IL-17F. After 24-hour incubations, supernatants from each culture are harvested and assayed for cytokine content using B-D Bioscience's human Th1/Th2 Cytometric Bead Array (CBA). We found that cultures that had been stimulated with either anti-CD3 or anti-CD3 plus anti-CD28 and had been supplemented with IL-17A contained significantly elevated levels of IFN-gamma and TNF-alpha (3-5-fold elevation of each) over cultures with no cytokine added or those that received IL-17F. Cultures in which no anti-CD3 stimulation was added did not show significant changes in cytokine levels. In addition, IL-17A addition induced no significant changes in other cytokines assayed for with the CBA including IL-2, IL-4, IL-5, and IL-10. This data indicates that IL-17A, but not IL-17F, can augment the production of IFN-gamma and TNF-alpha in PBMC cultures stimulated with anti-CD3 or anti-CD3 plus anti-CD28.

Example 3

An Anti-IL-17A and IL-17F Antibody Decreases Disease Incidence and Progression in Mouse Collagen Induced Arthritis (CIA) Model A) Mouse Collagen Induced Arthritis (CIA) Model Ten week old male DBA/1J mice (Jackson Labs) are divided into 3 groups of 13 mice/group. On day-21, animals are given an intradermal tail injection of 50-100 µl of 1 mg/ml chick Type II collagen formulated in Complete Freund's Adjuvant (prepared by Chondrex, Redmond, Wash.), and three weeks later on Day 0 they are given the same injection except prepared in Incomplete Freund's Adjuvant. An antibody of the invention (e.g. a cross-reacative antibody or a bispecific antibody) is administered as an intraperitoneal injection 3 times a week for 4 weeks, at different time points ranging from Day 0, to a day in which the majority of mice exhibit moderate symptoms of disease. Groups receive either 10 or 100 µg of the antibody per animal per dose, and control groups receive the vehicle control, PBS (Life Technologies, Rockville, Md.). Animals begin to show symptoms of arthritis following the second collagen injection, with most animals developing inflammation within 1.5-3 weeks. The extent of disease is evaluated in each paw by using a caliper to measure paw thickness, and by assigning a clinical score (0-3) to each paw: 0=Normal, 0.5=Toe(s) inflamed, 1=Mild paw inflammation, 2=Moderate paw inflammation, and 3=Severe paw inflammation as detailed below.

B) Monitoring Disease

Animals can begin to show signs of paw inflammation soon after the second collagen injection, and some animals may even begin to have signs of toe inflammation prior to the second collagen injection. Most animals develop arthritis within 1.5-3 weeks of the boost injection, but some may require a longer period of time. Incidence of disease in this model is typically 95-100%, and 0-2 non-responders (determined after 6 weeks of observation) are typically seen in a study using 40 animals. Note that as inflammation begins, a common transient occurrence of variable low-grade paw or toe inflammation can occur. For this reason, an animal is not considered to have established disease until marked, persistent paw swelling has developed.

All animals are observed daily to assess the status of the disease in their paws, which is done by assigning a qualitative clinical score to each of the paws. Every day, each animal has its 4 paws scored according to its state of clinical disease. To determine the clinical score, the paw can be thought of as having 3 zones, the toes, the paw itself (manus or pes), and the wrist or ankle joint. The extent and severity of the inflammation relative to these zones is noted including: observation of each toe for swelling; torn nails or redness of toes; notation of any evidence of edema or redness in any of the paws; notation of any loss of fine anatomic demarcation of tendons or bones; evaluation of the wrist or ankle for any edema or redness; and notation if the inflammation extends proximally up the leg. A paw score of 1, 2, or 3 is based first on the overall impression of severity, and second on how many zones are involved. The scale used for clinical scoring is shown below.

C) Clinical Score

0=Normal 0.5=One or more toes involved, but only the toes are inflamed

1=mild inflammation involving the paw (1 zone), and may include a toe or toes

2=moderate inflammation in the paw and may include some of the toes and/or the wrist/ankle (2 zones)

3=severe inflammation in the paw, wrist/ankle, and some or all of the toes (3 zones)

Established disease is defined as a qualitative score of paw inflammation ranking 2 or more, that persists for two days in a row. Once established disease is present, the date is recorded and designated as that animal's first day with "established disease".

Blood is collected throughout the experiment to monitor serum levels of anti-collagen antibodies, as well as serum immunoglobulin and cytokine levels. Serum anti-collagen antibodies correlate well with severity of disease Animals are euthanized on Day 21, and blood collected for serum and CBC's. From each animal, one affected paw is collected in 10% NBF for histology and one is frozen in liquid nitrogen and stored at −80° C. for mRNA analysis. Also, 1/2 spleen, 1/2 thymus, 1/2 mesenteric lymph node, one liver lobe and the left kidney are collected in RNAlater for RNA analysis, and 0.1/2 spleen, 1/2 thymus, 1/2 mesenteric lymph node, the remaining liver, and the right kidney are collected in 10% NBF for histology. Serum is collected and frozen at −80° C. for immunoglobulin and cytokine assays.

Groups of mice receiving an antibody of the invention at all time points are characterized by a delay in the onset and/or progression of paw inflammation. These results indicate that an IL-17A and IL-17F cross-reactive and/or bispecific antibody can reduce inflammation, as well as disease incidence and progression associated with this model. These results are further supported by the observation that administration of such antibody resulted in decreased levels of serum TNFa, IL-1b, and anti-collagen antibodies.

Example 4

An Anti-IL-17A and IL-17F Antibody Decreases Disease Incidence and Progression in an Inflammatory Bowel Disease (IBD) Model This model is designed to show that cultured intestinal tissue from patients with IBD produce higher levels of inflammatory mediators compared to tissue from healthy controls. This enhanced production of inflammatory mediators (including but not limited to IL-1b, IL-4, IL-5, IL-6, IL-8, IL-12, IL-13, IL-15, IL-17 A and F, IL-18, IL-23, TNF-a, IFN-g, MIP family members, MCP-1, G- and GM-CSF, etc.) contributes to the symptoms and pathology associated with IBDs such as Crohn's disease (CD) and ulcerative colitis (UC) by way of their effect(s) on activating inflammatory pathways and downstream effector cells. These pathways and components then lead to tissue and cell damage/destruction observed in vivo. Therefore, this model can simulate this enhanced inflammatory mediator aspect of IBD. Furthermore, when intestinal tissue from healthy controls or from human intestinal epithelial cell (IEC) lines is cultured in the presence of these inflammatory components, inflammatory pathway signaling can be observed, as well as evidence of tissue and cell damage.

Therapeutics that would be efficacious in human IBD in vivo would work in the above ex vivo or IEC models by inhibiting and/or neutralizing the production and/or presence of inflammatory mediators.

In this model, human intestinal tissue is collected from patients with IBD or from healthy controls undergoing intestinal biopsy, re-sectioning or from post-mortem tissue collection, and processed using a modification of Alexakis et al (Gut 53:85-90; 2004). Under aseptic conditions, samples are gently cleaned with copious amounts of PBS, followed by culturing of minced sections of tissue, in the presence of complete tissue culture media (plus antibiotics to prevent bacterial overgrowth). Samples from the same pool of minced tissue are treated with one of the following: vehicle (PBS); recombinant human (rh) IL-17A; rhIL-17F; or rhIL-17A+rhIL-17F. In addition, these are treated with or without an antibody of the invention (e.g. a cross-reactive or bispecific antibody). This experimental protocol is followed for studies with human IEC lines, with the exception that cells are passaged from existing stocks. After varying times in culture (from 1 h to several days), supernatants are collected and analyzed for levels of inflammatory mediators, including those listed above. In samples from patients with IBD or in samples treated with rhIL-17A and/or F, levels of inflammatory cytokines and chemokines are elevated compared to untreated healthy control tissue samples. The addition of an antibody of the invention markedly reduces the production of inflammatory mediators, and thus, would expect to be efficacious in human IBD.

Example 5

An Anti-IL-17A and IL-17F Antibody Decreases Disease Incidence and Progression in a Multiple Sclerosis (MS) Model Multiple sclerosis (MS) is a complex disease that is thought to be mediated by a number of factors, including the presence of lymphocytic and mononuclear cell inflammatory infiltrates and demyelination throughout the CNS. Microglia are macrophage-like cells that populate the central nervous system (CNS) and become activated upon injury or infection. Microglia have been implicated as playing critical roles in various CNS diseases including MS, and may be used to study mechanism(s) of initiation, progression, and therapy of the disease (Nagai et al. Neurobiol Dis 8:1057-1068; 2001; Olson et al. J Neurosci Methods 128:33-43; 2003) Immortalized human microglial cell lines and/or established human astroglia cell lines can, therefore, be used to study some of the effects of inflammatory mediators on these cell types and their potential for neutralization. Inflammatory mediators (including but not limited to IL-1b, IL-6, IL-8, IL-12, IL-13, IL-15, IL-17 A and F, IL-18, IL-23, TNF-a, IFN-g, MIP family members, RANTES, IP-10, MCP-1, G- and GM-CSF, etc.) can contribute to the symptoms and pathology associated with MS by way of their effect(s) on activating inflammatory pathways and downstream effector cells.

In order to evaluate the pro-inflammatory actions of IL-17A and IL-17F, and the ability of an antibody of the invention to neutralize or decrease these effects, cultured glial cells are treated with one of the following: vehicle; rhIL-17A; rhIL-17F; rhIL-17A+IL-17F. In addition, these are treated with or without an antibody of the invention. After varying times in culture (from 1 h to several days), supernatants and cells are collected and analyzed for levels and/or expression of inflammatory mediators, including those listed above. Levels of inflammatory cytokines and chemokines are elevated in the presence of rhIL-17A and/or IL-17F compared to cultures treated with vehicle alone. The addition of antibodies of the present invention markedly reduces the production and expression of inflammatory mediators, and thus, would expect to be efficacious in inflammatory aspects associated with human MS.

Example 6

An Anti-IL-17A and IL-17F Antibody Decreases Disease Incidence and Progression in a Rheumatoid Arthritis (RA) and Osteoarthritis (OA) Model This model is designed to show that human synovial cultures (including synovial macrophages, synovial fibroblasts, and articular chondrocytes) and explants from patients with RA and OA produce higher levels of inflammatory mediators compared to cultures/explants from healthy controls. This enhanced production of inflammatory mediators (including but not limited to oncostatin M, IL-1b, IL-6, IL-8, IL-12, IL-15, IL-17 A and F, IL-18, IL-23, TNF-a, IFN-g, IP-10, RANTES, RANKL, MIP family members, MCP-1, G- and GM-CSF, nitric oxide, etc.) contributes to the symptoms and pathology associated with RA and OA by way of their effect(s) on activating inflammatory pathways and downstream effector cells. These pathways and components then lead to inflammatory infiltrates, cartilage and matrix loss/destruction, bone loss, and upregulation of prostaglandins and cyclooxygenases. Therefore, this model can simulate the destructive inflammatory aspects of RA and OA in in vitro and ex vivo experiments. Furthermore, when explants and synovial cultures from healthy controls are cultured in the presence of several of these inflammatory components (e.g. oncostatin M, TNF-a, IL-1b, IL-6, IL-17A and F, IL-15, etc.), inflammatory pathway signaling can be observed. Therapeutics that would be efficacious in human RA in vivo would work in the above in vitro and ex vivo models by inhibiting and/or neutralizing the production and/or presence of inflammatory mediators.

In this model, human synovial explants are collected from patients with RA, OA, or from healthy controls undergoing joint replacement or from post-mortem tissue collection, and processed using a modification of Wooley and Tetlow (Arthritis Res 2: 65-70; 2000) and van't Hof et al (Rheumatology 39:1004-1008; 2000). Cultures of synovial fibroblasts, synovial macrophages and articular chondrocytes are also studied. Replicate samples are treated with one of the following: vehicle (PBS); recombinant human (rh) IL-17A; rhIL-17F; or rhIL-17A+rhIL-17F, and some samples contain various combinations of oncostatin M, TNF-a, IL-1b, IL-6, IL-17A, IL-17F, and IL-15. In addition, these are treated with or without an antibody of the invention. After varying time of culture (from 1 h to several days), supernatants are collected and analyzed for levels of inflammatory mediators, including those listed above. In samples from patients with RA or OA, or in samples treated with rhIL-17A and/or F (either alone or in combination with other inflammatory cytokines), levels of inflammatory cytokines and chemokines are elevated compared to untreated healthy control explants or in untreated cell cultures. The addition of antibodies of the present invention markedly reduces the production of inflammatory mediators, and thus, would expect to be efficacious in human RA and OA.

Example 7

IL-17A and IL-17F Expression in Murine Disease Models

Four murine models of disease (asthma, DSS colitis, atopic dermatitis and experimental allergic encephalomyelitis) were analyzed using know techniques for the expression of IL-17A and IL-17F.

In the asthma model, IL-17A and IL-17F are expressed at very low to undetectable levels in lung, spleen, lung draining lymph nodes and lung infiltrating cells in diseased and non-diseased mice.

Contrary to the asthma model, IL-17A and IL-17F were highly up-regulated in diseased but not normal mice in the DSS-colitis model in both proximal and distal colon. Neither cytokine was significantly up-regulated in the mesenteric lymph node. Further, it was found that up-regulation of both cytokines in the context of acute DSS-induced colitis and not in chronic DSS-induced colitis.

In atopic dermatitis, IL-17A mRNA was not detectable. IL-17F was found to be expressed in both skin and skin-draining lymph nodes but did not appear to be significantly regulated with disease.

In experimental allergic encephalomyelitis, both IL-17A and IL-17F appeared to up-regulated in spinal chord in diseased but not healthy mice. IL-17F may have been more highly expressed in lymph nodes compared to spinal cord but expression in the lymph nodes was not regulated with disease. However, overall levels of expression in these tissues was quite low.

In short, IL-17A and IL-17F expression appears to be regulated with disease in the context of the DSS-induced colitis and experimental allergic encephalomyelitis models but apparently not for asthma or atopic dermatitis.

Example 8

Construction of *E. Coli* Expression Vectors for Human IL-17A and F

IL-17A
Construction of pCHAN28
The human IL-17A expression construct was generated as follows. Native IL-17A sequence were generated by PCR amplification with two oligonucleotide primers zc48,686 (SEQ ID NO:13) and zc48,685 (SEQ ID NO:14). The PCR conditions were as follows: 25 cycles at 94° C. for 30 seconds, 50° C. for 30 seconds, and 72° C. for 1 minute; followed by a 4° C. soak. The DNA fragment was precipitated with 2 volume absolute ethanol Pellet was resuspended in 10 μL H$_2$O and used for recombination into SmaI cut recipient vector, pTAP238 to produce the constructs encoding human IL-17A. The resulting clones were designated as pCHAN28. They were digested with NotI (10 μL DNA, 5 μL buffer 3 New England BioLabs, 2 μL Not I, 33 μL H$_2$O for 1 hour at 37° C.) and religated with T4 DNA ligase buffer (7 μL of the previous digest, 2 μL of 5× buffer, 1 μL of T4 DNA ligase). This step removed the yeast sequence, CEN-ARS, to streamline the vector. Aliquots of the DNA were digested with Pvu2 and PstI to confirm the absence of the yeast sequence. The human IL-17A expression constructs were transformed into *E. coli* strain W3110. The polynucleotide sequence for human IL-17A is shown in SEQ ID NO:5 and the corresponding encoded IL-17A polypeptide is shown in SEQ ID NO:6.

IL-17F
Construction of pTAP419
The human IL-17F expression construct was generated as follows. Native IL-17F sequence were generated by PCR amplification with two oligonucleotide primers zc42,852 (SEQ ID NO:15) and zc42,854 (SEQ ID NO:16). The PCR conditions were as follows: 25 cycles at 94° C. for 30 seconds, 50° C. for 30 seconds, and 72° C. for 1 minute; followed by a 4° C. soak. The DNA fragment was precipitated with 2 volume absolute ethanol Pellet was resuspended in 10 μL H$_2$O and used for recombination into SmaI cut recipient vector, pTAP238 to produce the constructs encoding human IL-17F. The resulting clones were designated as pTAP419. They were digested with NotI (10 μL DNA, 5 μL buffer 3 New England BioLabs, 2 μL Not I, 33 μL H$_2$O for 1 hour at 37° C.) and religated with T4 DNA ligase buffer (7 μL of the previous digest, 2 μL of 5× buffer, 1 μL of T4 DNA ligase). This step removed the yeast sequence, CEN-ARS, to streamline the vector. Aliquots of the DNA were digested with Pvu2 and PstI to confirm the absence of the yeast sequence. The human IL-17F expression constructs were transformed into *E. coli* strain W3110. The polynucleotide sequence for human IL-17F is shown in SEQ ID NO:7, and the corresponding encoded IL-17F polypeptide is shown in SEQ ID NO:8.

Example 9

Expression of IL-17A in *E. Coli*

An expression plasmid containing pIL17A CH6 was constructed via homologous recombination using human IL17A CH6 and the expression vector pZMP20. The fragment was generated by PCR amplification using primers zc48895 (SEQ ID NO:17) and zc48893 (SEQ ID NO:18). The PCR fragment IL17A CH6 contains the IL17A coding region fused to a 6×His tag on the C-terminus, which was made using human IL17A as the template. The fragment includes a 5' overlap with the pZMP20 vector sequence as well as a 3' overlap with the pZMP20 vector at the insertion point. PCR conditions used were as follows: 1 cycle, 94° C., 5 minutes; 35 cycles, 94° C., 1 minute, followed by 55° C., 2 minutes, followed by 72° C., 3 minutes; 1 cycle, 72° C., 10 minutes. The PCR reaction mixture was run on a 1% agarose gel and a band corresponding to the size of the insert was gel-extracted using a QIAquick™ Gel Extraction Kit (Qiagen, Cat. No. 28704).

Plasmid pZMP20 is a mammalian expression vector containing an expression cassette having the CMV promoter, multiple restriction sites for insertion of coding sequences, an otPA signal peptide sequence (removed via recombination in this case); an internal ribosome entry site (IRES) element from poliovirus, and the extracellular domain of CD8 truncated at the C-terminal end of the transmembrane domain; an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*. The plasmid pZMP20 was cut with BglII (creating the insertion point) prior to recombination in yeast with the PCR fragment. One hundred microliters of competent yeast (*S. cerevisiae*) cells were independently combined with 10 µl of the insert DNA and 100 ng of cut pZMP20 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), ∞ ohms, and 25 µF. Six hundred µl of 1.2 M sorbitol was added to the cuvette, and the yeast was plated in a 100-µl and 300 µl aliquot onto two URA-D plates and incubated at 30° C. After about 72 hours, the Ura⁺ yeast transformants from a single plate were resuspended in 1 ml H₂O and spun briefly to pellet the yeast cells. The cell pellet was resuspended in 0.5 ml of lysis buffer (2% Triton X-100, 1% SDS, 100 mM NaCl, 10 mM Tris, pH 8.0, 1 mM EDTA). The five hundred microliters of the lysis mixture was added to an Eppendorf tube containing 250 µl acid-washed glass beads and 300 µl phenol-chloroform, was vortexed for 3 minutes, and spun for 5 minutes in an Eppendorf centrifuge at maximum speed. Three hundred microliters of the aqueous phase was transferred to a fresh tube, and the DNA was precipitated with 600 µl ethanol (EtOH), followed by centrifugation for 30 minutes at maximum speed. The tube was decanted and the pellet was washed with 1 mL of 70% ethanol. The tube was decanted and the DNA pellet was resuspended in 30 µl TE.

Transformation of electrocompetent *E. coli* host cells (DH12S) was done using 5 µl of the yeast DNA prep and 50 µl of cells. The cells were electropulsed at 2.0 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl₂, 10 mM MgSO₄, 20 mM glucose) was added and then the cells were plated in a 50 µl and a 200 µl aliquot on two LB AMP plates (LB broth (Lennox), 1.8% Bacto™ Agar (Difco), 100 mg/L Ampicillin).

The inserts of three clones for the construct was subjected to sequence analysis and one clone for each construct, containing the correct sequence, was selected. Larger scale plasmid DNA was isolated using a commercially available kit (QIAGEN Plasmid Mega Kit, Qiagen, Valencia, Calif.) according to manufacturer's instructions.

Expression of pIL17A CH6 was accomplished through transient transfection. Six 1000 mL flasks were seeded with 250 mL of 293F cells at 1E6 c/mL and were set aside. 20 mL of OptiMEM (Invitrogen, cat#31985-070) was placed in each of two 50 mL conical tubes. 2 mL of Lipofectamine 2000 (Invtirogen, cat#11668-019) was mixed into one of the OptiMEM containing 50 mL conical tubes and 1.5 mg of the IL17A CH6 pZMP20 expression plasmid was placed in the other tube. The tubes were inverted several times and allowed to incubate for 5 minutes at room temperature. The two tubes were then mixed together, inverted several times, and allowed to incubate for 30 minutes at room temperature. The DNA-Lipofectamine 2000 mixture was then evenly distributed into each of the six flasks while swirling the cell cultures. The flasks were then placed in an incubator on a shaker at 37° C., 6% CO₂, and shaking at 120 RPM. The cultures were harvested 96 hours later.

Example 10

Expression of IL-17F in *E. Coli*

An expression plasmid containing pIL17F CH6 was constructed via homologous recombination using a human IL17F CH6 and the expression vector pZMP20. The fragment was generated by PCR amplification using primers zc48894 (SEQ ID NO:19) and zc48892 (SEQ ID NO:20). The human IL17F CH6 contains a the IL17F coding region fused to a 6×His tag on the C-terminus, which was made using a previously generated clone of human IL17F as the template. The fragment includes a 5' overlap with the pZMP20 vector sequence as well as a 3' overlap with the pZMP20 vector at the insertion point. PCR conditions used were as follows: 1 cycle, 94° C., 5 minutes; 35 cycles, 94° C., 1 minute, followed by 55° C., 2 minutes, followed by 72° C., 3 minutes; 1 cycle, 72° C., 10 minutes. The PCR reaction mixture was run on a 1% agarose gel and a band corresponding to the size of the insert was gel-extracted using a QIAquick™ Gel Extraction Kit (Qiagen, Cat. No. 28704).

Plasmid pZMP20 is a mammalian expression vector containing an expression cassette having the CMV promoter, multiple restriction sites for insertion of coding sequences, an otPA signal peptide sequence (removed via recombination in this case); an internal ribosome entry site (IRES) element from poliovirus, and the extracellular domain of CD8 truncated at the C-terminal end of the transmembrane domain; an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*.

The plasmid pZMP20 was cut with BglII (creating the insertion point) prior to recombination in yeast with the PCR fragment. One hundred microliters of competent yeast (*S. cerevisiae*) cells were independently combined with 10 µl of the insert DNA and 100 ng of cut pZMP20 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), ∞ ohms, and 25 µF. Six hundred µl of 1.2 M sorbitol was added to the cuvette, and the yeast was plated in a 100-µl and 300 µl aliquot onto two URA-D plates and incubated at 30° C. After about 72 hours, the Ura⁺ yeast transformants from a single plate were resuspended in 1 ml H₂O and spun briefly to pellet the yeast cells. The cell pellet was resuspended in 0.5 ml of lysis buffer (2% Triton X-100, 1% SDS, 100 mM NaCl, 10 mM Tris, pH 8.0, 1 mM EDTA). The five hundred microliters of the lysis mixture was added to an Eppendorf tube containing 250 µl acid-washed glass beads and 300 µl phenol-chloroform, was vortexed for 3 minutes, and spun for 5 minutes in an Eppendorf centrifuge at maximum speed. Three hundred microliters of the aqueous phase was transferred to a fresh tube, and the DNA was precipitated with 600 µl ethanol (EtOH), followed by centrifugation for 30 minutes at maximum speed. The tube was decanted and the pellet was washed with 1 mL of 70% ethanol. The tube was decanted and the DNA pellet was resuspended in 30 µl TE.

Transformation of electrocompetent *E. coli* host cells (DH12S) was done using 5 µl of the yeast DNA prep and 50 µl of cells. The cells were electropulsed at 2.0 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 µl and a 200 µl aliquot on two LB AMP plates (LB broth (Lennox), 1.8% Bacto™ Agar (Difco), 100 mg/L Ampicillin).

The inserts of three clones for the construct was subjected to sequence analysis and one clone for each construct, containing the correct sequence, was selected. Larger scale plasmid DNA was isolated using a commercially available kit (QIAGEN Plasmid Mega Kit, Qiagen, Valencia, Calif.) according to manufacturer's instructions.

Expression of human IL17F CH6 was accomplished through transient transfection. Six 1000 mL flasks were seeded with 250 mL of 293F cells at 1E6 c/mL and were set aside. 20 mL of OptiMEM (Invitrogen, cat#31985-070) was placed in each of two 50 mL conical tubes. 2 mL of Lipofectamine 2000 (Invtirogen, cat#11668-019) was mixed into one of the OptiMEM containing 50 mL conical tubes and 1.5 mg of the IL17F CH6 pZMP20 expression plasmid was placed in the other tube. The tubes were inverted several times and allowed to incubate for 5 minutes at room temperature. The two tubes were then mixed together, inverted several times, and allowed to incubate for 30 minutes at room temperature. The DNA-Lipofectamine 2000 mixture was then evenly distributed into each of the six flasks while swirling the cell cultures. The flasks were then placed in an incubator on a shaker at 37° C., 6% $CO_2$, and shaking at 120 RPM. The cultures were harvested 96 hours later.

Example 11

Characterization of Monocolonal Antibodies that Bind to Both IL-17A and IL-17F

Two assays are performed with the antibody containing supernatants from the best first round clones in each set. First, the concentration of IgG in each supernatant used in the neutralization assay is determined using the Mouse-IgG ELISA kit (catalog #1 333 151 (Roche Applied Science). This enables enabled a determination of specific neutralizing activity for each supernatant and therefore identified hybridomas that were producing the most potent anti-IL17A and IL-17F and IL-17A plus IL-17F neutralizing mAbs. From this analysis the most potent mAbs are selected for further characterization. Second, preliminary epitope specificity ("binning") studies are performed with the supernatants using the Biacore 1000 surface plasmon resonance instrument.

Competitive Epitope Binding

Epitope binning and Western blotting experiments are performed to assess the functional binding characteristics of the monoclonal antibodies to IL-17A and IL-17F Binning studies are completed to determine antibodies that bind to different epitopes, or antigenic determinants, on IL-17A or IL-17F. Monoclonal antibodies that bind to the same, or a similar, epitope on IL-17A or IL-17F, respectively, are not able to bind simultaneously and are functionally grouped into a single family or "bin". Monoclonal antibodies that bind to different epitopes on IL-17A or IL-17F, are able to bind simultaneously and are grouped into separate families or "bins". Experiments were performed using a Biacore 1000™ instrument. Biacore is only one of a variety of assay formats that are routinely used epitope bin panels of monoclonal antibodies. Many references (e.g. The Epitope Mapping Protocols, Methods in Molecular Biology, Volume 6,6 Glenn E. Morris ed.) describe alternative methods that can be used (by those skilled in the art) to "bin" the monoclonal antibodies, and would be expected to provide consistent information regarding the binding characteristics of the monoclonal antibodies to IL-17A and IL-17F. Epitope binning experiments are performed with soluble, native antigen, *E. coli* derived or mammalian derived recombinant Il-17A and IL-17F.

Western Blotting

The ability of the monoclonal antibodies from the hybridomas to bind and detect denatured and reduced/denatured IL-17A and/or IL-17F is also evaluated using a Western Blot format.

Epitope Binning

A) Materials and Methods

Epitope binning studies are performed on a Biacore1000™ system (Biacore, Uppsalla Sweden). Methods are programmed using Method Definition Language (MDL) and run using Biacore Control Software, v 1.2. Polyclonal goat anti-Mouse IgG Fc antibody (Jackson ImmunoResearch Laboratories, West Grove, Pa.) is covalently immobilized to a Biacore CM5 sensor chip and is used to bind (capture) the primary monoclonal antibody of test series to the chip. Unoccupied Fc binding sites on the chip are then blocked using a polyclonal IgG Fc fragment (Jackson ImmunoResearch Laboratories, West Grove, Pa.). Subsequently, IL-17A or IL-17F is injected and allowed to specifically bind to the captured primary monoclonal antibody. The Biacore instrument measures the mass of protein bound to the sensor chip surface, and thus, binding of both the primary antibody and IL-17A or IL-17F antigen, are verified for each cycle. Following the binding of the primary antibody and antigen to the chip, a monoclonal antibody of the test series is injected as the secondary antibody, and allowed to bind to the pre-bound antigen. If the secondary monoclonal antibody is capable of binding the IL-17A or IL-17F antigen simultaneously with the primary monoclonal antibody, an increase in mass on the surface of the chip, or binding, is detected. If, however, the secondary monoclonal antibody is not capable of binding the IL-17A or IL-17F antigen simultaneously with the primary monoclonal antibody, no additional mass, or binding, is detected. Each monoclonal antibody is tested against itself and is used as the negative control to establish the level of the background (no-binding) signal.

Each purified monoclonal antibody is tested as the primary antibody in combination with the entire panel of selected monoclonal antibodies. All purified monoclonal antibodies are tested at equal concentrations. In between cycles, the goat anti-Mouse IgG Fc capture antibody on the chip is regenerated with 20 mM HCl. Control cycles are run to demonstrate a lack of response of the secondary antibody in the absence of primary antibody or antigen. Data is compiled using BioEvaluation 3.2 RCI software, then loaded into Excel™ for data processing.

B) Western Blotting

The ability of the monoclonal antibodies from each clone to detect denatured and reduced/denatured Il-17A or IL-17F from two sources is assessed using a Western blot format. A rabbit polyclonal antibody known to detect IL-17A and/or IL-17F in a Western blot format is used as a positive control.

Materials and Methods

The IL-17A and IL-17F antigen is obtained from two sources: IL-17A and IL-17F is either produced in *E. coli* or in mammalian cells such as 293 cells (as described herein) and purified. Aliquots of each antigen (100 ng/lane) is loaded onto 4-12% NuPAGE Bis-Tris gels (Invitrogen, Carlsbad, Calif.) in either non-reducing or reducing sample buffer (Invitrogen) along with molecular weight standards (SeeBlue; Invitrogen), and electrophoresis was performed in 1×MES running buffer (Invitrogen). Following electrophoresis, protein is transferred from the gel to 0.2 μm nitrocellulose membranes (Invitrogen). The nitrocellulose blots are blocked overnight in 2.5% non-fat dried milk in Western A buffer (ZymoGenetics, 50 mM Tris pH 7.4, 5 mM EDTA, 150 mM NaCl, 0.05% Igepal, 0.25% gelatin) then cut into sections and exposed to each antibody (0.2 μg/mL of each monoclonal or 0.5 μg/mL of the rabbit polyclonal antibody in Western A buffer). The blots are then probed with a secondary antibody conjugated to horseradish peroxidase; sheep anti-mouse IgG-HRP (Amersham: Piscataway, N.J.) for the monoclonal antibodies and donkey anti-rabbit Ig-HRP (Amersham) for the polyclonal antibodies. Bound antibody is then detected using a chemiluminescent reagent (Lumi-Light Plus Reagent: Roche, Mannheim, Germany) and images of the blots are recorded on a Lumi-Imager (Mannheim-Boehringer) or X-ray film (Kodak).

Example 12

Purification of C-Terminally his Tagged IL17A Protein from 293 Transient Cell System Murine IL-17A Delivered media adjusted to 25 mM Imidazole, 500 mM NaCl pH 7.5, via addition of solid (Fluka and JT Baker, respectively) (1.41 L total volume). Expression of his-tagged target analyzed via western blot via RP-HPLC (1.11 mg/L). Adjusted media loaded over Ni NTA His Bind Superflow (Novagen) column (5 mL, 1 cm diameter, Millipore) overnight at 4° C. Flow through checked via RP-HPLC and Western blot to be devoid of IL17A target. Ni NTA column washed with 50 mM NaPO4, 25 mM Imidazole, 0.5M NaCl pH 7.5 until UV @ A280 nm baseline stabilized. Column eluted in two steps: buffer as above adjusted to 45 mM and 500 mM Imidazole using 500 mM Imidazole stock. Elution fractions checked by silver stain analysis, with those containing target pooled (500 mM step elution). Ni NTA pool analyzed via RP-HPLC. Ni NTA pool concentrated to 2 mL against 10 kD MWCO Ultracel membrane (Millipore) and injected over Superdex® 75 column (GE Healthcare, 12/60 mm) running in 50 mM NaPO4, 109 mM NaCl pH 7.3 at 1.02 mL/min Two peaks resolved and analyzed via silver stain. The murine IL17A resolved nicely from the remaining contaminating proteins. Fractions containing pure target pooled, concentrated again to 2.0 mL using 10 kDa MWCO Ultracel membrane (Millipore), 0.22 um filtered, and aliquotted.

Human IL-17A

Delivered media adjusted to 25 mM Imidazole, 500 mM NaCl pH 7.5, via addition of solid (Fluka and JT Baker, respectively) (1.41 L total volume). Expression of his-tagged target analyzed via western blot using A1022G as standard and also via RP-HPLC (3.19 mg/L). Adjusted media loaded over Ni NTA His Bind Superflow (Novagen) column (5 mL, 1 cm diameter, Millipore) overnight at 4° C. Flow through checked via RP-HPLC and Western blot to be devoid of IL17A target. Ni NTA column washed with 50 mM NaPO4, 25 mM Imidazole, 0.5M NaCl pH 7.5 until UV @ A280 nm baseline stabilized. Column eluted in two steps: buffer as above adjusted to 45 mM and 500 mM Imidazole using 500 mM Imidazole stock. Elution fractions checked by silver stain analysis, with those containing target pooled (500 mM step elution). Ni NTA pool analyzed via RP-HPLC using A1022F as standard. Ni NTA pool concentrated to 5 mL against 10 kD MWCO Ultracel membrane (Millipore) and injected over Superdex® 75 column (GE Healthcare, 26/60 mm) running in 50 mM NaPO4, 109 mM NaCl pH 7.3 at 2.71 mL/min Two peaks resolved and analyzed via silver stain. The murine IL17A resolved nicely from the remaining contaminating proteins. Fractions containing pure target pooled, concentrated again to 9.0 mL using 10 kDa MWCO Ultracel membrane (Millipore), 0.22 um filtered, and aliquotted.

Example 13

Purification of C-Terminally his Tagged IL17F Protein from 293 Transient Cell System IMAC affinity capture on 293F media from transient expression. Media adjusted to 25 mM Imidazole; 25 mM NaPhos; 400 mM NaCl and pH 7.5. Thus adjusted media was loaded at 1 ml/min over a 5 ml bed of Qiagen NTA Superflow (1 cm dia) equilibrated in 25 mM NaPhos; 25 mM Imidazole; 500 mM NaCl at pH 7.5. Upon completing the load, the column was washed with 20CV equilibration buffer before eluting with a 10CV gradient formed between elution buffer and 25 mM NaPhos; 500 mM Imidazole; 500 mM NaCl at pH 7.5. Fractions were assayed by RP-HPLC for product, pooled and concentrated for SEC step. The concentrated pool from the IMAC step was injected onto a Pharmacia Superdex 75 SEC column equilibrated in 50 mM NaPhos; 109 mM NaCl at pH 7.2. A major symmetric peak eluting at ~0.5 CV contains the product. Samples were pooled and sterile filtered to 0.2 micron in preparation for aliquoting.

Example 14

Efficacy of an Antibody that Binds Both IL-17A and IL-17F in Human IBD Samples Via Epithelial Barrier Function Maintenance of epithelial barrier integrity is a critical factor in the preservation of a healthy gastrointestinal tract. Experimental evidence suggests that leakiness of the epithelial barrier in the gut may contribute to the development of IBD Immune cells located in the intestinal lamina propria generally interact with intestinal epithelial cells via cell to cell contact or production of soluble factors to maintain immune surveillance and contribute to epithelial barrier integrity. However, prolonged or dysregulated immune-mediated inflammation may contribute to defects in epithelial barrier cell integrity and function. The following study is designed to measure the direct effect(s) of T cell-derived IL-17A and/or IL-17F on epithelial barrier integrity.

In this example, intestinal epithelial cell lines, like Caco-2 cells, are differentiated on semipermeable membranes and co-cultured on the basolateral side with either T cells or monocytes derived from biopsies from IBD patients or normal individuals. Epithlelial monolayer integrity is monitored over time using assessment of transepithelial electrical resistance or resistance of the monolayer to dye diffusion. Decreases in transepithial resistance of monolayers in cocultures would suggest a disruption in the monolayer induced by the activity of the T cells or monocytes in the co-culture Inhibitors of IL-17A and IL-17F such as the antibodies of the present invention could be used to determine the relative contribution of IL-17A and IL-17F to the disruption of the epithelial monolayer and test whether inhibitors of IL-17A and IL-17F would be effective in maintaining epithelial barrier integrity. Prevention of epithelial monolayer disruption induced by activated T cells by such molecules would suggest that the antibodies of the present invention may be effective for the therapeutic treatment of IBD in humans.

Co-culture systems could also be generated using monolayers formed by primary epithelium from IBD patients to determine whether these cells are more sensitive to IL-17A and IL-17F compared to epithelial cells derived from healthy individuals. If so, these data would suggest that inhibiting IL-17A and IL-17F would be a suitable strategy for the therapeutic treatment of IBD.

Example 15

Effects of IL-17A and IL-17F on Lamina PropPria T Cells and Monocytes/Macrophages from Normal and Human IBD Samples Dysregulated or sustained immune-mediated inflammation may contribute to the symptoms and pathology associated with IBD by way of tissue damage or permanent skewing to inappropriate or prolonged immune responses. This model can determine the potential down-stream consequences of exposure of disease-associated T cells and monocytes to IL-17A and IL-17F which may be present in the immediate environmental cytokine mileu of the intestinal tissue.

Therapeutics that would be efficacious in human IBD in vivo would work in the above ex vivo models by inhibiting and/or neutralizing the production and/or presence of inflammatory mediators (including but not limited to IL-1b, IL-4, IL-5, IL-6, IL-8, IL-12, IL-13, IL-15, IL-17 A and F, IL-18, IL-23, TNF-a, IFN-g, MIP family members, MCP-1, G- and GM-CSF, etc.).

In this model, T cells and monocytes/macrophages are isolated from biopsy samples by carefully mincing biopsies with scissors in HBSS, treating with collagense and Dispase II and incubating for 1 hr at 37° C. in a shaker. The cell suspension is filtered through nylon mesh to remove debris and cell clumps and washed multiple times in HBSS. T cells and macrophage/monocytes can be isolated using direct cell sorting or bead-depletion/enrichment protocols. Isolated cells are incubated in the presence of IL-17A and IL-17F. This induces the production of inflammatory mediators by T cells and monocytes/macrophages or results in skewing subsequent T cell responses to highly pro-inflammatory responses. Comparisons between the types of inflammatory mediators produced by cells from IBD patients and those from cells of normal individuals can be made and might suggest that T cells and monocyte/macrophages from IBD patients produce a more pro-inflammatory profile in the presence of IL-17A and IL-17F. The addition of an antibody of the present invention to neutralize the production of downstream inflammatory mediators induced by IL-17A and IL-17F suggests that such antibodies may be efficacious in the therapeutic treatment of patients with IBD.

Example 16

Efficacy of Antibodies that to Both IL-17A and IL-17F in Irritable Bowel Syndrome ("IBS"): CNS-Directed Pathogenesis A model focusing on primary CNS-directed pathogenesis of IBS which employs stress stimuli to induce symptoms characteristic of IBS. The neonatal psychosocial stress model mimics some clinical features associated with IBS patients including visceral hyperalgesia, diarrhea and stress-sensitivity. Daily separation of the litter from their mothers for 180 minutes each day during postnatal days 4-18 will result in an alteration of maternal behaviour and significantly reduce times of the licking/grooming behaviour. The stress on the neonates results in permanent changes in the CNS resulting in altered stress-induced visceral and somatic pain sensitivity. Colonic motor function in response to stress is enhanced in these animals and preliminary data shows evidence of increased intestinal permeability (Mayer et al., 2002). Treatment with an antibody of the present invention and subsequent analysis of colonic motor function, epithelial permeability and response to stress stimuli could determine efficacy in this animal model of IBS. Decreases in the incidence of symptoms following treatment with these inhibitors would suggest potential efficacy in the treatment of IBS.

Example 17

Efficacy of Antibodies that to Both IL-17A and IL-17F in Irritable Bowel Syndrome ("IBS"): Primary Gut-Directed Inducers of Stress This is a model focusing on primary gut-directed inducers of stress (ie. gut inflammation, infection or physical stress) Animal studies have indicated that low-grade inflammation or immune activation may be a basis for altered motility, and/or afferent and epithelial function of the gut (Mayer et al, 2002). In this model, daily colon irritation is produced in neonatal animals (days 8-21) in the form of daily intracolonic injection of mustard oil. Mustard oil is a neural stimulant and has been shown to induce visceral hyperalgesia following intracolonic administration. This model mimics key features of the IBS including visceral hypersensitivity and alteration in bowel habits Animals also present with diarrhea or constipation, a key feature of IBS patients (Mayer et al., 2002; Kimball et al., 2005). An antibody of the present invention could be delivered to determine changes in the development of symptoms associated with this model. Decreases in the incidence or magnitude of visceral hypersensitivity and altered gut motility following therapeutic treatment with our inhibitors would suggest a potential for these molecules to be efficacious in the treatment of IBS.

Example 18

Generation of the IL-17A/F Antibodies

A) Capture Assay

The ability of anti-human IL-17F or anti-human IL-17A antibodies in the antisera to bind to IL-17F and/or IL-17A was assessed using a capture ELISA assay. In this assay, wells of 96 well polystyrene ELISA plates were first coated with 100 µL/well of goat anti-mouse IgG, Fc specific antibody (Jackson Immunoresearch) at a concentration of 1000 ng/mL in Coating Buffer (0.1M $Na_2CO_3$, pH 9.6). One plate for each ligand was prepared. Plates were incubated overnight at 4° C. after which unbound antibody was aspirated and the plates washed twice with 300 μL/well of Wash Buffer (PBS-Tween defined as 0.137M NaCl, 0.0027M KCl, 0.0072M $Na_2HPO_4$, 0.0015M $KH_2PO_4$, 0.05% v/v polysorbate 20, pH 7.2). Wells were blocked with 200 μL/well of Blocking Buffer (PBS-Tween plus 1% w/v bovine serum albumin (BSA)) for 1 hour, after which the plates were washed twice with Wash Buffer. Serial 10-fold dilutions (in Blocking Buffer) of the sera were prepared beginning with an initial dilution of 1:1000 and ranged to 1:1,000,000. Duplicate samples of each dilution were then transferred to the assay plate, 100 μL/well, in order to bind mouse IgG in the sera to the assay plate through the Fc portion of the molecule. Normal mouse sera served as a negative control, human IL17RC-Fc protein was added as a positive assay control. NOTE: Coating for this control was goat anti-human IgG, Fc specific antibody (Jackson Immunoresearch). Following a 1-hour incubation at RT, the wells were aspirated and the plates washed twice as described above. Biotinylated IL17F (6:1 molar ratio of biotin:protein) or biotinylated IL17A (10:1 molar ratio of biotin:protein) at concentrations of 500 ng/mL were then added to the wells (separate plates), 100 μL/well. Following a 1-hour incubation at RT, unbound biotinylated ligand was aspirated from the wells and the plates washed twice. Horseradish peroxidase labeled streptavidin (Pierce, Rockford, Ill.) at a concentration of 500 ng/mL was then added to each well, 100 μL/well, and the plates incubated at RT for 1 hour. After removal of unbound HRP-SA, the plates were washed 2 times, 100 μL/well of tetra methyl benzidine (TMB) (BioFX Laboratories, Owings Mills, Md.) added to each well and the plates incubated for 2 minutes at RT. Color development was stopped by the addition of 100 μL/well of 450 nm TMB Stop Reagent (BioFX Laboratories, Owings Mills, Md.) and the absorbance values of the wells read on a Molecular Devices Spectra MAX 340 instrument at 450 nm.

B) Direct Assay

The ability of anti-human IL-17F or anti-human IL-17A antibodies in the antisera to bind to IL-17F and/or IL-17A was assessed using a direct ELISA assay. In this assay, wells of 96 well polystyrene ELISA plates were first coated with 100 μL/well of IL-17F or IL-17A at concentrations of 1000 ng/mL in Coating Buffer (0.1M $Na_2CO_3$, pH 9.6). One plate for each ligand was prepared. Plates were incubated overnight at 4° C. after which unbound protein was aspirated and the plates washed twice with 300 μL/well of Wash Buffer (PBS-Tween defined as 0.137M NaCl, 0.0027M KCl, 0.0072M $Na_2HPO_4$, 0.0015M $KH_2PO_4$, 0.05% v/v polysorbate 20, pH 7.2). Wells were blocked with 200 μL/well of Blocking Buffer (PBS-Tween plus 1% w/v bovine serum albumin (BSA)) for 1 hour, after which the plates were washed twice with Wash Buffer. Serial 10-fold dilutions (in Blocking Buffer) of the sera were prepared beginning with an initial dilution of 1:1000 and ranged to 1:1,000,000. Duplicate samples of each dilution were then transferred to the assay plate, 100 μL/well, in order to bind specific protein in the sera to the assay plate. Normal mouse sera served as a negative control, zcytor14 (lot A1034F) was added as a positive assay control. Following a 1-hour incubation at RT, the wells were aspirated and the plates washed twice as described above. Horseradish peroxidase labeled goat anti-mouse IgG, Fc specific antibody (Jackson Immunoresearch) at a concentration of 1:5000 was then added to the wells both plates, 100 μL/well. Following a 1-hour incubation at RT, unbound antibody was aspirated from the wells and the plates washed twice. Tetra methyl benzidine (TMB) (BioFX Laboratories, Owings Mills, Md.), 100 μL/well, was added to each well and the plates incubated for 2 minutes at RT. Color development was stopped by the addition of 100 μL/well of 450 nm TMB Stop Reagent (BioFX Laboratories, Owings Mills, Md.) and the absorbance values of the wells read on a Molecular Devices Spectra MAX 340 instrument at 450 nm.

C) Neutralization Assay

The ability of anti-human IL-17F or anti-human IL-17A antibodies in the antisera to inhibit (neutralize) the stimulatory activity of IL-17F and/or IL-17A through its cognate receptor was assessed using a plate based neutralization assay. In this assay, wells of 96 well polystyrene ELISA plates were first coated with 100 μL/well of human IL17RC-Fc protein at a concentration of 1000 ng/mL in Coating Buffer (0.1M $Na_2CO_3$, pH 9.6). One plate for each ligand was prepared. Plates were incubated overnight at 4° C. after which unbound receptor was aspirated and the plates washed twice with 300 μL/well of Wash Buffer (PBS-Tween defined as 0.137M NaCl, 0.0027M KCl, 0.0072M $Na_2HPO_4$, 0.0015M $KH_2PO_4$, 0.05% v/v polysorbate 20, pH 7.2). Wells were blocked with 200 μL/well of Blocking Buffer (PBS-Tween plus 1% w/v bovine serum albumin (BSA)) for 1 hour, after which the plates were washed twice with Wash Buffer. Serial 10-fold dilutions (in Blocking Buffer) of the sera were prepared beginning with an initial dilution of 1:500 and ranged to 1:500,000. Biotinylated IL-17F (6:1 molar ratio of biotin:protein) or biotinylated IL-17A (10:1 molar ratio of biotin:protein) at a concentrations of 200 ng/ml were then added to the wells of the dilution plates (separate plates), 100 μL/well, mixed well by pipetting up and down several times and incubated 1 hour at RT. NOTE: The mixing of the sera dilutions and the biotinylated ligands at equal volumes results in the dilution series becoming 1:1000 through 1:1,000,000 and the ligand concentrations becoming 100 ng/ml. Duplicate samples of each sera dilution/biotinylated ligand solution were then transferred to the assay plate, 100 μL/well. Normal mouse sera served as a negative control, human IL-17RC-Fc protein was added as a positive assay control. Following a 1-hour incubation at RT, the wells were aspirated and the plates washed twice as described above. Horseradish peroxidase labeled streptavidin (Pierce, Rockford, Ill.) at a concentration of 500 ng/mL was then added to each well, 100 μL/well, and the plates incubated at RT for 1 hour. After removal of unbound HRP-SA, the plates were washed 2 times, 100 μL/well of tetra methyl benzidine (TMB) (BioFX Laboratories, Owings Mills, Md.) added to each well and the plates incubated for 3 minutes at RT. Color development was stopped by the addition of 100 μL/well of 450 nm TMB Stop Reagent (BioFX Laboratories, Owings Mills, Md.) and the absorbance values of the wells read on a Molecular Devices Spectra MAX 340 instrument at 450 nm.

D) Immunization Scheme

Five balb/C mice were immunized with IL-17F-BSA (50 μg each) every two weeks for 6 weeks (3 immunizations) via interperitoneal injection. Two weeks later, these mice were boosted with IL17A-BSA (50 μg each) via interperitoneal injection. Bleeds were taken each week after the last 3 boosts for sera evaluation. Approximately two months after the last boost, all 5 animals were boosted with IL-17A-BSA (50 μg each) via sub-cutaneous injection and a final bleed taken for sera evaluation.

E) Conclusion of Sera Evaluation by ELISA

Both the capture ELISA assay as well as the direct ELISA assay indicate that all five mice developed a significant antibody response to IL-17F. The direct assay indicates that four of the five mice also moderately binds IL-17A and one mouse weakly binds IL-17A. The neutralization assay indicates that two of the five mice moderately inhibit binding of IL-17F and two others weakly inhibit binding of IL-17F. One mouse does not inhibit binding of IL-17F at all. Also indicated by this assay is that two of the five mice weakly inhibit binding of IL-17A, whereas the other three do not inhibit binding. One mouse inhibits binding of both ligands to different degrees.

F) Fusion Procedure

After a minimum of four weeks post final immunization, the mouse with the most significant IL-17F and IL-17A neutralization titer was immunized a final time with approximately 50 µg of IL-17A-BSA in PBS via sub-cutaneous injection. Under normal conditions, five days later the spleen and lymph nodes of this mouse would have been harvested, prepared into a single cell suspension and fused to the Ag8 mouse myeloma cell line at a 2:1 lymphoid cell: myeloma cell ratio with PEG 1500 using the standard in-house protocol. In this instance, the mouse died post injection and the spleen was harvested, prepared into a single cell suspension and frozen at −80° C. for 5 days. After quickly thawing the spleen cell suspension, the fusion was completed as stated above. The fusion mixture was distributed into a series of 96 well flat-bottomed plates. Wells of the fusion plates were fed on days 4-7 (minimum of twice, maximum of 3 times). Wells were assayed eight days after plating of the fusion.

G) Screening of the Fusion

The capture ELISA and neutralization ELISA for IL-17F and IL-17A as described above were used to screen except that hybridoma supernatants were tested undiluted from the culture plates. All 'positive' clones (described in detail in Example 19) were verified by repeating both assays with the samples in duplicate. All 'positive' clones were expanded into culture in 24 well plates. When the density of the 24 well cultures was approximately 4-6×10$^5$ cells/mL, the supernatants (approximately 1.8 mL) were individually collected and stored for each clone and the cells from each well cryopreserved. The collected supernatants were used to further evaluate which clones meet the requested reagent needs. The appropriate clones were subjected to 1$^{st}$ and 2$^{nd}$ round cloning prior to scale up for purification.

Hybridomas expressing monoclonal antibodies to IL-17A and IL-17F were deposited with the American Type Tissue Culture Collection ("ATCC"; which is located at 10801 University Blvd., Manassas, Va. 20110-2209 USA) patent depository as original deposits under the Budapest Treaty and were given the following ATCC Accession Nos.: clone 339.15.5.3 (ATCC Patent Deposit Designation PTA-7987, deposited on Nov. 7, 2006); clone 339.15.3.6 (ATCC Patent Deposit Designation PTA-7988, deposited on Nov. 7, 2006); and clone 339.15.6.16 (ATCC Patent Deposit Designation PTA-7989, deposited on Nov. 7, 2006).

Example 19

IL-17A/F mAb Competitive Binding Assay Protocol

To assess the ability of the IL-17A/F antibodies of the present invention (as disclosed in Example 18) to bind the ligands IL-17A and IL-17F, a Flow Cytometry-based competitive binding assay was utilized. Incubation of a BHK cell line stably transfected with full length IL-17RC in the presence of the ligands IL-17A or IL-17F, and an IL-17A/F antibody of the present invention targeted to bind the ligands allows for detection and relative quantification of ligand bound to the cell surface (and therefore unbound by the antibody). The biotinylation of the ligand allows for FACS detection using a secondary Streptavidin conjugated fluorophore. A reduction in cell bound ligand over a titration of the antibody is recorded as a reduction in the mean fluorescence of the cells.

Biotinylated ligands are individually pre-mixed at 1 ug/ml with titrating amounts of antibody in staining media (HBSS+1% BSA+0.1% NaAzide+10 mM HEPES) in 100 ul volumes and incubated at RT for 15 minutes. A BHK cell line stably transfected with full length IL17RC is prepared for ligand staining by resuspension with Versene (Invitrogen cat.15040-066), equilibrating to 2×10e5 cells/100 ul, pelleting, and resuspension in the ligand/antibody pre-mix. Stained cells are incubated at 4° for 30 minutes, washed 1× in staining media, and stained with Streptavidin-PE (BD Pharmingen cat. 554061) at a 1:100 ratio. Cells are incubated at 4° in the dark for 30 minutes, washed 2× in staining media, and re-suspended in a 1:1 ratio of staining media and Cytofix (BD Bioscience 554655). The BD LSRII Flow Cytometer or similar instrument is used for data collection and analysis. The graph as shown in FIGURE represents a typical assay result using the proceeding protocol. The graph was generated using the Prizm software program. The Y values represent the MFI normalized to maximum and minimum (100% and 0%) based on ligand only and no ligand/no antibody control wells, and thus the percent binding of the ligand to the cells. The software calculates the IC50 for each curve.

Table 1 contains the IC50 values obtained for each IL-17A/F antibody.

TABLE 1

| Clone | Reactivity | Competitive Binding IC50 (ug/mL) | |
| --- | --- | --- | --- |
| | | IL17A | IL17F |
| 339.15.3.6 | IL17A & F | 38.0 | 3.5 |
| 339.15.5.3 | IL17A & F | 35.0 | 3.6 |
| 339.15.6.16 | IL17A & F | 28.0 | 3.5 |

From the foregoing, it will be appreciated that, although specific embodiments of the invention have been described herein for purposes of illustration, various modifications may be made without deviating from the spirit and scope of the invention.

What is claimed is:

1. A pharmaceutical composition comprising:
   (a) a cross-reactive humanized monoclonal antibody that binds to both IL-17A (SEQ ID NO:2) and IL-17F (SEQ ID NO:4); and
   (b) a pharmaceutically acceptable vehicle, carrier, or excipient,
   wherein the antibody inhibits the binding of both IL-17A and IL-17F to IL-17RC, wherein the antibody binds to the same epitope as the antibody produced by the hybridoma deposited with the American Type Culture Collection having ATCC Patent Deposit Designation PTA-7988, and
   wherein the composition is suitably formulated for parenteral, subcutaneous or intravenous administration to a human.

2. The composition of claim 1, wherein the isotype of the antibody is IgG.

3. The composition of claim 1, wherein the humanized antibody has a human immunoglobulin constant region.

* * * * *

SEQUENCE LISTING

<160> NUMBER OF SEQ ID NOS: 20

<210> SEQ ID NO 1
<211> LENGTH: 1874

```
<212> TYPE: DNA
<213> ORGANISM: Homo sapiens

<400> SEQUENCE: 1
gaattccggc aggcacaaac tcatccatcc ccagttgatt ggaagaaaca acgatgactc      60
ctggaagac ctcattggtg tcactgctac tgctgctgag cctggaggcc atagtgaagg     120
caggaatcac aatcccacga aatccaggat gcccaaattc tgaggacaag aacttccccc    180
ggactgtgat ggtcaacctg aacatccata accggaatac caataccaat cccaaaaggt    240
cctcagatta ctacaaccga tccacctcac cttggaatct ccaccgcaat gaggaccctg    300
agagatatcc ctctgtgatc tgggaggcaa agtgccgcca cttgggctgc atcaacgctg    360
atgggaacgt ggactaccac atgaactctg tccccatcca gcaagagatc ctggtcctgc    420
gcagggagcc tccacactgc ccaactcct tccggctgga agatactg tgtccgtgg        480
gctgcacctg tgtcaccccg attgtccacc atgtggccta agagctctgg ggagcccaca    540
ctccccaaag cagttagact atggagagcc gacccagccc tcaggaacc ctcatccttc     600
aaagacagcc tcatttcgga ctaaactcat tagagttctt aaggcagttt gtccaattaa    660
agcttcagag gtaacacttg gccaagatat gagatctgaa ttacctttcc ctctttccaa    720
gaaggaaggt ttgactgagt accaatttgc ttcttgttta ctttttaag ggctttaagt     780
tatttatgta tttaatatgc cctgagataa ctttggggta taagattcca ttttaatgaa    840
ttacctactt tattttgttt gtctttttaa agaagataag attctgggct tgggaatttt    900
attatttaaa aggtaaaacc tgtatttatt tgagctattt aaggatctat ttatgtttaa    960
gtatttagaa aaaggtgaaa agcactatt atcagttctg cctaggtaaa tgtaagatag    1020
aattaaatgg cagtgcaaaa tttctgagtc tttacaacat acggatatag tatttcctcc    1080
tctttgttt taaaagttat aacatggctg aaaagaaaga ttaaacctac tttcatatgt     1140
attaatttaa atttttgcaat ttgttgaggt tttacaagag atacagcaag tctaactctc   1200
tgttccatta aaccttata ataaaatcct tctgtaataa taaagtttca aagaaatg      1260
ttatttgtt ctcattaaat gtattttagc aaactcagct cttccctatt gggaagagtt    1320
atgcaaattc tcctataagc aaaacaaagc atgtctttga gtaacaatga cctgaaata    1380
cccaaaattc caagttctcg atttcacatg ccttcaagac tgaacaccga ctaaggtttt   1440
catactatta gccaatgctg tagacagaag cattttgata ggaatagagc aaataagata   1500
atggccctga ggaatggcat gtcattatta aagatcatat ggggaaaatg aaaccctccc   1560
caaaatacaa gaagttctgg gaggagacat tgtcttcaga ctacaatgtc cagtttctcc    1620
cctagactca ggcttccttt ggagattaag gccctcaga gatcaacaga ccaacatttt    1680
tctcttcctc aagcaacact cctagggcct ggcttctgtc tgatcaaggc accacacaac   1740
ccagaaagga gctgatgggg cagaatgaac tttaagtatg agaaaagttc agcccaagta    1800
aaataaaaac tcaatcacat tcaattccag agtagtttca agtttcacat cgtaaccatt   1860
ttcgcccgga attc                                                     1874

<210> SEQ ID NO 2
<211> LENGTH: 155
<212> TYPE: PRT
<213> ORGANISM: Homo sapiens

<400> SEQUENCE: 2

Met Thr Pro Gly Lys Thr Ser Leu Val Ser Leu Leu Leu Leu Leu Ser
 1               5                  10                  15
```

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
 50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 3
<211> LENGTH: 923
<212> TYPE: DNA
<213> ORGANISM: Homo sapiens

<400> SEQUENCE: 3
ggcttcagtt actagctagg ctactgagtt tagttctcag tttggcacct tgatacccttt      60
aggtgtgagt gttcccattt ccaggtgagg aactgaggtg caaagagaag ccctgatccc     120
ataaaaggac aggaatgctg agttccgcca gaccatgcat ctcttgctag taggtgaggc     180
gagtctctaa ctgattgcag cgtcttctat tttccaggtc aagtacttgc tgctgtcgat     240
attgggcctt gcctttctga gtgaggcggc agctcggaaa atccccaaag taggacatac     300
ttttttccaa aagcctgaga gttgcccgcc tgtgccagga ggtagtatga agcttgacat     360
tggcatcatc aatgaaaacc agcgcgtttc catgtcacgt aacatcgaga gccgctccac     420
ctcccccctgg aattacactg tcacttggga ccccaaccgg taccctcgg aagttgtaca      480
ggcccagtgt aggaacttgg gctgcatcaa tgctcaagga aaggaagaca tctccatgaa     540
ttccgttccc atccagcaag agaccctggt cgtccggagg aagcaccaag gctgctctgt     600
ttctttccag ttggagaagg tgctggtgac tgttggctgc acctgcgtca ccctgtcat      660
ccaccatgtg cagtaagagg tgcatatcca ctcagctgaa gaagctgtag aaatgccact     720
ccttacccag tgctctgcaa caagtcctgt ctgaccccca attccctcca cttcacagga     780
ctcttaataa gacctgcacg gatggaaaca taaaatattc acaatgtatg tgtgtatgta     840
ctacacttta tatttgatat ctaaaatgtt aggagaaaaa ttaatatatt cagtgctaat     900
ataataaagt attaataatg tta                                             923

<210> SEQ ID NO 4
<211> LENGTH: 153
<212> TYPE: PRT
<213> ORGANISM: Homo sapiens

<400> SEQUENCE: 4

Met Val Lys Tyr Leu Leu Leu Ser Ile Leu Gly Leu Ala Phe Leu Ser
  1               5                  10                  15

```
Glu Ala Ala Ala Arg Lys Ile Pro Lys Val Gly His Thr Phe Phe Gln
                 20                  25                  30

Lys Pro Glu Ser Cys Pro Val Pro Gly Gly Ser Met Lys Leu Asp
         35                  40                  45

Ile Gly Ile Ile Asn Glu Asn Gln Arg Val Ser Met Ser Arg Asn Ile
 50                  55                  60

Glu Ser Arg Ser Thr Ser Pro Trp Asn Tyr Thr Val Thr Trp Asp Pro
 65                  70                  75                  80

Asn Arg Tyr Pro Ser Glu Val Val Gln Ala Gln Cys Arg Asn Leu Gly
                 85                  90                  95

Cys Ile Asn Ala Gln Gly Lys Glu Asp Ile Ser Met Asn Ser Val Pro
                100                 105                 110

Ile Gln Gln Glu Thr Leu Val Val Arg Arg Lys His Gln Gly Cys Ser
            115                 120                 125

Val Ser Phe Gln Leu Glu Lys Val Leu Val Thr Val Gly Cys Thr Cys
        130                 135                 140

Val Thr Pro Val Ile His His Val Gln
145                 150

<210> SEQ ID NO 5
<211> LENGTH: 393
<212> TYPE: DNA
<213> ORGANISM: Homo sapiens

<400> SEQUENCE: 5
atgatcccac gaaatccagg atgcccaaat tctgaggaca agaacttccc ccggactgtg      60
atggtcaacc tgaacatcca taaccggaat accaatacca atcccaaaag gtcctcagat     120
tactacaacc gatccaccte accttggaat ctccaccgca atgaggaccc tgagagatat     180
ccctctgtga tctgggaggc aaagtgccgc cacttgggct gcatcaacgc tgatgggaac     240
gtggactacc acatgaactc tgtccccatc cagcaagaga tcctggtcct gcgcagggag     300
cctccacact gccccaactc cttccggctg gagaagatac tggtgtccgt gggctgcacc     360
tgtgtcaccc cgattgtcca ccatgtggcc taa                                  393

<210> SEQ ID NO 6
<211> LENGTH: 130
<212> TYPE: PRT
<213> ORGANISM: Homo sapiens

<400> SEQUENCE: 6

Met Ile Pro Arg Asn Pro Gly Cys Pro Asn Ser Glu Asp Lys Asn Phe
 1               5                  10                  15

Pro Arg Thr Val Met Val Asn Leu Asn Ile His Asn Arg Asn Thr Asn
                 20                  25                  30

Thr Asn Pro Lys Arg Ser Ser Asp Tyr Tyr Asn Arg Ser Thr Ser Pro
            35                  40                  45

Trp Asn Leu His Arg Asn Glu Asp Pro Glu Arg Tyr Pro Ser Val Ile
 50                  55                  60

Trp Glu Ala Lys Cys Arg His Leu Gly Cys Ile Asn Ala Asp Gly Asn
 65                  70                  75                  80

Val Asp Tyr His Met Asn Ser Val Pro Ile Gln Gln Glu Ile Leu Val
                 85                  90                  95

Leu Arg Arg Glu Pro Pro His Cys Pro Asn Ser Phe Arg Leu Glu Lys
                100                 105                 110

Ile Leu Val Ser Val Gly Cys Thr Cys Val Thr Pro Ile Val His His
```

```
                115                 120                 125

Val Ala
    130

<210> SEQ ID NO 7
<211> LENGTH: 405
<212> TYPE: DNA
<213> ORGANISM: Homo sapiens

<400> SEQUENCE: 7
atgcggaaaa tccccaaagt aggacatact tttttccaaa agcctgagag ttgcccgcct        60
gtgccaggag gtagtatgaa gcttgacatt ggcatcatca atgaaaacca gcgcgtttcc       120
atgtcacgta acatcgagag ccgctccacc tcccctgga attacactgt cacttgggac       180
cccaaccggt acccctcgga agttgtacag gcccagtgta ggaacttggg ctgcatcaat       240
gctcaaggaa aggaagacat ctccatgaat tccgttccca tccagcaaga gaccctggtc       300
gtccggagga agcaccaagg ctgctctgtt tctttccagt tggagaaggt gctggtgact       360
gttggctgca cctgcgtcac ccctgtcatc caccatgtgc agtaa                       405

<210> SEQ ID NO 8
<211> LENGTH: 134
<212> TYPE: PRT
<213> ORGANISM: Homo sapiens

<400> SEQUENCE: 8

Met Arg Lys Ile Pro Lys Val Gly His Thr Phe Phe Gln Lys Pro Glu
  1               5                  10                  15

Ser Cys Pro Pro Val Pro Gly Gly Ser Met Lys Leu Asp Ile Gly Ile
                 20                  25                  30

Ile Asn Glu Asn Gln Arg Val Ser Met Ser Arg Asn Ile Glu Ser Arg
             35                  40                  45

Ser Thr Ser Pro Trp Asn Tyr Thr Val Thr Trp Asp Pro Asn Arg Tyr
 50                  55                  60

Pro Ser Glu Val Val Gln Ala Gln Cys Arg Asn Leu Gly Cys Ile Asn
 65                  70                  75                  80

Ala Gln Gly Lys Glu Asp Ile Ser Met Asn Ser Val Pro Ile Gln Gln
                 85                  90                  95

Glu Thr Leu Val Val Arg Arg Lys His Gln Gly Cys Ser Val Ser Phe
            100                 105                 110

Gln Leu Glu Lys Val Leu Val Thr Val Gly Cys Thr Cys Val Thr Pro
            115                 120                 125

Val Ile His His Val Gln
    130

<210> SEQ ID NO 9
<211> LENGTH: 24
<212> TYPE: DNA
<213> ORGANISM: Artificial Sequence
<220> FEATURE:
<223> OTHER INFORMATION: primer zc46098

<400> SEQUENCE: 9
acttgccatt ctgagggagg tagc                                               24

<210> SEQ ID NO 10
<211> LENGTH: 24
<212> TYPE: DNA
<213> ORGANISM: Artificial Sequence
```

```
<220> FEATURE:
<223> OTHER INFORMATION: primer zc46099

<400> SEQUENCE: 10
cacaggtgca gccaactttt agga                                          24

<210> SEQ ID NO 11
<211> LENGTH: 20
<212> TYPE: DNA
<213> ORGANISM: Artificial Sequence
<220> FEATURE:
<223> OTHER INFORMATION: primer zc44779

<400> SEQUENCE: 11
gtgggccgct ctaggcacca                                               20

<210> SEQ ID NO 12
<211> LENGTH: 25
<212> TYPE: DNA
<213> ORGANISM: Artificial Sequence
<220> FEATURE:
<223> OTHER INFORMATION: primer zc44776

<400> SEQUENCE: 12
cggttggcct tagggttcag ggggg                                         25

<210> SEQ ID NO 13
<211> LENGTH: 64
<212> TYPE: DNA
<213> ORGANISM: Artificial Sequence
<220> FEATURE:
<223> OTHER INFORMATION: primer zc48686

<400> SEQUENCE: 13
tagaaataat tttgtttaac tttaagaagg agatatatat atgatcccac gaaatccagg   60
atgc                                                                64

<210> SEQ ID NO 14
<211> LENGTH: 67
<212> TYPE: DNA
<213> ORGANISM: Artificial Sequence
<220> FEATURE:
<223> OTHER INFORMATION: primer zc48685

<400> SEQUENCE: 14
tctgtatcag gctgaaaatc ttatctcatc cgccaaaaca ttaggccaca tggtggacaa   60
tcggggt                                                             67

<210> SEQ ID NO 15
<211> LENGTH: 66
<212> TYPE: DNA
<213> ORGANISM: Artificial Sequence
<220> FEATURE:
<223> OTHER INFORMATION: primer zc42852

<400> SEQUENCE: 15
ctagaaataa ttttgtttaa ctttaagaag gagatatata tatgcggaaa atccccaaag   60
taggac                                                              66

<210> SEQ ID NO 16
<211> LENGTH: 48
<212> TYPE: DNA
<213> ORGANISM: Artificial Sequence
<220> FEATURE:
```

```
<223> OTHER INFORMATION: primer zc42854

<400> SEQUENCE: 16
tctgtatcag gctgaaaatc ttatctcatc cgccaaaaca ttactgca                48

<210> SEQ ID NO 17
<211> LENGTH: 59
<212> TYPE: DNA
<213> ORGANISM: Artificial Sequence
<220> FEATURE:
<223> OTHER INFORMATION: primer zc48895

<400> SEQUENCE: 17
acaggtgtcc agggaattca tataggccgg ccaccatgac tcctgggaag acctcattg    59

<210> SEQ ID NO 18
<211> LENGTH: 88
<212> TYPE: DNA
<213> ORGANISM: Artificial Sequence
<220> FEATURE:
<223> OTHER INFORMATION: primer zc48893

<400> SEQUENCE: 18
gtacaacccc agagctgttt taaggcgcgc ctctagatta atgatgatgg tgatggtgtc   60
cggaggccac atggtggaca atcggggt                                     88

<210> SEQ ID NO 19
<211> LENGTH: 63
<212> TYPE: DNA
<213> ORGANISM: Artificial Sequence
<220> FEATURE:
<223> OTHER INFORMATION: primer zc48894

<400> SEQUENCE: 19
ctccacaggt gtccagggaa ttcatatagg ccggccacca tgacagtgaa gaccctgcat   60
ggc                                                                63

<210> SEQ ID NO 20
<211> LENGTH: 90
<212> TYPE: DNA
<213> ORGANISM: Artificial Sequence
<220> FEATURE:
<223> OTHER INFORMATION: primer zc48892

<400> SEQUENCE: 20
gggtacaacc ccagagctgt tttaaggcgc gcctctagat taatgatgat ggtgatggtg   60
tccggactgc acatggtgga tgacaggggt                                   90
```